United States Patent [19]
Weiner et al.

[11] Patent Number: 5,474,933
[45] Date of Patent: Dec. 12, 1995

[54] MARINE *MELA* GENE

[75] Inventors: Ronald M. Weiner, Adelphi, Md.; William C. Fuqua, Jr., Norfolk, Va.

[73] Assignee: The University of Maryland, College Park, Md.

[21] Appl. No.: 148,945

[22] Filed: Nov. 8, 1993

Related U.S. Application Data

[63] Continuation-in-part of Ser. No. 974,837, Nov. 10, 1992, abandoned, which is a continuation of Ser. No. 496,804, Mar. 21, 1990, abandoned.

[51] Int. Cl.$^6$ .............................. C12N 1/20; C12N 15/00; C12P 21/06; C07H 19/00
[52] U.S. Cl. ..................... 435/252.3; 435/69.1; 435/212; 435/252.35; 435/320.1; 536/22.1; 536/23.2; 536/23.1; 536/23.7
[58] Field of Search ................................... 435/69.1, 212, 435/252.3, 252.35, 320.1; 536/22.1, 23.1, 23.2, 23.7

[56] References Cited

U.S. PATENT DOCUMENTS 5,047,344  9/1991  Weiner et al. ..................... 435/252.1

FOREIGN PATENT DOCUMENTS 213898  3/1987  European Pat. Off. ..

OTHER PUBLICATIONS

Glover Gene cloning pp. 1–19 (1984).
Fuqua et al. "The Cloning and Characterization of Marine Bacterial" Annual Meeting of ASM, May 8–13, 1988.
Michael Wrangstadh et al., "Starvation–specific formation of a peripheral exopolysaccharide by a marine *Pseudomonas* ssp. strain S9", *Biol. Abstr.* 90(6):AB–1060 Abst. No. 67829, Sep. 15, 1990.
L. Dagasan et al., "Activity of Cloned Tyrosinas from *Alteromonas colwelliana*", *Abstracts of the Annual Meeting 1989 of Amer. Soc. Microbiol.*, vol. 89, p. 253, Abstr. No. K–50.
W. C. Fuqua, "Genetic Characterization of the *Alteromonas colwelliana* tyrosinase" *Abstracts of the Annual Meeting 1989 of Amer. Soc. Microbiol.*, vol. 89, p. 185, Abst. No. H–95.
Marcel Salanoubat et al., "Molecular cloning and sequencing of sucrose synthase cDNA from potato (*Solanum tuberosum* L.): preliminary characterization of sucrose synthase mRNA distribution", *Gene*, vol. 60, pp. 47–56 (1987).
Pamela J. Hanic-Joyce et al., "Molecular Characterization of the Yeast *PRT1* Gene in Which Mutations Affect Translation Initiation and Regulation of Cell Proliferation", *The Journal of Biological Chemistry*, vol. 262, No. 6, pp. 2845–2851 (1987).
A. V. Kaliman et al., "The nucleotide sequence of the region of bacteriophage T5 early genes D10–D–15", *Nucleic Acids Research*, vol. 16, No. 21, pp. 10353–10354 (1988).
Ambaliou Sanni et al., "Structure and Expression of the Genes Encoding the α and β Subunits of Yeast Phenylalanyl–tRNA Synthetase", *The Journal of Biological Chemistry*, vol. 263, No. 30, pp. 15407–15415 (1988).
Peter J. Curtis, "Sequence Comparison of Human and Murine Erythrocyte alpha-spectrin cDNA", *Gene*, vol. 36, pp. 357–362 (1985).
Shigeki Shibahara et al., "Cloning and expression of cDNA encoding mouse tyrosinase", *Nucleic Acids Research*, vol. 14, No. 6, pp. 2413–2426 (1986).
Michael Wrangstadh et al., "The role of an extracellular polysaccharide produced by the marine *Pseudomonas* sp. S9 in cellular detachment during starvation", *Can. J. Microbiol*, vol. 35, pp. 309–312 (1988).
David G. Allison et al., "The Role of Exopolysaccharides in Adhesion of Freshwater Bacteria", *Journal of General Microbiology*, vol. 133, pp. 1319–1327 (1987).
R. R. Read et al., "Purification and characterization of adhesive exopolysaccharides from *Pseudomonas putida* and *Pseudomonas fluorescens*", *Can. J. Microbiol.*, vol. 33, pp. 1080–1090 (1987).
Edward J. Yurkow et al., "Purification of Tyrosinase to Homogeneity Based on its Resistance to Sodium Dodecyl Sulfate–Proteinase K Digestion", *Archives of Biochemistry and Biophysics*, vol. 275, No. 1, pp. 122–129 (1989).
Glen N. Gaulton et al., "Control of Tyrosinase Gene Expression and its Relationship to Neural Crest Induction in *Rana pipiens*", *The Journal of Biological Chemistry*, vol. 258, No. 24, pp. 14845–14849 (1983).
William K. Fitt, "Factors Influencing Bacterial Production of Inducers of Settlement Behavior of Larvae of the Oyster *Crassostrea gigas*", *Microb. Ecol.*, vol. 17, pp. 287–298 (1989).

*Primary Examiner*—Keith C. Furman
*Assistant Examiner*—Hyosuk Kim
*Attorney, Agent, or Firm*—Burns, Doane, Swecker & Mathis

[57] ABSTRACT

The present invention provides the isolated genes encoding marine melA from the genus Shewanella, especially from the species *S. colwelliana*, and the melA encoded thereby in homogeneous form. Further, the invention provides antibodies to marine melA as well as methods of using the melA to induce oyster larval settlement. Moreover, these marine melA genes are also useful as selectable markers for genetic engineering.

10 Claims, 24 Drawing Sheets

FIG. 2A

```
              10           20           30           40
              |            |            |            |
TGA CTT TAT GAG TCG CAC AGG TAT CGA AGC GGG CTA CAT GAC CTT 50           60           70           80           90
      |            |            |            |            |
ACA TCA AAA AGG CGT GCC GCA TGG ACC ACA ACC TGG TCG TAC TGA 100          110          120          130
              |            |            |            |
AGC CTC AGT GGG CAA AAC TGA AAC CTA TGA GTA TGC AGT AAT GGT 140          150          160          170          180
      |            |            |            |            |
GGA CAC CTT TGC ACC ACT GCA ACT GAC CCA GCA TGT CAA TCG TGC 190          200          210          220
              |            |            |            |
ATG AGC AAA GAT TAC AAC CGT TCC TGG CTA GAA GAG TAA AAG CGT 230          240          250          260          270
      |            |            |            |            |
TCA GCC AGT GCT GAA CAT CTA ATA AAT ATA ACA CCA GAG GTG ACA 280          290          300          310
              |            |            |            |
CCG AAG AGT GCC CTT GGT TGC AAT AAG TTG AAA GAG GAT AAT TAC 320          330          340          350          360
      |            |            |            |            |
ATG GCA AGC GAA CAA AAC CCA CTG GGT CTA CTT GGT ATC GAA TTC
Met Ala Ser Glu Gln Asn Pro Leu Gly Leu Leu Gly Ile Glu Phe 370          380          390          400
              |            |            |            |
ACT GAA TTT GCT ACA CCA GAT CTA GAT TTT ATG CAT AAA GTT TTT
Thr Glu Phe Ala Thr Pro Asp Leu Asp Phe Met His Lys Val Phe
```

FIG. 2B

```
     410           420           430           440           450
ATC GAC TTT GGT TTC TCA AAA CTT AAA AAA CAC AAG CAG AAA GAT
Ile Asp Phe Gly Phe Ser Lys Leu Lys Lys His Lys Gln Lys Asp 460           470           480           490
ATT GTT TAC TAT AAA CAA AAT GAT ATT AAC TTT TTA CTC AAC AAT
Ile Val Tyr Tyr Lys Gln Asn Asp Ile Asn Phe Leu Leu Asn Asn 500           510           520           530           540
GAA AAA CAG GGC TTT TCA GCC CAG TTT GCC AAA ACG CAT GGC CCA
Glu Lys Gln Gly Phe Ser Ala Gln Phe Ala Lys Thr His Gly Pro 550           560           570           580
GCC ATT AGT TCT ATG GGC TGG CGT GTA GAA GAT GCC AAC TTT GCC
Ala Ile Ser Ser Met Gly Trp Arg Val Glu Asp Ala Asn Phe Ala 590           600           610           620           630
TTT GAA GGT GCT GTA GCC CGT GGG GCT AAA CCC GCA GCA GAT GAG
Phe Glu Gly Ala Val Ala Arg Gly Ala Lys Pro Ala Ala Asp Glu 640           650           600           670
GTG AAA GAT CTT CCC TAT CCC GCT ATC TAT GGC ATT GGT GAC AGC
Val Lys Asp Leu Pro Tyr Pro Ala Ile Tyr Gly Ile Gly Asp Ser 680           690           700           710           720
CTT ATC TAC TTT ATC GAT ACG TTT GGC GAT GAC AAC AAT ATC TAG
Leu Ile Tyr Phe Ile Asp Thr Phe Gly Asp Asp Asn Asn Ile Tyr 730           740           750           760
ACT TCT GAT TTT GAA GCG TTA GAT GAG CCT ATC ATC ACC CAA GAG
Thr Ser Asp Phe Glu Ala Leu Asp Glu Pro Ile Ile Thr Gln Glu
```

FIG. 2C

```
      770           780           790           800           810
       |             |             |             |             |
AAA GGC TTC ATT GAG GTC GAC CAT CTC ACC AAT AAT GTC CAT AAG
Lys Gly Phe Ile Glu Val Asp His Leu Thr Asn Asn Val His Lys 820           830           840           850
               |             |             |             |
GGC ACC ATG GAA TAT TGG TCA AAC TTC TAC AAA GAC ATT TTT GGC
Gly Thr Met Glu Tyr Trp Ser Asn Phe Tyr Lys Asp Ile Phe Gly 860           870           880           890           900
       |             |             |             |             |
TTT ACA GAA GTG CGT TAC TTC GAC ATT AAG GGC TCA CAA ACA GCT
Phe Thr Glu Val Arg Tyr Phe Asp Ile Lys Gly Ser Gln Thr Ala 910           920           930           940
               |             |             |             |
CTT ATC TCT TAC GCC CTG CGC TCG CCA GAT GGT AGT TTC TGC ATT
Leu Ile Ser Tyr Ala Leu Arg Ser Pro Asp Gly Ser Phe Cys Ile 950           960           970           980           990
       |             |             |             |             |
CCA ATT AAC GAA GGC AAA GGC GAT GAT CGT AAC CAA ATT GAT GAG
Pro Ile Asn Glu Gly Lys Gly Asp Asp Arg Asn Gln Ile Asp Glu 1000          1010          1020          1030
               |             |             |             |
TAC TTA AAA GAG TAC GAT GGC CCA GGT GTC CAA CAC TTA GCG TTC
Tyr Leu Lys Glu Tyr Asp Gly Pro Gly Val Gln His Leu Ala Phe 1040          1050          1060          1070          1080
       |             |             |             |             |
CGT AGC CGC GAC ATA GTT GCC TCA CTG GAT GCC ATG GAA GGA AGC
Arg Ser Arg Asp Ile Val Ala Ser Leu Asp Ala Met Glu Gly Ser
```

```
 ———— melA ————              ———— lacZ ————
971ATCGTAACCAAATTGATGAGT---/---GGGGATCCGTCGACCTGCAGCC1013
   | | | | | | |                | | | | | | |
```

```
                *         *         *         *         *         *
       AAAAACCAGCATCGCGCTGGTTTTTTTTATTGCAGCACAACAATAAACCTCTACACTAGCA  60

CACTTAATTATCTACTCACTGGCCTAACGCTTTCATGTCAGAACATATTCTCATTGCGGT   120

ATTTTTACCGACCTTTTTTTTCGTCTCAATTACACCAGGTATGTGTATGACACTGGCCAT  180
                                                     M  T  L  A  M

GACTCTCGGTATGAGTATCGGTGTGCGCCGAACCTTATGGATGATGGTTGGTGAGCTAGC   240
        T  L  G  M  S  I  G  V  R  R  T  L  W  M  M  V  G  E  L  A

AGGCGTTGCCCTCGTGGCGATTGCCGCCGTAATGGGTGTCGCCAGTATGATGCTGAACTA  300
        G  V  A  L  V  A  I  A  A  V  M  G  V  A  S  M  M  L  N  Y

TCCACAACTCTTCGATATTTTAAAATGGGTCGGTGGGCTCTATCTTGGTTACATCGGCAT   360
        P  Q  L  F  D  I  L  K  W  V  G  G  L  Y  L  G  Y  I  G  I

TAGCATGTGGCGGGCCAAAGGGAAAATGGCCAACCTTGACAATACCTCCAGTCAGATCAG  420
        S  M  W  R  A  K  G  K  M  A  N  L  D  N  T  S  S  Q  I  S

TAATCGAGCGCTAATAACTCAAGGCTTTGTCACCGCAATTGCTAATCCAAAAGGCTGGGC  480
        N  R  A  L  I  T  Q  G  F  V  T  A  I  A  N  P  K  G  W  A

CTTTATGATCTCGCTGCTCCCCCCTTTTATCAGCGTTGACCAAGCGATTGCACCACAATT  540
        F  M  I  S  L  L  P  P  F  I  S  V  D  Q  A  I  A  P  Q  L

AATGGTATTACTGTCAATTATTATGATGACAGAGTTCTTCAGCATGCTTGCTTATGCGAG  600
        M  V  L  L  S  I  I  M  M  T  E  F  F  S  M  L  A  Y  A  S

CGGCGGAAAACCCTTAAACTGTTTTTAAGTCGAGGCGATAACATCAAGTGGATGAACCGC   660
        G  G  K  P  L  N  C  F  •

ATAGCAGGGAGTTTAATGATCTGTGTTGGCTTATGGTTGGCGCTAGGTTAACGCAGAGTC  720
```

FIG. 14

```
            10        20        30        40        50        60
MelA    MASEQNPLGLLGIEFTEFATPDLDFMHKVFIDFGFSKLKKHKQKDIVYYKQNDINFLLNN
         ::||:||:|:||:|:|:|:  :  ::  :|  :||:|:  :|:  ||   |:|:::|||
pHPPH   ADLYENPMGLMGFEFIELASPTPNTLEPIFEIMGFTKVATHRSKDVHLYRQGAINLILNN 70        80        90       100       110
MelA    EKQGFSAQFAKTHGPAISSMGWRVEDANFAFEGAVARGAKPAADEV--KDLPYPAIYGIG
        |  ::  ::  ||  :|||:::|:||:||:  :|:  |:  ||:|    :|  |||  |||  |||
pHPPH   EPHSVASYFAAEHGPSVCGMAFRVKDSQKAYKRALELGAQPIHIETGPMELNLPAIKGIG 120       130       140       150       160       170
MelA    DSLIYFIDTFGDDNNIYTSDFEALDEPIITQ-EKGFIEVDHLTNNVHKGTMEYWSNFYKD
        ::  :|:||  ||:::||  ||   |:   |:  :||||:|]::|  |:||:|||::
pHPPH   GAPLYLIDRFGEGSSIYDIDFVFLEGVDRHPVGAGLKIIDHLTHNVYRGRMAYWANFYEK 180       190       200       210       220       230
MelA    IFGFTEVRYFDIKGSQTALISYALRSPDGSFCIPINEGKGDDRNQIDEYLKEYDGPGVQH
        :|:|  |:||||||||  |:|  |:   :|||   |):||:::::    :||:|:|:::::|   |:||
pHPPH   LFNFREIRYFDIKGEYTGLTSKAMTAPDGMIRIPLNEESSKGAGQIEEFLMQFNGEGIQH 240       250       260       270       280       290
MelA    LAFRSRDIVASLDAMEGSSIQTLDIIPE-YYDTIFEKLPQVTEDRDRIKHHQILVDGDED
        :|| | |::  :  |  :::  ::  :: |:  ||  :  ::||:  :|    :  ||:|||:::
pHPPH   VAFLSDDLIKTWDHLKSIGMRFMTAPPDTYYEMLEGRLPNHGEPVGELQARGILLDGSSE 300       310       320       330       340
MelA    G----YLLQIFTKNLFGPIFIEIIQRKNNLGFGEGNFKALFESIERDQVRRGVL
        :    ||||:::|:||:|:|:|||||::  |||||||||||||||||||||||||||
pHPPH   SGDKRLLLQIFSETLMGPVFFEFIQRKGDDGFGEGNFKALFESIERDQVRRGVLSTD
```

FIG. 22

MARINE *MELA* GENE

CROSS REFERENCE TO RELATED APPLICATIONS

This application is a continuation-in-part of U.S. application Ser. No. 07/974,837, now abandoned, filed Nov. 10, 1992, which is a continuation of U.S. application Ser. No. 07/496,804, now abandoned, filed Mar. 21, 1990.

FIELD OF THE INVENTION

The present invention relates to marine melA genes from the genus Shewanella. Neither the melA or other marine genes that are involved in tyrosine conversion to pigment precursors have heretofore been extensively characterized, and it has been surprisingly found that the melA gene product from *S. colwelliana* differs substantially from that of other known genes involved with tyrosine metabolism, especially as relates to biochemical properties, and primary protein structure.

BACKGROUND OF THE INVENTION

*Shewanella colwelliana* are periphytic, gram-negative marine bacteria originally isolated from the walls of oyster spat tanks. The bacterium, originally designated LST (Lewis Spat Tank isolate), was temporarily assigned to the genus Alteromonas (R. M. Weiner, V. E. Coyne, P. Brayton, P. West, and S. F. Raiken (1988) *Int. J. System. Bact.* 38:240–244), and has now been reclassified to the recently established genus Shewanella (V. E. Coyne, C. J. Pillidge, D. D. Sledjeski, H. Hori, B. A. Ortiz-Conde, D. G. Muir, R. M. Weiner, and R. R. Colwell (1989) *System. Appl. Microbiol.* 12:275–279). These bacteria synthesize melanin, a brown-black polymeric pigment, and melanin metabolite precursors associated with an exopolysaccharide capable of inducing settlement and metamorphosis of oyster larvae, especially *Crassostrea virginica* larvae. Melanin synthesis occurs during late logarithmic and early stationary stages of growth.

Melanin is a general class of dark pigments found in bacteria, fungi, and higher organisms. This broad class of pigment is composed of complex polymers synthesized from phenolic or polyphenolic compounds (A. A. Bell and M. H. Wheeler (1986) *Ann. Rev. Phytopathol.* 24:411–451). The polymer is highly recalcitrant to degradation, and is observed frequently in the environment (i.e., humic soil deposits). Melanin is thought to be a "stable" free radical because it contains semiquinone free radicals that are stabilized by quinone and hydroxyquinone constituents of the polymer (A. A. Bell and M. H. Wheeler (1986) *An. Rev. Phytopathol.* 24:411–451). In addition, due to its complex composition melanin is capable of acting as either an oxidant or a reductant (M. S. Blois (1971) p. 125–139 in T. Kawamura, T. B. Fitzpatrick, and M. Seiji (eds), *Biology of Normal and Abnormal Melanocytes* Univ. Tokyo Press, Tokyo).

The classic Mason-Raper biosynthetic pathway for the synthesis of DOPA melanin was proposed in the late 1920's for one class of melanin (H. S. Raper (1928) *Physiol. Rev.* 8:245–282). In this pathway tyrosine is converted to DOPA via ortho-hydroxylation, and DOPA is then oxidized at both ring hydroxyl groups to form dopaquinone.

Melanogenesis has been documented for a number of bacterial species such as *Streptomyces, Bacillus, Rhizobium, Legionella,* and *Vibrio;* from fungi such as *Neurospora* and mushrooms; from amphibians such as *Xenopus;* and from mammals such as mice and humans. By far the best studied enzymes known to mediate melanogenesis are the tyrosinases (also known as catechol oxidase, phenolase, and polyphenol oxidase). Some of the genes encoding these tyrosinases have been cloned and sequenced but until the present invention no tyrosinase gene from a gram-negative bacterium or marine microorganism has been cloned or even isolated. In particular, cloned and sequenced tyrosinase genes have been reported from *Streptomyces antibioticus,* from *Streptomyces glaucescens,* from mouse pigment cells, and from human melanocytes [Bernan, V. et al. (1985) *Gene* 37:101–110; Hintermann, G. et al. (1985) *Mol. Gen. Genet.* 200:422–432; Shibahara, S. et al. (1986) *Nucleic Acids Res.* 14: 2413–2427; Kwon, B. S. et al. (1987) *Proc. Natl. Acad. Sci. USA* 84:7473–7477]. Additionally, the protein sequence of the *Neurospora crassa* tyrosinase has been determined [Lerch, K. (1982) *J. Biol. Chem.* 257:6414–6419].

Almost all genetic investigations in animals have focused on the mouse and human genes. A number of genetic loci have been defined in mice, where the $A^Y$ (lethal yellow) and e (extension) loci affect whether the melanin is black or yellow (sulfhydryl phaomelanin). Other loci, the b (brown), p (pink), and c (albino) appear to modulate the levels of tyrosinase activity in melanocytes (M. Jimenez, K. Tsukamoto, and V. J. Hearing (1991) *J. Biol. Chem.* 266:1147–1156). A gene encoding tyrosinase, corresponding to the b locus, was isolated from a cDNA library generated from B16 mouse melanoma cells (S. Shibahara, Y. Tomita, T. Sakakura, C. Nager, B. Chaudhuri, and R. Muller (1986) *Nucl. Acids Res.* 14:2413–2427). The DNA sequence encoded a protein predicted to be 58 kD after cleavage of a presumptive amino terminal signal sequence, in agreement with size estimates of purified mouse tyrosinase (J. B. Burnett (1971) *Biol. Chem.* 246:3079–3091). However, later studies disputed the authenticity of this clone. A second gene was cloned, that mapped to the c locus, and the authors claimed that the previous b locus gene was actually 5,6-hydroxyindole conversion factor, an accessory protein involved in mammalian melanogenesis (G. Muller, S. Ruppert, E. Schmid, and G. Schutz (1988) *EMBO J.* 7:2723–2730). The c locus gene encoded a protein of 58.5 kD, in general agreement with previous purified size estimates. Supporting these studies, the human tyrosinase gene was isolated from a cDNA library and also mapped to the c locus (B. Kwon, A. Haq, S. H. Pomerantz, and R. Halaban *Proc. Natl. Acad. Sci., USA* 84:7473–7477). Furthermore, individuals with oculocutaneous albinism have been shown to possess a missense mutation in the c locus (L. B. Giebel, K. M. Strunk, R. A. King, J. M. Hanifin, and R. A. Spritz (1990) *Proc. Natl. Acad. Sci., USA* 87:3255–3258).

The b locus and the c locus share a high degree of sequence conservation (86%) and also have the requisite copper-binding motifs of tyrosinases from Neurospora and Streptomyces (G. Muller, S. Ruppert, E. Schmid, and G. Schutz (1988) *EMBO J.* 7:2723–2730; S. Shibahara, Y. Tomita, T. Sakakura, C. Nager, B. Chaudhuri, and R. Muller (1986) *Nucl. Acids Res.* 14:2413–2427). More recent studies have further complicated the issue by revealing that both the b locus and the c locus gene products possess tyrosinase activity, and a locus encoding the TRP2 protein may be a third tyrosinase (M. Jimenez, K. Tsukamoto, and V. J. Hearing (1991) *J. Biol. Chem.* 266:1147–1156). These results suggest that a family of tyrosinases may mediate melanogenesis in mammals, each one functioning in a different aspect of the process. Reflecting this, the b locus protein is preferentially expressed in transformed melanocytes while the c locus is expressed at higher levels in normal melanocytes (M. Jimenez, K. Tsukamoto, and V. J. Hearing (1991) *J. Biol. Chem.* 266:1147–1156). The functions of the p, e, and A$^Y$ loci are yet to be determined but could be involved in regulation of tyrosinase(s).

The *Streptomyces tyrosinase* is the most extensively studied bacterial melanogenesis system. The ability to synthesize melanin is highly unstable and spontaneous mutants arise frequently (H. Schrempf (1983) *Mol. Gen. Genet.* 189:501–505). Two classes of mutants have been defined, Class I mutants defective in tyrosinase activity, and Class II mutants defective in tyrosine secretion (R. R. Crameri, L. Ettlinger, R. Hutter, K. Lerch, M. A. Suter, and J. A. Vetterli (1982) *J. Gen. Microbiol.* 128:371–379). Neither of these mutants demonstrated any detrimental effects from loss of melanin synthesis, suggesting that the gene was non-essential for growth in laboratory culture. The Class I mutants were further divided into three genetic loci mutable for tyrosinase gene expression (R. Crameri, G. Hintermann, R. Hutter, and T. Keiser (1984) *Can. J. Microbiol.* 30:1058–1067). The melA and melB loci were thought to be genes involved in the regulation of melanogenesis and melC the tyrosinase structural gene.

The tyrosinase genes for two species, *S. glaucescens* and *S. antibioticus* have been cloned and sequenced (V. Bernan, D. Filpula, W. Herber, M. Bibb and E. Katz (1985) *Gene* 37:101–110; G. Hintermann, M. Zatchez, and R. Hutter (1985) *Mol. Gen. Genet.* 200:422–432; M. Huber, G. Hintermann, and K. Lerch (1985) *Biochemistry* 24:6038–6044; E. Katz, C. J. Thompson, and D. A. Hopwood (1983) *J. Gen. Micro.* 129:2703–2714) and are the only bacterial melanogenesis genes reported to be cloned. The cloned fragments correspond to the melC locus defined in the earlier mutational analyses.

The role of melanin as an oxygen/free radical sink is an attractive hypothesis long proposed as a function for the polymer (A. A. Bell and M. H. Wheeler (1986) *Ann. Rev. Phytopathol.* 24:411–451). Most melanin synthesis systems, including those in Streptomyces, are dispensable for growth in the laboratory (H. Schrempf (1983) *Mol. Gen. Genet.* 189:501–505). Melanization may act as an oxygen/free radical sink, involved in coping with oxygen and oxidative stress it is possible that other melanizing bacteria also benefit from the trapping of free radicals and/or the increased oxygen demand during melanin polymerization.

When *S. colwelliana* D is grown on marine agar plates, the melanin diffuses outward from the colonies. Production is greatly enhanced by the addition of tyrosine, suggesting that the pigment is derived from tyrosine metabolism (Fuqua et al, *J. Gen. Microbiol.* 139:1105–1114 (1993)).

Some *Pseudomonas aeruginosa* strains produce melanin-like pigments when growth on peptone agar. (*Pigment Microbiology*, P. X. Margalith, ed. Chapman & Hall, pp. 11–13 (1992)). This would not take place in tyrosine-free media. Since tyrosinase inhibitors (KCN, Na$_2$S) are without effect and DOPA can not be identified in culture extracts, there are doubts with regard to the identity of the pigment. All melanin-forming strains have been found to accumulate homogentisic acid (2,5-di-hydroxyphenylacetic acid), while melanin negative strains do not. It has been argued that the melanin strains were not tyrosinase-positive, but rather mutants defective in the metabolism of homogentisic acid. Under oxidative conditions in the presence of amino acids this was polymerized into a brown aeruginosa melanin. A similar brown pigment was shown to be produced by strains of *Serratia marcescens* when cultivated on tyrosine.

In this organism, melanogenesis is mediated primarily by MelA, the product of the melA gene. (Fuqua et al, *Gene*, 109:131–136 (1991); Fuqua et al, *J. Gen. Microbiol.* 139:1105–1114 (1993)). When *E. coli* express the cloned melA gene, they are transformed to a melanogenic phenotype, which is again enhanced by tyrosine in the medium (Fuqua et al, *Gene* 09:131–136 (1991); Fuqua et al, *J. Gen. Microbiol.*, 139:1105–1114 (1993)). Analysis of lysates of *S. colwelliana* D and transformed *E. coli* demonstrate the accumulation of a dominant, electrochemically active intermediate, previously referred to as TyrP, (Fuqua, Doctoral dissertation. University of Maryland, College Park (1991)). a primary intermediate in pigment production by *S. colwelliana* D.

There are a variety of known pathways by which tyrosine can be converted to melanin. Melanins comprise a general class of complex, polyphenolic heteropolymers which are found as dark pigments in bacteria, fungi and higher organisms. Eumelanins are black and are synthesized by the classic Mason-Raper biosynthetic pathway in which a tyrosinase converts tyrosine to dihydroxyphenylalanine (DOPA) and then to dopaquinone which then autooxidizes and polymerizes to form eumelanin (Raper, *Physiol Rev.* 8:245–282 (1928)). Phaomelanins are brown, red or yellow pigments that form when dopaquinone reacts with glutathione or cysteine prior to further oxidation and polymerization. Structural analogues of tyrosine, or tyrosine metabolites, may also serve a s precursors for eumelanin and phaomelanin synthesis (Bell et al, Ann. Rev. *Phytopathol.* 24:411–451 (1986); Nicolaus, Melanins, Mermann, Paris (1968); Prota, *Arch. Biochem. Biophys.* 160:73–82 (1974)). Allomelanins, formed from catechol by a mechanism that is not well characterized, are described primarily from plants, but are also produced by bacteria. Pyomelanins, also called alkaptons, are produced from tyrosine through homogentisic acid (Yabuuchi et al, *Int. J. Syst Bact.* 22:53–65 (1972)). While most melanins fall into these categories, other types of melanins exist. (Bell et al, *Ann. Rev. Phytopathol.* 24:411–451 (1986)).

Bacteria are known to produce phaomelanins (Ivins et al, *Infect. Immun.* 34:895–899 (1981)) and pyomelanins (Yabuuchi et al, *Int. J. Syst Bact.* 22:53–65 (1972)). Melanin synthesis in bacteria has been most intensively studied in Streptomyces spp. (Lerch et al, *Eur. J. Biochem.* 52:125–138 (1981); Lerch et al, *Eur. J. Biochem.* 31:427–437 (1972)). These, and other bacteria (Aurstad et al, *Acta Vet. Scand.* 13:251–259 (1972); Pomerantz et al, *Arch. Biochem. Biophys.* 160:73–82 (1988)), synthesize a eumelanin via the action of tyrosinase on tyrosine via the MasonRaper pathway.

Preliminary experiments into the melanogenic pathway of *S. colwelliana* D indicated that TyrP was not an intermediate in the Mason-Raper melanogenic pathway. For example, TyrP was detected neither as a product of mushroom tyrosinase action on tyrosine, nor when DOPA was oxidized under a variety of conditions. TyrP was not found to coelute with authentic standards of known Mason-Raper intermediates or a multitude of related compounds.

SUMMARY OF THE INVENTION

The present invention provides a marine melA gene from the genus Shewanella. In particular, this gene may be an isolated nucleic acid, preferably DNA, RNA or recombinant DNA. Replicable expression vectors and transformed microorganisms and cells containing the nucleic acids or vectors are also provided. In a preferred embodiment, the invention is directed to the melA gene from *S. colwelliana*. The melA enzyme gene product encoded by this gene is active in catalyzing production of melanin synthesis as well as components in marine exopolysaccharides. Hence, the cloned gene is useful for increasing melA expression, in turn useful for a variety of purposes including adhesibility of marine exopolysaccharides and inducing oyster larval settlement.

Another aspect of the invention is directed to a marine melA from the genus Shewanella, including the recombinant form of the enzyme and peptide fragments of the protein.

A further aspect of this invention provides antibodies to a marine melA from the genus Shewanella and a method of using these antibodies in an immunoassay for detecting the melA.

Yet another aspect of the subject invention is directed to a method of detecting a melA gene from the genus Shewanella by a hybridization technique or by the polymerase chain reaction (PCR).

A still further aspect of the invention provides the subject melA gene as a selectable marker for genetic engineering.

Another aspect of the invention provides a bioremediation filter containing a mixture of exopolysachharide, homogentisic melanin and precursors thereof which complex with metals.

Yet another aspect of the invention is to provide a method for complexing metals, including contacting a solution containing the metals with a mixture of exopolysaccharide, homogentisic melanin and precursors thereof.

BRIEF DESCRIPTION OF THE DRAWINGS

FIG. 2(A), (B) and (C) show the nucleotide sequence for approximately 1.4 kb of the HincII fragment in pMC3A. The translated amino acid sequence of the melA gene product is indicated and is found at nucleotides 316 to 1425.

FIG. 14 is the DNA sequence and predicted amino acid sequence of melA. This figure depicts 720 nucleotides of sequence obtained downstream of melA. The asterisks at the top of the sequence denote each interval of ten nucleotides. Stippling identifies the putative translational start site for mlgA, and the termination codon is indicated under the sequence.

FIG. 22 shows a comparison of the amino acid sequence of MelA, the product of the melA gene in S. colwelliana D against the amino acid sequence of Pseudomonas pHPPH. The comparison was performed by the BestFit subprogram of the GCG software package. Residues connected by a vertical line are identical; residues connected by dots are similar. Residue numbering is relative to the open reading frame of MelA.

DETAILED DESCRIPTION OF THE INVENTION

Figure 1:
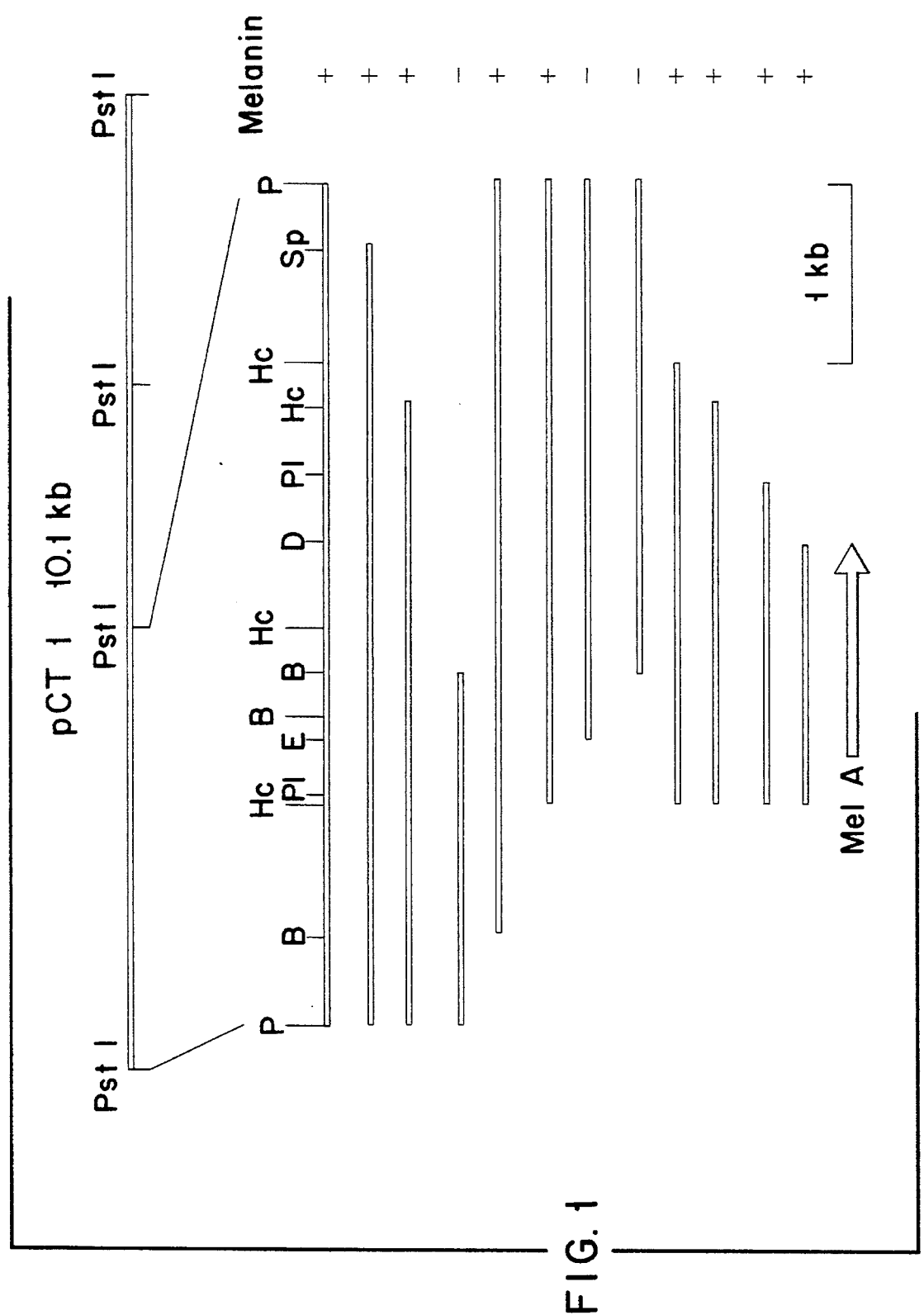
FIG. 1 depicts a restriction map of the 10.5-kb PstI insert in pCT and deletion analysis of pDC1, a plasmid containing a 4.2-kb PstI DNA fragment capable of directing melanin synthesis. The solid lines indicate the DNA fragment present each deletion subclone. The ability of subclones to direct melanin synthesis is indicated with (+), melanin produced, or (−), no melanin produced. Abbreviations: B, BglII; D, DraIII; E, EcoRI; H or Hc HincII; P, PstI; Pl, PleI, S; SmaI; Sp, SphI.

The present invention is directed to a marine melA gene, from the genus Shewanella. S. colwelliana synthesizes a tyrosinase, melB, and a p-hydroxyphenylpyruvate hydroxylase, melA. The melA gene has been cloned, sequenced and found to encode a unique enzyme that alone mediates melanogenesis via an intermediate, Tyr-P which has recently been identified as homogentisic acid (HGA). HGA has commercial uses in dye compositions and as a metal chelator.

In particular, this gene is provided as an isolated nucleic acid from the Shewanella species of S. colwelliana or derivative strain thereof, preferably from S. colwelliana strain D, and most preferably strain DYF. The isolated nucleic acid may be provided as a DNA, a cDNA, an RNA, an mRNA or a recombinant DNA.

To clone a Shewanella melA gene, chromosomal DNA from a culture of a Shewanella strain is isolated and subjected to partial digestion with one or more restriction enzymes, usually one. The partially digested DNA is then fractionated on an agarose gel (or by other suitable means, e.g., gel chromatography) and the desired size fragments are eluted from the gel, cloned into a suitable cloning vector, transformed into a host compatible with the selected vector, which host also does not exhibit melanin pigmentation, and plated on selective media to identify dark brown or brown-black colonies containing and expressing the desired melA clone. Once a clone is identified, it can be restriction mapped, sequenced and the coding region determined, for example, by deletion analysis, comparison to other melA genes, protein sequencing, etc. These procedures are suitable for cloning the melA gene from a cultured strain of any Shewanella species. In general, the procedures for isolating DNA, subjecting it to partial digestion, isolating DNA fragments, ligating the fragments into a cloning vector, and transforming a host are well known in recombinant DNA technology. Accordingly, one of ordinary skill in the art can use or adapt the detailed protocols for such procedures as found in Sambrook et al. (1989), Molecular Cloning: A Laboratory Manual, 2nd. Ed., Cold Spring Harbor Laboratory, Cold Spring Harbor, N.Y., 3 volumes, or in any of the myriad of manuals on recombinant DNA technology.

Specifically, since E. coli does not normally pigment, it is an ideal host for "expression" cloning of the melA gene. For E. coli, pigmented colonies are selected by visual inspection of colonies grown on rich agar, e.g., L broth, supplemented with tyrosine and copper. In other hosts, pigmentation (or lack of pigmentation) can be determined by visual inspection of cells or colonies growing on selective media.

When using E. coli as the host, an enormous number of cloning vectors are available including pBR322, pBR322- based and related plasmids, bacteriophages and cosmids. The restriction enzyme used for partial digestion should preferably generate a sticky end compatible with a cloning site in the selected vector and not cut in the melA gene. Restriction enzymes which generate blunt-ended fragments can also be used. If compatible ends are not generated or particular restriction sites are desired, linkers may be added to generate the desired compatible restriction site. Linkers are added either to existing sticky-ended fragments, existing blunt-ended fragments or to sticky ends made blunt by appropriate filling reactions.

Because the restriction sites present in the melA gene prior to cloning and analyzing the gene are unknown, a partial enzymatic digestion is performed to ensure production of a large DNA fragment encoding the entire gene. The partial digestion can be repeated one or more times with different enzymes, if difficulties arise in obtaining the necessary fragment. If large enough DNA fragments (10–40 kb) are isolated, there will be a strong probability that a fragment containing the whole melA gene is present in the collection of isolated fragments, especially if two or more partial digests are prepared. In practice, a single partial digestion has generally been sufficient to obtain the desired clone.

The species of the genus Shewanella from which a marine melA gene can be cloned is preferably *S. colwelliana*, however, the gene can also be cloned from other genera including *Vibrio cholera, Hyphomonas, Pseudomonas* and the like. The especially preferred species is *S. colwelliana*. Particular strains of these species which can be cultured to obtain chromosomal DNA include, but are not limited to, *S. colwelliana* strains LST, DYF and HYP accorded ATCC accession numbers 39565, 33887 and 33888, respectively.

The *S. colwelliana* strains, LST, DYF and HYP have been described, including growth conditions therefor, in U.S. Pat. No. 4,740,466 which is incorporated herein by reference. The various strains from the other *Shewanella* species can also be grown as described for *S. colwelliana* or other known conditions.

The melA gene from any species of the genus Shewanella may be isolated as described above, however, as an alternative, once one melA gene has been obtained, it can serve as a hybridization probe to isolate corresponding melA genes from the other Shewanella species by cross-hybridization under low to moderate stringency conditions. Such conditions are usually found empirically by determining the conditions wherein the probe specifically cross-hybridizes to its counterpart melA gene with a minimum of background hybridization. Nucleic acid hybridization is a well known technique and thoroughly detailed in Sambrook et al.

Figure 4:
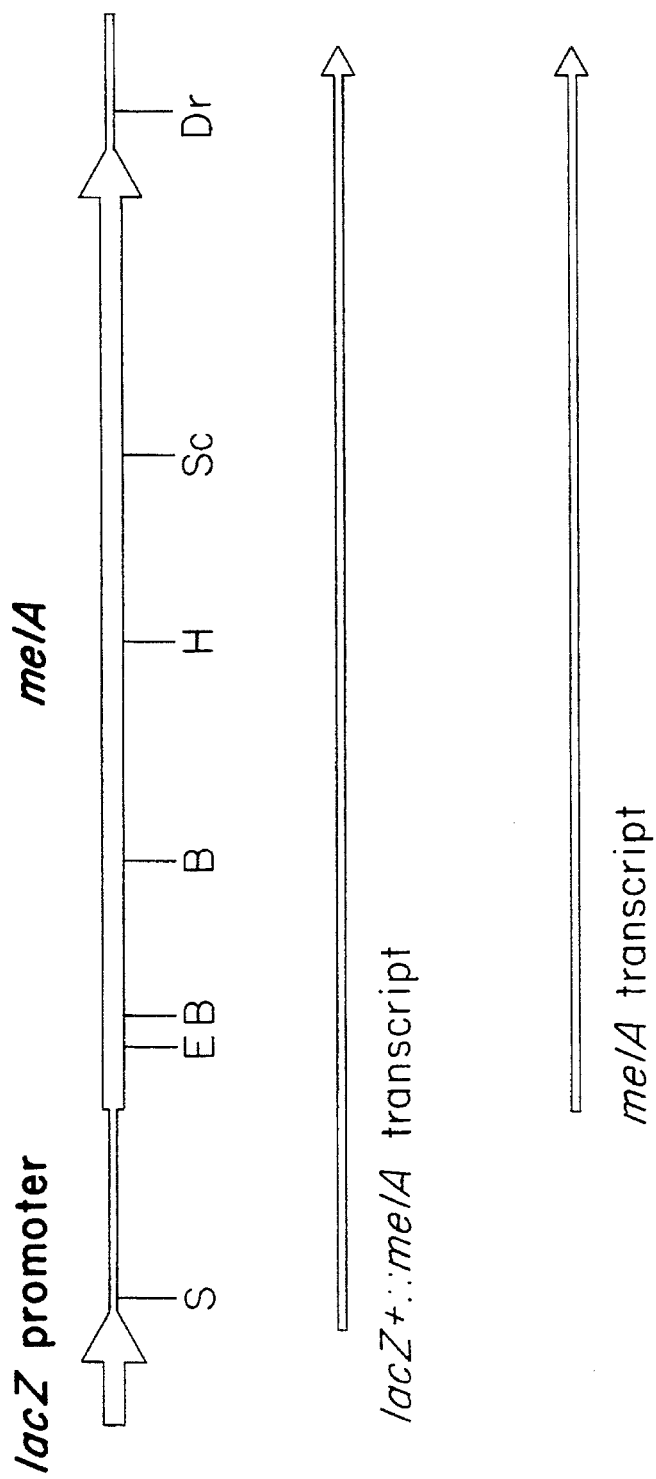
FIG. 4 depicts the pertinent region of the overexpression plasmid pMC3B designed to overproduce *S. colwelliana* MelA. Abbreviations are the same as FIG. 1.

The *S. colwelliana* melA gene was cloned by the isolating chromosomal DNA from *S. colwelliana* strain LSTDYF, performing a partial digestion with PstI, isolating approximately 35 kb DNA fragments from an agarose gel and ligating them into the cosmid vector pHC79. The constructs were packaged in vitro into phage lambda heads and transduced into *E. coli* recipients. Transductants were transferred onto tyrosinase screening media consisting of L broth supplemented with 5 mg/ml tyrosine and 5 µg/ml copper and screened for pigmentation properties, i.e., for the appearance of dark brown or brown-black colonies. A single positive clone (out of 600) was selected for analysis by restriction mapping, deletion analysis and sequencing. The nucleotide sequence and translated amino acid sequence for the *S. colwelliana* melA gene is shown below (or is shown in FIG. 4 (SEQ ID NO 1)):

```
           10          20          30          40
            |           |           |           |
        TGA CTT TAT GAG TCG CAC AGG TAT CGA AGC GGG CTA CAT GAC CTT 50          60          70          80          90
        |           |           |           |           |
    ACA TCA AAA AGG CGT GCC GCA TGG ACC ACA ACC TGG TCG TAC TGA 100         110         120         130
               |           |           |           |
           AGC CTC AGT GGG CAA AAC TGA AAC CTA TGA GTA TGC AGT AAT GGT 140         150         160         170         180
        |           |           |           |           |
    GGA CAC CTT TGC ACC ACT GCA ACT GAC CCA GCA TGT CAA TCG TGC 190         200         210         220
                 |           |           |           |
             ATG AGC AAA GAT TAC AAC CGT TCC TGG CTA GAA GAG TAA AAG CGT 230         240         250         260         270
        |           |           |           |           |
    TCA GCC AGT GCT GAA CAT CTA ATA AAT ATA ACA CCA GAG GTG ACA 280         290         300         310
            |           |           |           |
        CCG AAG AGT GCC CTT GGT TGC AAT AAG TTG AAA GAG GAT AAT TAC 320         330         340         350         360
        |           |           |           |           |
    ATG GCA AGC GAA CAA AAC CCA CTG GGT CTA CTT GGT ATC GAA TTC
    Met Ala Ser Glu Gln Asn Pro Leu Gly Leu Leu Gly Ile Glu Phe 370         380         390         400
               |           |           |           |
           ACT GAA TTT GCT ACA CCA GAT CTA GAT TTT ATG CAT AAA GTT TTT
           Thr Glu Phe Ala Thr Pro Asp Leu Asp Phe Met His Lys Val Phe
```

-continued

```
     410         420         430         440         450
      |           |           |           |           |
ATC GAC TTT GGT TTC TCA AAA CTT AAA AAA CAC AAG CAG AAA GAT
Ile Asp Phe Gly Phe Ser Lys Leu Lys Lys His Lys Gln Lys Asp 460         470         480         490
            |           |           |           |
ATT GTT TAC TAT AAA CAA AAT GAT ATT AAC TTT TTA CTC AAC AAT
Ile Val Tyr Tyr Lys Gln Asn Asp Ile Asn Phe Leu Leu Asn Asn 500         510         520         530         540
      |           |           |           |           |
GAA AAA CAG GGC TTT TCA GCC CAG TTT GCC AAA ACG CAT GGC CCA
Glu Lys Gln Gly Phe Ser Ala Gln Phe Ala Lys Thr His Gly Pro 550         560         570         580
            |           |           |           |
GCC ATT AGT TCT ATG GGC TGG CGT GTA GAA GAT GCC AAC TTT GCC
Ala Ile Ser Ser Met Gly Trp Arg Val Glu Asp Ala Asn Phe Ala 590         600         610         620         630
      |           |           |           |           |
TTT GAA GGT GCT GTA GCC CGT GGG GCT AAA CCC GCA GCA GAT GAG
Phe Glu Gly Ala Val Ala Arg Gly Ala Lys Pro Ala Ala Asp Glu 640         650         660         670
            |           |           |           |
GTG AAA GAT CTT CCC TAT CCC GCT ATC TAT GGC ATT GGT GAC AGC
Val Lys Asp Leu Pro Tyr Pro Ala Ile Tyr Gly Ile Gly Asp Ser 680         690         700         710         720
      |           |           |           |           |
CTT ATC TAC TTT ATC GAT ACG TTT GGC GAT GAC AAC AAT ATC TAC
Leu Ile Tyr Phe Ile Asp Thr Phe Gly Asp Asp Asn Asn Ile Tyr 730         740         750         760
            |           |           |           |
ATC TCT GAT TTT GAA GCG TTA GAT GAG CCT ATC ATC ACC CAA GAG
Thr Ser Asp Phe Glu Ala Leu Asp Glu Pro Ile Ile Thr Gln Glu 770         780         790         800         810
      |           |           |           |           |
AAA GGC TTC ATT GAG GTC GAC CAT CTC ACC AAT AAT GTC CAT AAG
Lys Gly Phe Ile Glu Val Asp His Leu Thr Asn Asn Val His Lys 820         830         840         850
            |           |           |           |
GGC ACC ATG GAA TAT TGG TCA AAC TTC TAC AAA GAC ATT TTT GGC
Gly Thr Met Glu Tyr Trp Ser Asn Phe Tyr Lys Asp Ile Phe Gly 860         870         880         890         900
      |           |           |           |           |
TTT ACA GAA GTG CGT TAC TTC GAC ATT AAG GGC TCA CAA ACA GCT
Phe Thr Glu Val Arg Tyr Phe Asp Ile Lys Gly Ser Gln Thr Ala 910         920         930         940
            |           |           |           |
CTT ATC TCT TAC GCC CTG CGC TCG CCA GAT GGT AGT TTC TGC ATT
Leu Ile Ser Tyr Ala Leu Arg Ser Pro Asp Gly Ser Phe Cys Ile 950         960         970         980         990
      |           |           |           |           |
CCA ATT AAC GAA GGC AAA GGC GAT GAT CGT AAC CAA ATT GAT GAG
Pro Ile Asn Glu Gly Lys Gly Asp Asp Arg Asn Gln Ile Asp Glu 1000        1010        1020        1030
            |           |           |           |
TAC TTA AAA GAG TAC GAT GGC CCA GGT GTC CAA CAC TTA GCG TTC
Tyr Leu Lys Glu Tyr Asp Gly Pro Gly Val Gln His Leu Ala Phe 1040        1050        1060        1070        1080
            |           |           |           |           |
CGT AGC CGC GAC ATA GTT GCC TCA CTG GAT GCC ATG GAA GGA AGC
Arg Ser Arg Asp Ile Val Ala Ser Leu Asp Ala Met Glu Gly Ser 1090        1100        1110        1120
            |           |           |           |
TCC ATT CAA ACC TTG GAC ATA ATT CCA GAG TAT TAC GAC ACT ATC
Ser Ile Gln Thr Leu Asp Ile Ile Pro Glu Tyr Tyr Asp Thr Ile
```

-continued

```
        1130             1140            1150             1160            1170
         |                |               |                |               |
TTT GAA AAG CTG CCT CAA GTC ACT GAA GAC AGA GAT CGC ATC AAG
Phe Glu Lys Leu Pro Gln Val Thr Glu Asp Arg Asp Arg Ile Lys 1180             1190            1200             1210
         |                |               |                |
CAT CAT CAA ATC CTG GTA GAT GGC GAT GAA GAT GGC TAC TTA CTG
His His Gln Ile Leu Val Asp Gly Asp Glu Asp Gly Tyr Leu Leu 1220             1230            1240             1250            1260
         |                |               |                |               |
CAA ATT TTC ACC AAA AAT CTA TTT GGT CCA ATT TTT ATC GAA ATC
Gln Ile Phe Thr Lys Asn Leu Phe Gly Pro Ile Phe Ile Glu Ile 1270             1280            1290             1300
         |                |               |                |
ATC CAG CGT AAA AAC AAT CTC GGT TTT GGC GAA GGT AAT TTT AAA
Ile Gln Arg Lys Asn Asn Leu Gly Phe Gly Glu Gly Asn Phe Lys 1310             1320            1330             1340            1350
         |                |               |                |               |
GCC CTA TTT GAA TCG ATT GAG CGT GAT CAG GTG CGT CGC GGC GTA
Ala Leu Phe Glu Ser Ile Glu Arg Asp Gln Val Arg Arg Gly Val 1360             1370            1380             1390
         |                |               |                |
CTC TAA CAA TCA CCC AGT GAT CCA ACC TCA AAA AAC CAG CAT CGC
Leu End 1400             1410            1420             1430
         |                |               |                |
GCT GGT TTT TTT ATT GCA GCA CAA CAA TAA ACC TCT ACA C
```

A further aspect of the present invention provides the nucleic acids encoding the subject melA genes in replicable expression vectors and transformed hosts containing these vectors. The replicable expression vectors may be used to obtain the polypeptides of the present invention by well known methods in recombinant DNA technology.

The instant replicable expression vectors comprise a nucleic acid encoding the subject melA gene, i.e., the melA coding sequence is operably linked to a nucleotide sequence element capable of effecting expression of the MelA. In particular, the nucleotide sequence elements can include a promoter, a transcription enhancer element, a termination signal, a translation signal, or a combination of two or more of these elements, generally including at least a promoter element.

Replicable expression vectors are generally DNA molecules engineered for controlled expression of a desired gene, especially where it is desirable to produce large quantities of a particular gene product, or polypeptide. The vectors comprise one or more nucleotide sequences operably linked to a gene to control expression of that gene, the gene being expressed, and an origin of replication which is operable in the contemplated host. Preferably the vector encodes a selectable marker, for example, antibiotic resistance. Replicable expression vectors can be plasmids, bacteriophages, cosmids and viruses. Any expression vector comprising RNA is also contemplated.

The replicable expression vectors of this invention can express MelA at high levels. These vectors may be derived from a prokaryotic source or a eukaryotic source but are preferably derived from a prokaryote or lower eukaryote, e.g., yeast or fungi.

Prokaryotic vectors include bacterial plasmids and bacteriophage vectors that can transform such hosts as *E. coli, B. subtilis, Streptomyces* sps. and other microorganisms. Many of these vectors are based on pBR322, M13 and lambda and are well known in the art and employ such promoters as trp, lac, $P_L$, T7 polymerase and the like. Likewise, suitable eukaryotic vectors that function in tissue culture are especially useful, with yeast vectors being contemplated. These vectors include yeast plasmids and minichromosomes, retrovirus vectors, bovine papilloma virus (BPV) vectors, baculovirus vectors, SV40-based vectors and other viral vectors. The cultured cells which serve as the transformed hosts to these vectors are well known in the art and a suitable host for a particular vector can be readily selected by one of ordinary skill in the art. Numerous texts on recombinant DNA techniques are available which describe expression vectors, the control sequences contained therein, and general methodology for making expression constructs. Hence, one skilled in the art has available many choices of replicable expression vectors, compatible hosts, and well-known methods for making and using the vectors.

Another aspect of this invention provides a homogeneous melA protein from the genus Shewanella, and especially as provided by the subject melA genes. Moreover, peptides and fragments as well as chemically modified derivatives of this protein are also contemplated.

Purification of the subject MelA proteins from natural or recombinant sources can be accomplished by conventional purification means such as ammonium sulfate precipitation, preferably in the 10–35% fraction, gel filtration chromatography, such as with a Biogel P-100 column, ion exchange chromatography, adsorption chromatography, affinity chromatography, chromatofocusing, HPLC, FPLC as a protein from 39.5 to 42 kD, Rotophor preparative focusing where the protein is predicted to run at 4.4, but runs at approximately 4.6, gel electrophoresis, where the proteins is predicted to run at 39.5 kD but actually runs at about 42.0 kD, and the like. Where appropriate purification steps can be done in batch or in columns. Fractions containing the MelA are identified by production of an enzymatic product, Tyr-P, now identified as homogentisic acid.

Peptide fragments can be prepared by proteolysis or by chemical degradation. Typical proteolytic enzymes are trypsin, chymotrypsin, V8 protease, subtilisin and the like; the enzymes are commercially available, and protocols for performing proteolytic digests are well known. Peptide fragments are purified by conventional means, as described above. Peptide fragments can often be identified by amino acid composition or sequence. Peptide fragments are useful as immunogens to obtain antibodies against the subject marine MelA.

The present invention relates to antibodies to marine MelA from the genus Shewanella and the species described herein. In a preferred embodiment the antibodies are directed to Shewanella MelA, especially produced by *S. colwelliana*. Such antibodies may be monoclonal or polyclonal and are contemplated to be useful in developing detection assays (immunoassays) for marine MelA proteins, monitoring marine MelA and in purifying marine MelA. Thus, in accordance with this invention, an antibody to a marine MelA encompasses monoclonal or polyclonal antibodies to said MelA, especially a marine MelA from the genus Shewanella, or to antigenic parts thereof.

Both polyclonal and monoclonal antibodies to marine MelA are obtainable by immunization of an animal with purified MelA, purified recombinant MelA, fragments of these proteins, or purified fusion proteins of MelA with another protein. In the case of monoclonal antibodies, partially purified proteins or fragments may serve as immunogens. The methods of obtaining both types of antibodies are well known in the art with excellent protocols for antibody production being found in Harlow et al. (1988) *Antibodies: A Laboratory Manual*, Cold Spring Harbor Laboratory, Cold Spring Harbor, N.Y., 726 pp.

Polyclonal sera are relatively easily prepared by injection of a suitable laboratory animal with an effective amount of the purified MelA, or parts thereof, collecting serum from the animal, and isolating specific sera by any of the known immunoadsorbent techniques. Antibodies produced by this method are useful in virtually any type of immunoassay.

Monoclonal antibodies are particularly useful because they can be produced in large quantities and with a high degree of homogeneity. Hybridoma cell lines which produce monoclonal antibodies are prepared by fusing an immortal cell line with lymphocytes sensitized against the immunogenic preparation and is done by techniques which are well known to those who are skilled in the art. (See, for example, Douillard, I. Y. and Hoffman, T., "Basic Facts About Hybridomas" in *Compendium of Immunology*, Vol II, L. Schwartz (Ed.) (1981); Kohler, G. and Milstein, C., *Nature* 256:495–497 (1975) and *European Journal of Immunology* 6: 511–519 (1976); Harlow et al.; Koprowski, et al., U.S. Pat. No. 4,172,124; Koprowski et al., U.S. Pat. No. 4,196, 265 and Wands, U.S. Pat. No. 4,271,145, the teachings of which are herein incorporated by reference.)

The presence of a marine MelA contemplated herein in a sample, such as a culture supernatant and the like, aquatic animals, in a microorganism, or in any other source suspected to contain the marine MelA, such as a microfouling film or a component of a mariculture operation, can be detected utilizing antibodies prepared as above, either monoclonal or polyclonal, in virtually any type of immunoassay. Likewise, the present antibodies can be used to identify marine microorganisms which have or produce MelA. Accordingly, the present invention provides a method of detecting a marine MelA by the steps of contacting a sample suspected of containing said MelA with an antibody of the invention for a time and under conditions sufficient to form a MelA-antibody complex and subjecting this complex to a detecting means. As well known to one skilled in the art, the time and conditions for immunodetection assays are variable and depend on the particular assay.

A wide range of detection techniques and conditions are available to one skilled in the art as can be seen by reference to U.S. Pat. Nos. 4,016,043, 4,424,279 and 4,018,653 and to Harlow et al. which provides extensive protocols for immunodetection of molecules. These techniques, of course, include both single-site and two-site, or "sandwich" assays, assays of the non-competitive types as well as competitive binding assays, ELISA, radioimmunoassays, immunoprecipitation and immunoblotting (Western blotting). Sandwich assays are commonly used, a number of variations of the technique exist, and all are intended to be encompassed by the present invention.

Direct and indirect immunoassays, i.e., ELISA, immunoblotting and the like, may employ reporter molecules linked to either a primary antibody (direct assay) or a second antibody or antibody-specific protein such as Protein A or Protein G (indirect assay). The primary antibody can be an antibody of the subject invention labelled with the desired reporter molecule.

By "reporter molecule," as used herein, is meant a molecule which, by its chemical nature, provides an identifiable signal to detect antigen-antibody complexes. Detection may be either qualitative or quantitative. The most commonly used reporter molecules are either enzymes, fluorophores, or radionuclide containing molecules (i.e., radioisotopes). In the case of an enzyme immunoassay, an enzyme is conjugated to the antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase, and alkaline phosphatase among others. The substrate to be used with a particular enzyme is generally chosen for the production of a detectable color change upon reaction. For example, p-nitrophenyl phosphate is suitable for use with alkaline phosphatase conjugates; for peroxidase conjugates, 1,2-phenylenediamine, 5-aminosalicyclic acid, or tolidine are commonly used. It is also possible to employ fluorogenic substrates, which yield a fluorescent product rather than the chromogenic substrates noted above. After binding an enzyme-labeled antibody to an antigen or antigen-antibody complex, as appropriate, the excess labeled antibody is washed away, and a solution containing the appropriate substrate is added. The substrate reacts with the enzyme, i.e., the reporter molecule, to give a qualitative visual signal or a quantitative signal which can be assessed to indicate the amount of antigen present in the sample.

Alternatively, fluorescent compounds, such as fluorescein and rhodamine, may be chemically coupled to antibodies without altering their binding capacity. As used in immunofluorescence, when activated by illumination with light of a specific wavelength, a fluorophore-labeled antibody absorbs the light energy, inducing the fluorophore into an excited stated which is followed by emission of light having a characteristic wavelength. Generally, the emitted light is a characteristic color in the visible range and is detectable with a light microscope equipped for immunofluorescence. Fluorescent antibodies are used in sandwich assays, direct and indirect immunoassays as described above, except after washing, the immune complex is exposed to light of the appropriate wavelength, and the fluorescence is observed. Immunofluorescence and enzyme-based immunoassay techniques are both well established in the art and are particularly preferred. However, other reporter molecules, such as radioisotopes, chemiluminescent or bioluminescent molecules, may also be employed. It will be readily apparent to the skilled technician how to vary the procedure to suit the required purpose.

Another aspect of the invention provides a means of purifying a marine MelA of the genus Shewanella by affinity selection. This method involves contacting a sample containing the MelA with an antibody of the invention, and separating the antigen-antibody complex, e.g., the MelA-antibody complex from the remainder of the sample and recovering the MelA in a form free from the antibody. Typically the complex-containing sample is fractionated and the fraction(s) containing MelA are identified by a convenient biochemical, enzymatic, immunological or other detection means. To facilitate fractionation, the subject antibodies can be bound to a chromatography resin before or after binding to the MelA. This method can yield purified MelA in large amounts and in pure form.

Accordingly, the present invention is also directed to a kit for the rapid and convenient assay of a marine MelA, especially from Shewanella sps., in samples suspected of containing marine MelA. The kit is compartmentalized to receive a first container adapted to contain a molecule capable of detecting the antibody of the first container, wherein the molecule is Protein A, Protein G, an antibody against the antibody of the first container, or a second antibody against said MelA or to an antigenic component thereof, said molecule being labeled with a reporter molecule capable of giving a detectable signal as hereinbefore described. If the reporter molecule is an enzyme, then a third container adapted to contain a substrate for said enzyme is provided. In an exemplified use of the subject kit, a sample to be tested for a marine MelA is contacted with the contents of the first container for a time and under conditions for the MelA, if present, to bind to the antibodies in the first container. The time and conditions are determined by the particular immunoassay which is employed as described herein. After removal of unbound material (e.g., by washing with sterile phosphate buffered saline) the contents of the second container is contacted with the sample being tested. If the MelA has bound to the antibodies of the first container, the detecting molecule of the second container will bind to the secondary complex to form a tertiary complex, and since said the detecting molecule is labeled with a reporter molecule, when subjected to a detecting means, the tertiary complex is detected.

Another aspect of the present invention is directed to a method of detecting the subject marine MelA by nucleic acid hybridization techniques such as Southern blotting, Northern blotting and the like, or by the polymerase chain reaction (PCR). Accordingly, a method of detecting a marine MelA from the genus Shewanella is provided which comprises contacting a sample suspected of containing said melA with a first nucleic acid sufficiently complementary to hybridize to a second nucleic acid which encodes said MelA in said sample for a time and under conditions sufficient to effect said hybridization and thereby form a complex of said first and second nucleic acids and subjecting said complex to a detecting means. In this method, the first nucleic acid may have a reporter group attached thereto. Reporter groups can include radioisotopes, enzymatically detected groups such as biotin or fluorophores such as rhodamine and fluorescein. Detailed methods for hybridization and blotting are found in Sambrook et al.

For PCR, the present method of detecting a marine melA gene from the genus Shewanella comprises subjecting a sample suspected of containing said melA to a polymerase chain reaction (PCR) using at least two oligonucleotide primers sufficiently complementary to hybridize to a nucleic acid in said sample which encodes said MelA, and thereby producing at least one amplified melA nucleic acid segment and identifying said segment. PCR has been described in U.S. Pat. Nos. 4,683,195, 4,683,202, and 4,800,159 which are incorporated herein by reference as well as described extensively in the literature, see for example Saiki et al. (1988), *Science* 239: 487–491. The segment may be detected by gel electrophoresis or blotting, for example.

In the above PCR and hybridization methods, the sample in which the melA gene is to be detected may be a microorganism, a culture of microorganisms, a culture supernatant, a cell extract, seawater, a microfouling film, a component of a mariculture operation and the like.

This invention further provides a method of inducing larval oyster settlement which comprises exposing oyster larvae to a transformed microorganism or cell, in an aqueous environment wherein the microorganism or cell is expressing an active marine MelA from the genus Shewanella and thereby producing metabolites which induce said oyster settlement. MelA induces cementation in biofilms, and the other melanogenic gene in the bacterium, MelB, synthesizes DOPA which induces oyster search behavior.

In one particular embodiment of this invention, each of the transformed microorganisms, cells or their variants can be employed in a process for inducing the settlement and metamorphosis of *Crassostrea virginica* larvae. The Shewanella strain D may also be used alone. Accordingly, the transformants are cultured in a growth medium and provided with a suitable surface material to which they can affix due to the production of an acid polysaccharide exopolymer. Oyster larvae are simultaneously or thereafter exposed to the transformants or, alternatively, to their melanin or melanin precursor metabolic products including melanin, pheomelanin, DOPA, or mixtures thereof for a time and under conditions to effect larvae setting. Once settlement occurs, metamorphosis, i.e., maturation of the oyster larvae, naturally progresses in response to the micro-colonies of transformants which can develop on the provided surface material. Oyster larvae settlement may be induced by a combination of microorganisms such as the subject transformants and a *Shewanella species*, e.g., *S. colwelliana*, preferably strain D.

This invention also relates to a method of improving adhesion of an exopolysaccharide comprising contacting said exopolysaccharide with a marine MelA from the genus Shewanella for a time and under conditions sufficient to impart greater adhesibility of said exopolysaccharide. For example, a purified preparation of exopolysaccharide or exopolysaccharide with altered and useful metal binding properties, especially purified polysaccharide adhesive viscous exopolymer (PAVE) from a marine microorganism, is contacted with a solution or other preparation containing the MelA until the desired viscosity is effected.

A marine melA gene from the genus Shewanella may readily serve as a selectable, phenotypic marker for cloning experiments because its expression imparts an easily recognized phenotype, darkly pigmented colonies. Cloning via insertional inactivation of melA results in loss of pigmentation. Accordingly, this invention provides the subject melA genes as selectable markers for prokaryotes and eukaryotes, preferably for prokaryotes and lower eukaryotes such as yeast and fungi. melA is efficiently expressed in Gram-negative bacteria from its own promoter, and can be used, therefore, under control of its own promoter in most prokaryotic organisms employed as cloning hosts.

Moreover, it is straightforward to determine whether the melA promoter functions in other prokaryotes or eukaryotes by a simple screening test (see below for details), allowing one skilled in the art to adapt the melA gene to different systems. If it is found that melA is not expressed in a particular host, then the gene is placed under control of another promoter capable of directing transcription in that host. Juxtaposition of the melA coding sequence with an appropriate promoter, preferably a constitutive promoter, is accomplished by standard recombinant DNA techniques, e.g., using convenient restriction sites, if available, or introducing needed sequences and sites via linkers, large oligonucleotides or by site-directed mutagenesis.

Insertional inactivation as used herein is disruption of gene expression by insertion of a DNA fragment into a gene present on a cloning vector. In general, the DNA fragment is inserted into the coding sequence of the gene product so that no functional gene product will be translated; however, transcriptional disruption also leads to loss of gene expression so that the DNA fragment could be inserted into the promoter or other upstream sequences required for gene expression. Thus, a selectable marker for insertional inactivation must have at least one unique restriction site, into which a DNA fragment can be inserted and that creates a concomitant loss of marker phenotype. It is advantageous though not absolutely essential that the restriction site be unique with respect to the cloning vector containing the selectable marker. For the melA gene this can be an existing restriction site, e.g., ScaI at nucleotide 989, or can be a genetically-engineered restriction site prepared by known methods such as site-directed mutagenesis. Unique restriction sites can generally be introduced into the coding sequence of a gene without changing amino acid sequence (because of degeneracy in the genetic code) or with a minor sequence change that does not effect activity. Cloning vectors can be constructed which contain melA alone or with one or more other selectable markers, typically one, such as genes encoding drug resistance, nutritional requirements or other selectable phenotype.

Detection of pigmentation (or loss of pigmentation) is simple and inexpensive, merely requiring visual inspection of colonies grown on a rich medium supplemented with tyrosine and copper. Pigmented colonies appear as dark brown-black or brown colonies, whereas unpigmented colonies have a normal appearance, for example, a creamy-whitish color for *E. coli* and many other microorganisms, yeast, and cultured cells.

The Examples serve to further illustrate the invention.

EXAMPLE 1

Materials and Methods

A. Media: Selection medium for isolating melA positive clones in *E. coli* consisted of L broth agar supplemented with 5 mg/ml tyrosine and 5 µg/ml copper. *Shewanella* sps. were maintained on marine agar 2216 (Difco).

B. Recombinant DNA Techniques: Standard protocols for DNA cloning and analysis were employed (Sambrook et al.). Restriction enzymes, ligase and other enzymes were used according to manufacturer's instructions.

EXAMPLE 2

Cloning of the *S. colwelliana* melA gene

*S. colwelliana* LST chromosomal DNA was partially digested with the restriction endonuclease PstI and fragments of approximately 35 kb were isolated. These fragments were annealed into the cosmid vector pHC79 which were packaged in vitro into phage lambda heads and transduced into *E. coli* recipients. Transductants were screened for MelA activity by assessing pigment properties. Out of 600 transductants, one clone was isolated which exhibited heavy pigment production, similar to pigment production in *S. colwelliana*. This clone was designated pCT and a 4.2-kb PstI fragment was subcloned into pUC19 to generate plasmid pDC1. To verify that the insert in clone pCT derived from *S. colwelliana* DNA, chromosomal *S. colwelliana* DNA was extracted from the cells and analyzed by Southern blotting using pDC1 or the pDC1 *S. colwelliana* insert as the hybridization probe.

The DNA insert in pCT encoding the melA gene was determined to be 10.5 kb and a restriction map of the insert was constructed (FIG. 1). Pigment production in pDC1 was not affected when the insert was cloned in either orientation, indicating that expression of the melA gene was initiated from an *S. colwelliana* promoter within the insert.

EXAMPLE 3

Analysis of the *S. colwelliana* melA gene

The 10.5-kb PstI insert was subjected to deletion analysis to localize the region encoding the melanin gene (melA). Specific restriction fragments were deleted and the resulting plasmids were tested for pigment production on agar plates. A 4.2-kb PstI fragment in plasmid pDC1 directed melanin synthesis and was subjected to still further analysis (FIG. 1). One of the smaller restriction fragment directing melanin synthesis was a 1.9-kb HincII fragment from the plasmid designated pMC3A. The location of the melA open reading frame is indicated at the bottom of FIG. 1; FIG. 2 provides the nucleotide sequence of approximately 1.4 kb of the pMC3A HincII fragment and the translated melA amino acid sequence which lies between nucleotide 316 and nucleotide 1425.

To further characterize the gene product encoded by these plasmids, proteins were synthesized using a DNA directed translation system. The *S. colwelliana* MelA has an apparent molecular weight ($M_r$) of 42,000 as determined by SDS-PAGE analysis and a calculated molecular weight of 39,453 daltons. Interruption of the coding sequence at restriction sites which caused loss of pigmentation also caused the loss of this protein.

EXAMPLE 4

Production of MelA Antibodies

Figure 3:
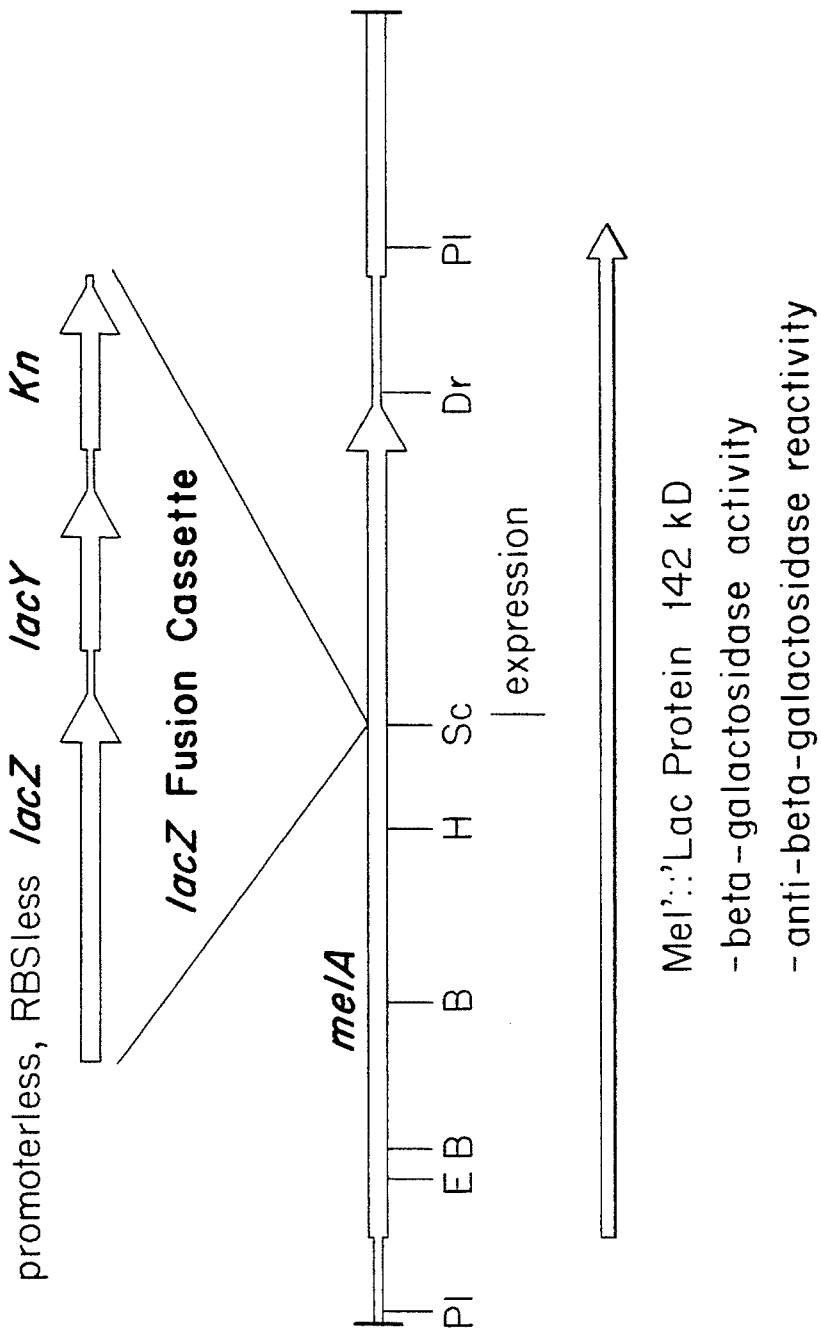
FIG. 3 depicts the pertinent region of the melA'::lacZ protein fusion construct, pMAC3. Abbreviations are the same as FIG. 1.

A melA-lacZ gene fusion was constructed as depicted in FIG. 3 by joining a lacZ fusion cassette to the 3' end of the melA gene to create a 142 kD fusion protein designated Mel'::'Lac.

The plasmids pLKC480–482, contain a lacZY cassette encoded on a single 6.3 kb SmaI restriction fragment. Each cassette is composed of a promoterless, RBS-less lacZ gene truncated for the first 22 bases, an intact lacy gene, and a kanamycin resistance ($KM^R$) marker (163). The plasmids, pLKC480, pLKC481, and pLKC482, when digested with SmaI, release a 6.3 kb fragment, but for each individual construct, the SmaI site is shifted by a single base. Thus, the three SmaI cassettes represent all three possible reading frames, and when inserted in the appropriate orientation into the coding region of a gene, one of the cassettes will result in a functional gene fusion.

Figures 5A, 5B:
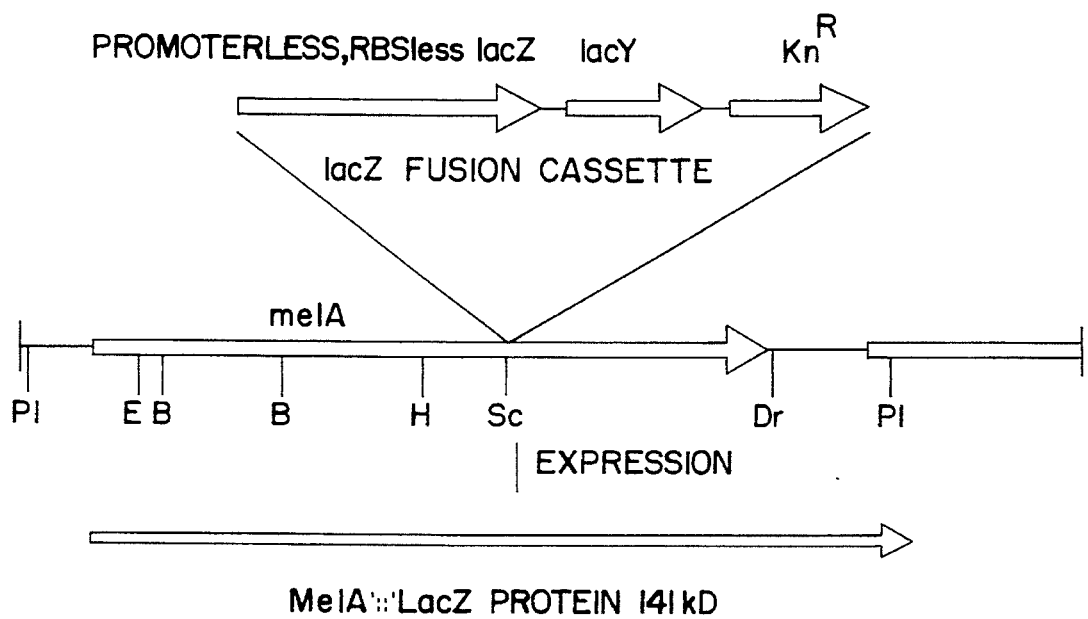
FIG. 5 shows the MelA'-'lacZ fusion construct. (A) The 6.3 kb SmaI fragment of pLKC482 (not to scale) was blunt-end ligated with ScaI-cleaved pMC3A (partial digestion, pUC19 has a single ScaI site), and this ligation mix was transformed into *E. coli* JM101. Transformations were plated on LB agar with Kn, Ap, and X-gal, and Lac+ transformants were isolated for further characterization. The predicted translation product of this fusion construct was 141 kD. (B) The fusion construct pMAC3 was sequenced using a primer specific for the 5' end of the truncated lacZ gene, and the sequence of the fusion junction is shown with the reading frame indicated below the sequence.

The pLKC system was utilized to create melA'::'lacZ gene fusions for several purposes: (i) to verify that the reading frame indicated by sequence analysis of melA was correct; (ii) to generate Lac fusions of MelA for use as a reporter gene; and (iii) to produce a Mel Lac protein fusion to affinity purify. Two separate melA'::'lacZ fusions were generated with the pLKC cassettes. The Mel⁺ pMC3A plasmid was cleaved with BglII, blunt-ended with Klenow fragment, the 258 bp BglII fragment removed, and the large BglII fragment ligated with a SmaI-cleaved, gel-purified fusion cassette. This ligation was used to transform *E. coli* JM101, and the transformants were selected on LB agar containing Km, Ap, and X-gal. Although all three fusion cassettes were ligated to the BglII-cleaved pMC3A in separate reactions, only the pLKC482 cassette resulted in active β-galactosidase fusions as determined by X-gal cleavage. In addition, only cassettes inserted in the left-to-right orientation (relative to the melA sequence, FIG. 5A) resulted in lacZ+ phenotypes. The plasmid encoding this gene fusion was designated pMAC2. The same experiment was conducted with ScaI-cleaved pMC3A. All three fusion cassettes were again ligated with this fragment in separate reactions, and these were plated on the Ap, Km, X-gal-containing LB media (FIG. 5A). Only the ligation with the pLKC482-derived cassette, in the left-to-right orientation resulted in Lac+ transformants. The plasmid encoding the B-galactosidase activity was designated pMAC3.

As a control experiment, the 4.2 kb RI fragment of pMC3A, deleted for 356 bp containing the melA promoter, RBS, and translational start, was ligated with all three pLKC fusion cassettes. None of these constructs, in either orientation, resulted in Lac+ transformants. In addition, pMC3A cleaved and blunt-ended at the DraIII site, just downstream of the predicted translational stop codon, was also ligated to all three SmaI cassettes. Again, none of the constructs in either orientation were Lac+, but all constructs were Mel⁺.

Figure 6:
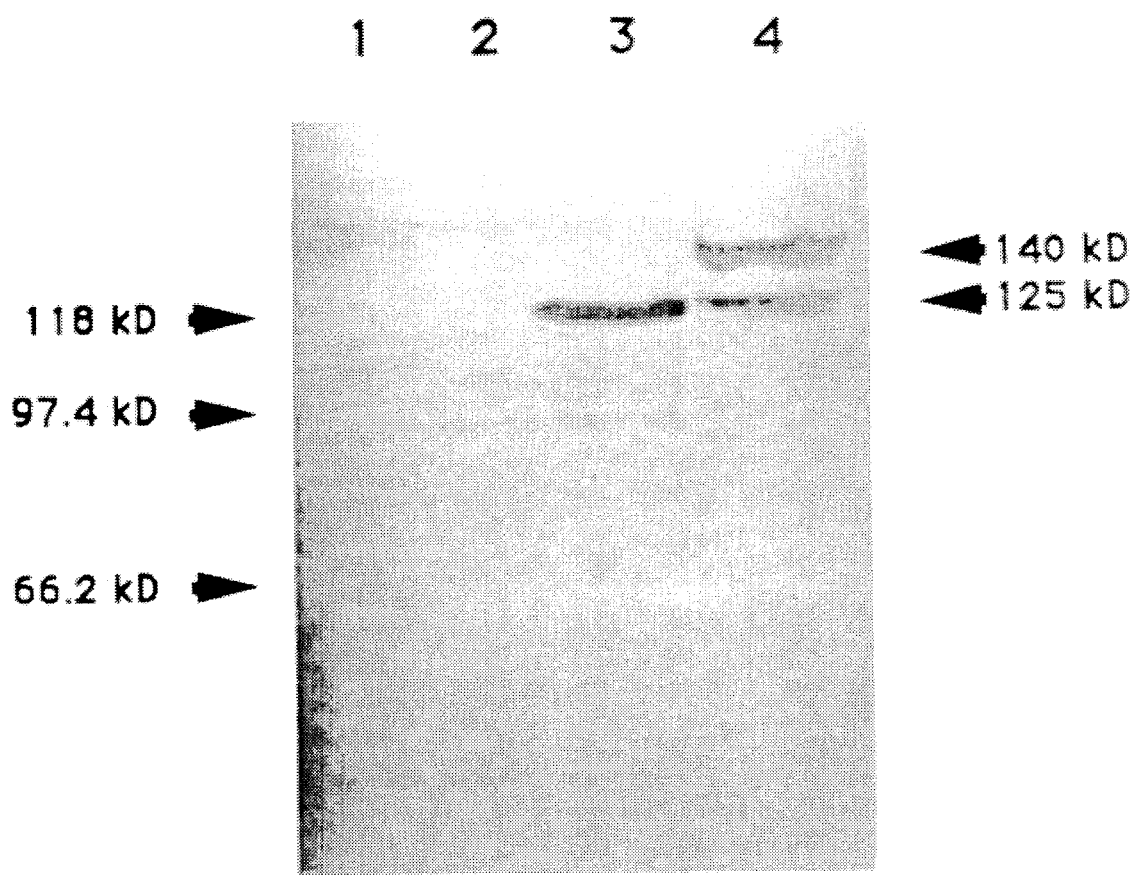
FIG. 6 shows immunostaining of fusion products with monoclonal anti-β-galactosidase. Crude extracts of several *E. coli* AB705 derivatives were electrophoresed on SDS-PAGE (7%), electrotransferred to nitrocellulose, and immunostained with anti-β-galactosidase. The extracts included *E. coli* AB705 (lane 1), and *E. coli* AB705 with PMC3A (lane-2), PMAC2 (lane 3), and PMAC3 (lane 4). Left arrows indicate the mobility of high molecular weight standards and right arrows point out the fusion products.

The pMAC2 and pMAC3 constructs were transformed into *E. coli* AB705, a lac deletion strain, that does not produce any detectable β-galactosidase (the M15 deletion of *E. coli* JM101 synthesizes an inactive β-galactosidase). To verify that the observed X-gal cleavage was due to the activity of the MelA-LacZ fusion protein, extracts of *E. coli* AB705 with pUC19, pMC3A, pMAC2, or pMAC3 plasmids were electrophoresed on SDS-PAGE, electrotransferred to nitrocellulose, and immunostained using monoclonal antibody against *E. coli* β-galactosidase (Promega Biotech, Madison, Wis.). The predicted molecular masses of the fusion proteins encoded by pMAC2 and pMAC3, were 127.7 kD and 141 kD, respectively. The immunoblot revealed that *E. coli* AB705 with or without pMC3A, did not produce any proteins that bound the anti-β-galactosidase antibody (FIG. 6, lanes 1 and 2). In contrast, the pMAC2 extract synthesized a strongly staining protein of approximately 125 kD (FIG. 6, lane 3). The pMAC3 extract synthesized a pair of strongly reactive proteins, a 140 kD and a 125 kD protein (FIG. 6, lane 4). Large β-galactosidase fusion proteins are typically unstable in the area of the fusion junction (157), and this protein probably corresponded to such a breakdown product. Both pMAC2 and pMAC3 also produced several smaller immunoreactive proteins, that probably corresponded to proteolytic cleavage products.

The fusion protein encoded by pMAC3 was selected for use in generating anti-MelA antibodies. The pMAC3 fusion protein is composed of the amino terminal 25.5 kD of melA fused to 115 kD of lacZ. Sequencing of pMAC3 with a primer complementary to the 5' coding region of lacZ verified that the Mela-LacZ fusion protein was expressed in the predicted reading frame (FIG. 5B).

Figure 7:
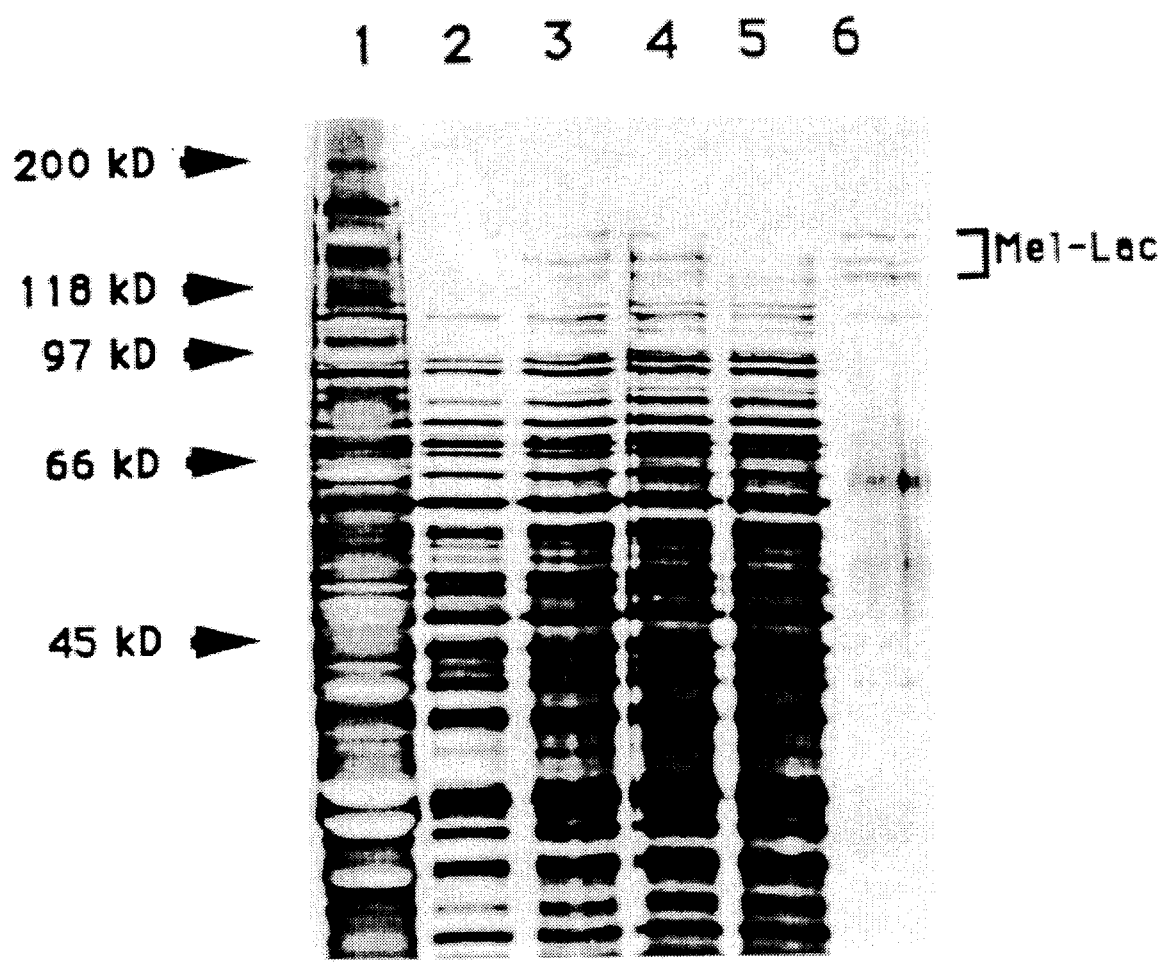
FIG. 7 shows the purification of pMAC3 fusion proteins. The fusion products of pMAC3 were purified using an anti-β-galactosidase affinity column. Aliquots of each step of the purification were collected and analyzed by SDS-PAGE and silver staining, including *S. colwelliana* D crude lysate (lane 1), $(NH_4)_2$ precipitate of this lysate (lane 2), three fractions of the unbound eluent collected during the loading of column (lanes 3–5), and the alkali-eluted, anti-β-galactosidase bound material (lane 6). Left arrows illustrate the mobility of high molecular weight standards, and the right bracket marks the fusion proteins. The photographic exposure was 2X longer for lane 6 than other lanes.

Affinity purification of the pMAC3-encoded Mela-LacZ fusion protein. Aliquots of affinity column fractions were electrophoresed on an SDS-PAGE gel and silver stained. The bound material was shown to constitute a small fraction of the cellular protein (FIG. 7, lane 6), when compared to crude sonicate (FIG. 7, lane 1), ammonium sulfate precipitate (FIG. 7, lane 2), and the three unbound fractions (FIG. 7, lanes 3–5). Specifically, these were a set of large 120–145 kD proteins (FIG. 7, lane 6, brackets). This included bands corresponding to the two reactive proteins detected in the immunoblots with anti-β-galactosidase (125 kD and 140 kD), as well as a number of smaller proteins, probably products of proteolytic cleavage during purification. The other fractions also contained these large bands, indicating that during chromatography the affinity column did not bind all of the β-galactosidase fusion proteins (FIG. 7, lanes 2–5). Even so, the column did significantly purify the large fusion protein products from the total protein suspensions, as evidenced by the relative purity of the preparation (FIG. 7, lane 6). The eluted material contained 150 mg/ml protein. The affinity-purified preparation was used to immunize three Balb/C mice and generate polyclonal antisera to the fusion protein products as described in Materials and Methods.

Figures 8A, 8B:
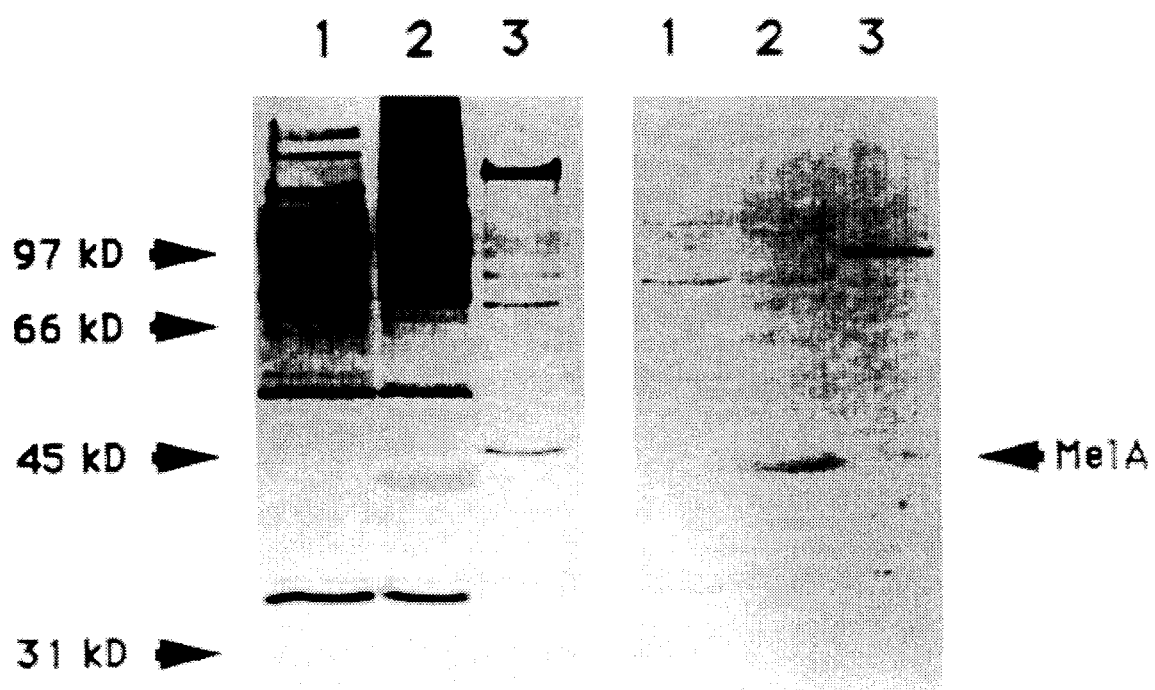
FIG. 8 is the analysis of *E. coli* and *S. colwelliana* D extracts with anti-MelA-LacZ serum. (A) crude extracts of *E. coli* JM101 pUC19 (lane 1), *E. coli* JM101 pMC3A (lane 2), and *S. colwelliana* D (lane 3) were electrophoresed on SDSPAGE, electrotransferred to nitrocellulose, and immunostained with the anti-MelA-LacZ serum. (B) The same extracts as in A, were immunostained with anti-MelA-LacZ sera that was pre-adsorbed with *E. coli* β-galactosidase and *E. coli* JM101 pUC19 whole cell extracts. Left arrows show mobilization of size standards and the right arrow points out the mobility of MelA for both blots.

Analysis of anti-MelA-LacZ serum. The polyclonal antisera was used to immunostain electrotransfers of extracts from *E. coli* JM101 carrying pUC19 or pMC3A, and *S. colwelliana* D. The *E. coli* extracts contained a number of immuno-reactive proteins, with varying degrees of staining (FIG. 8A, lanes 1 and 2). The single difference between extracts of *E. coli* carrying pUC19 and *E. coli* carrying pMC3A was a broad, lightly staining 41 kD protein. This corresponded to a lightly staining protein of the same estimated size from the *S. colwelliana* extracts (FIG. 8A, lane 3). This extract also contained a number of more strongly staining proteins in addition to the 41 kD protein. The antisera was extensively adsorbed with *E. coli* β-galactosidase and a lysate of *E. coli* carrying pUC19, and used to immunostain electrotransfers of the same three extracts. It was observed that the majority of *E. coli* proteins that had reacted strongly to the crude antisera, were either not visible, or significantly reduced in intensity, while the pMC3A-specific 41 kD protein stained more intensely (FIG. 8B, lanes 1 and 2). This pattern was also repeated with the *S. colwelliana* D extract, where the 41 kD protein remained at equal or increased intensity (FIG. 8B, lane 3). A second, larger band was not removed by the adsorption, but the nature of this protein is unknown. The antiserum was tested with dilutions of a whole cell extract from *E. coli* JM101 carrying pMC3B and was sensitive to changes in concentration over a one hundred-fold range (1 μg–100 μg) of total protein concentration (data not shown).

Figure 9:
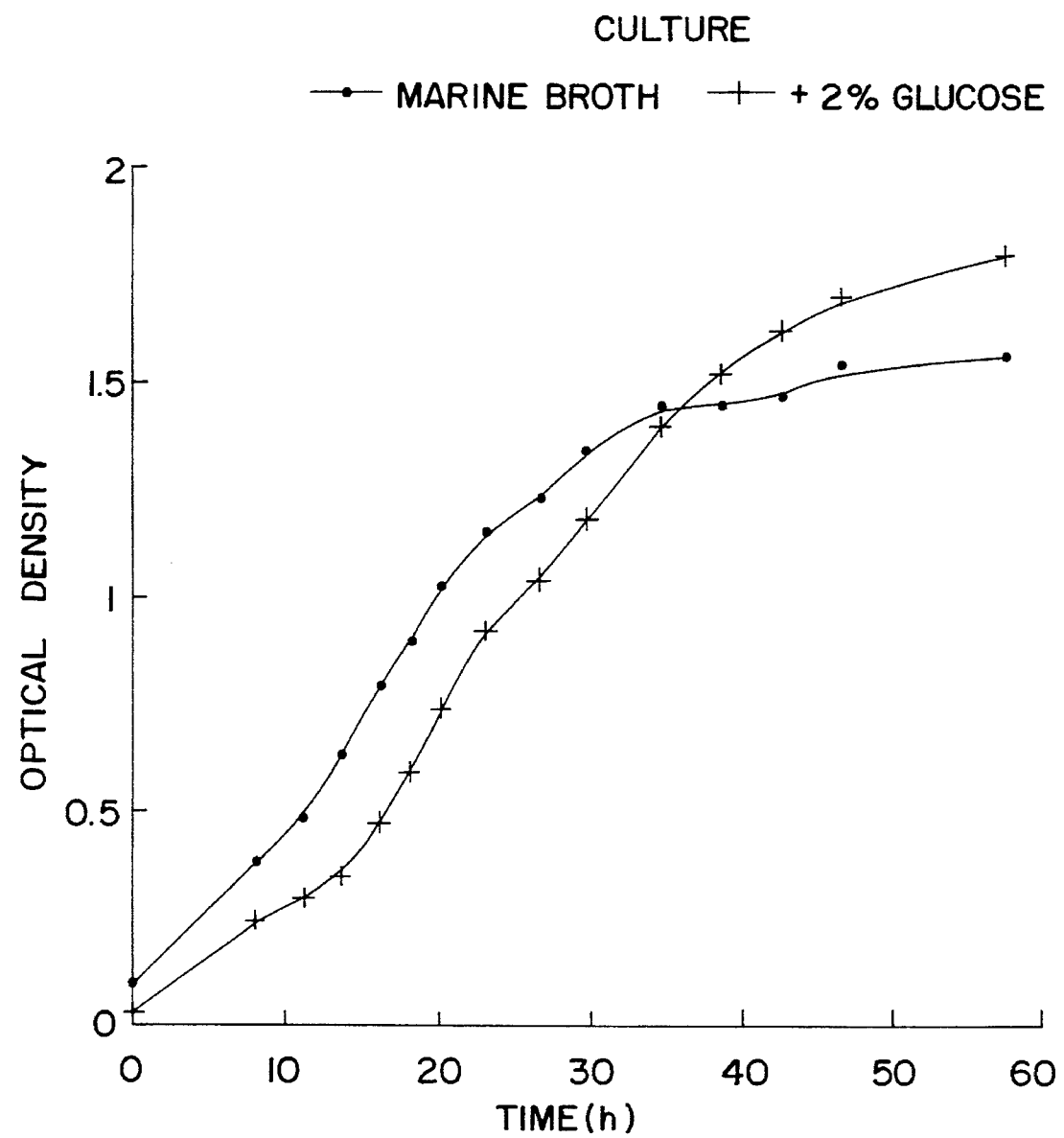
FIG. 9 shows growth curves of *S. colwelliana* D. Aliquots of *S. colwelliana* D grown with shaking at 200 RPM in 1 L of Marine Broth 2216, and 1 L of MB supplemented with 2% glucose, were removed at specific time points and analyzed for optical density at a wavelength of 650.

To determine if the appearance of melanin correlated with the presence of MelA, the anti-Mela-LacZ serum was used to monitor the levels of the protein during growth in batch culture. A pair of cultures, one in MB and the other in the same media supplemented with 2% glucose, were inoculated with 10 ml of a confluent *S. colwelliana* D culture. Aliquots were removed from the cultures over the course of growth, optical densities (O.D.) were measured, and cell pellets were frozen. O.D. readings showed that the unsupplemented culture was in logarithmic growth by 8 h post-inoculation and in stationary phase by 30–35 h (O.D. 1.5) (FIG. 9). In contrast, the culture supplemented with 2% glucose did not begin logarithmic growth until 15 h post-inoculation and was in stationary phase by 50 h (O.D. 1.7–1.8) (FIG. 9). The time of pigment formation was also significantly different for each of the two cultures, 30 and 40 h postinoculation for Marine Broth 2216 and Marine Broth plus glucose, respectively.

Figure 10A:
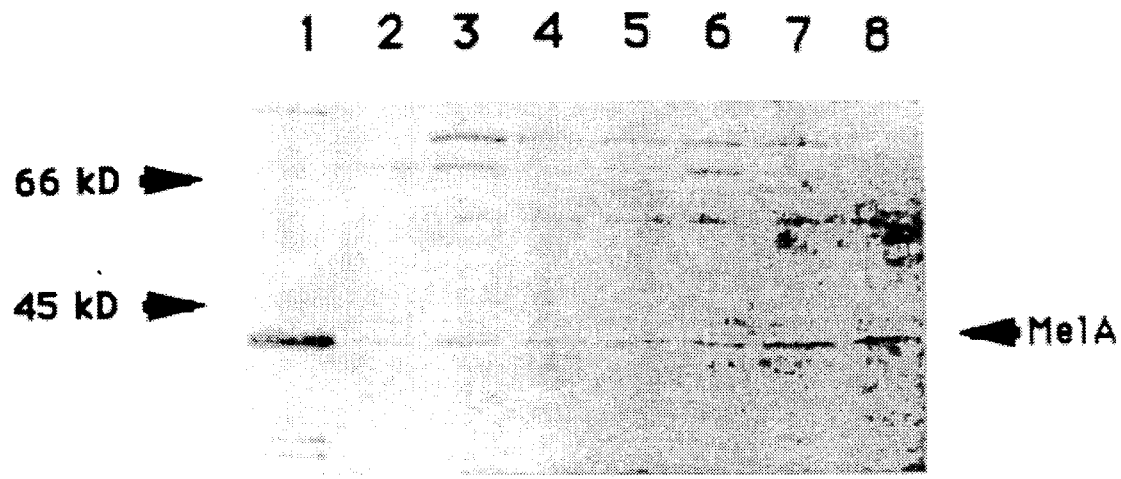
FIG. 10 is a time course for the inmunodetection of MelA during batch growth. (A) Aliquots of the same MB culture (FIG. 9) were standardized for protein, separated on SDS-PAGE, electrotransferred to nitrocellulose and immunostained with the anti-MelA-LacZ sera. *E. coli* carrying pMC3B (lane 1) and 100 μg aliquots taken at 11 h (lane 2), 16 h (lane 3), 20 h (lane 4), 26 h (lane 5), 34.5 h (lane 6), 42 h (lane 7), and 57 h (lane 8), were analyzed. (B) Analysis was of a culture grown in MB plus 2% glucose. Identical concentrations and time points as A were used, except for lanes 1 and 2 (66 and 69 μg, respectively), due to low cell densities. Left arrows indicate mobility of size standards and the right arrow marks MelA.
Figure 10B:
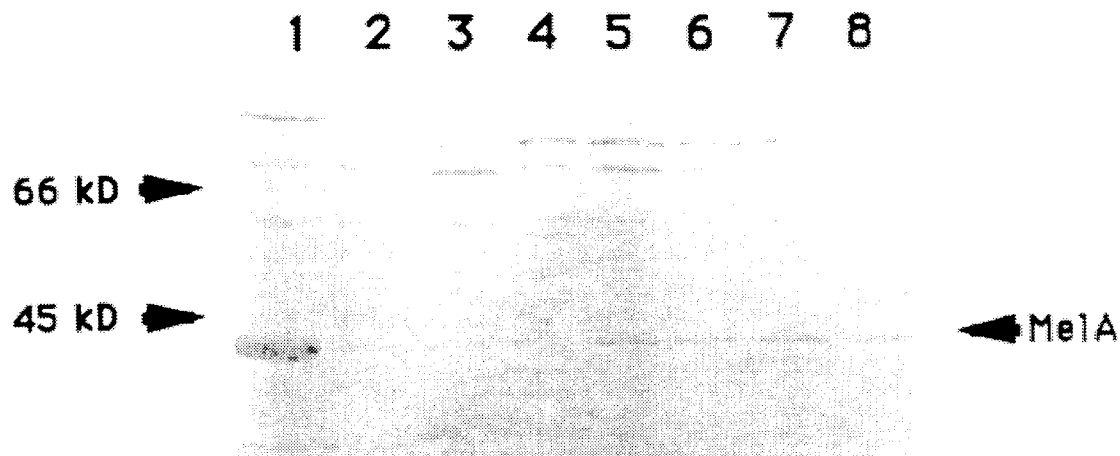

The frozen cell pellets were standardized for protein concentration, separated electrophoretically on SDS-PAGE, electrotransferred to nitrocellulose, and immunostained with the anti-MelA-LacZ serum. This revealed that the 41 kD protein was present throughout the growth cycle in the unsupplemented Marine Broth and the 2% glucose-supplemented cultures (FIG. 10A and 10B, lanes 1–8). Furthermore, there was no significant difference between the steady state level of melA in the two cultures.

Figure 11:
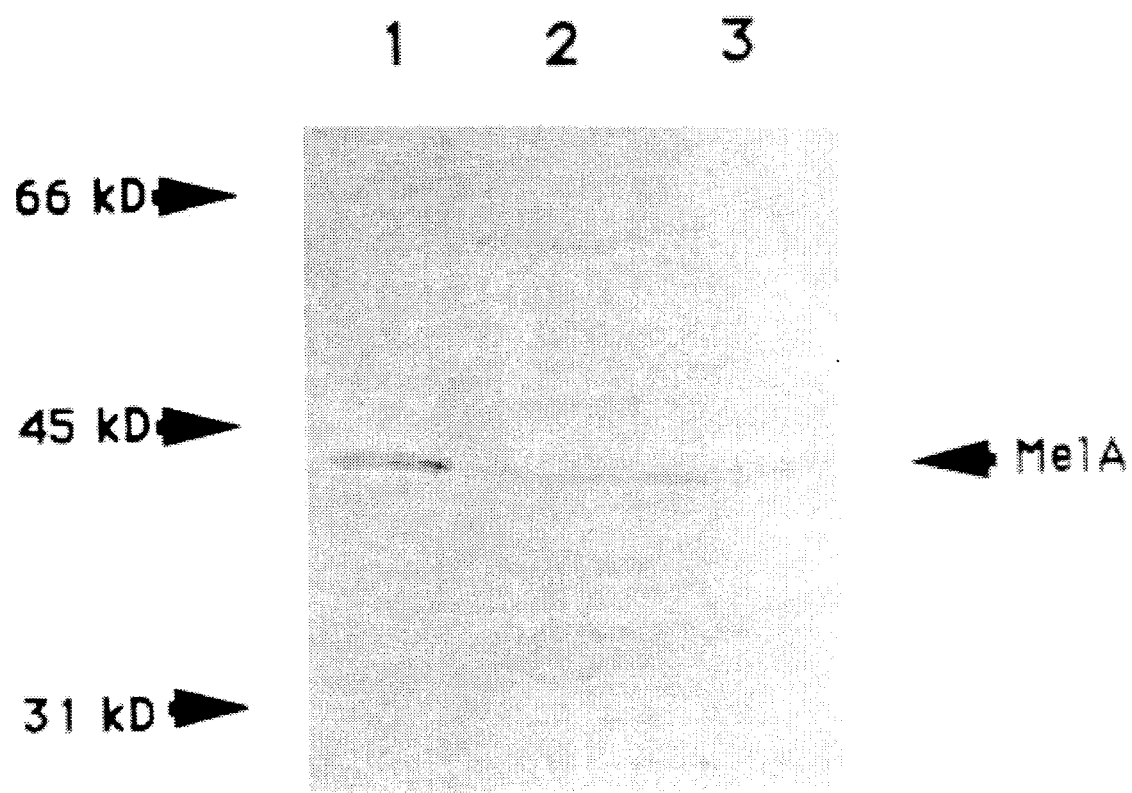
FIG. 11 shows MelA synthesis in media supplemented with tyrosine and copper. Whole cell extracts of two parallel cultures of *S. colwelliana* D, one grown in Marine Broth 2216 and the other in Marine Broth 2216 plus 5 mM tyrosine and 5 μg/ml $CuSO_4$, shaken at 200 RPM, were prepared. 10 μg of *E. coli* JM101 carrying pMC3B (lane 1) and 100 mg of the unsupplemented culture extract (lane 2) and the tyrosine-copper supplemented culture extract (lane 3) were separated by SDS-PAGE, electrotransferred to nitrocellulose and immunostained with the anti-MelA-lacZ antibodies. Left arrows indicate mobilization of size standards and the right arrow marks MelA.

Enhancement of pigmentation with tyrosine and copper. To determine whether the enhanced pigmentation observed in the presence of tyrosine and $CuSO_4$ was due to an induction of melA synthesis, parallel cultures of S. colwelliana D were grown, one unsupplemented and one with added tyrosine (5 mM) and $CuSO_4$ (5 µ/ml). Cells were harvested from these cultures in late logarithmic stage, washed, resuspended and frozen. Equal amounts of protein were electrophoresed on SDS-PAGE, electrotransferred, and immunostained with anti-MelA-LacZ serum. Comparison of the two extracts suggested at most a two-fold induction of MelA synthesis in the tyrosine-$CuSO_4$ supplemented culture (FIG. 11, lanes 2 and 3).

Figure 12A:
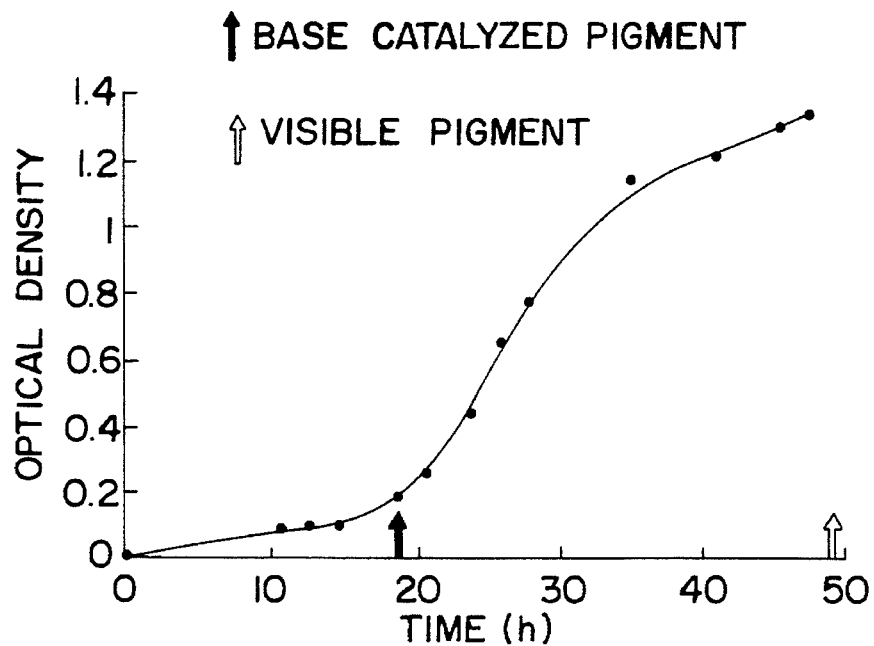
FIG. 12 shows melanin precursors and dissolved oxygen in *S. colwelliana* D culture. (A) 10 ml aliquots of a MB shaken at 200 RPM were removed at specific times during growth. Melanin in culture was also recorded at each time point. The optical density of each extract was measured, the sample was treated with 0.5 g of solid NaOH, and scored for melanin formation. (B) Aliquots of cultures in MB shaken at 300 RPM were removed at specific time points and analyzed for optical density (+) and dissolved oxygen levels (●).

S. colwelliana D melanin production occurs late in logarithmic growth, but the synthesis of MelA appears to be constitutive (FIG. 10A and 10B). Catecholamines or hydroxyquinones will spontaneously polymerize to melanin under oxidative and/or basic conditions (Bell et al, Ann. Rev. Phytopathol. 24:411–451 (1986)). Supernatants of S. colwelliana D from early or mid-logarithmic, prepigmentation cultures were observed to pigment when oxygenated. This suggested that the melanin precursors were being synthesized significantly earlier than the onset of melanin polymerization. To determine how early melanin precursors were accumulating, 10 ml aliquots of an actively growing S. colwelliana D culture were removed at various times, treated with 0.5 g of solid NaOH, shaken vigorously, and monitored for pigment formation. This revealed that melanin precursors were present even in the early stage of growth in MB (FIG. 12A). MB treated in the same manner was used as a negative control and consistently remained unpigmented.

Figure 12B:
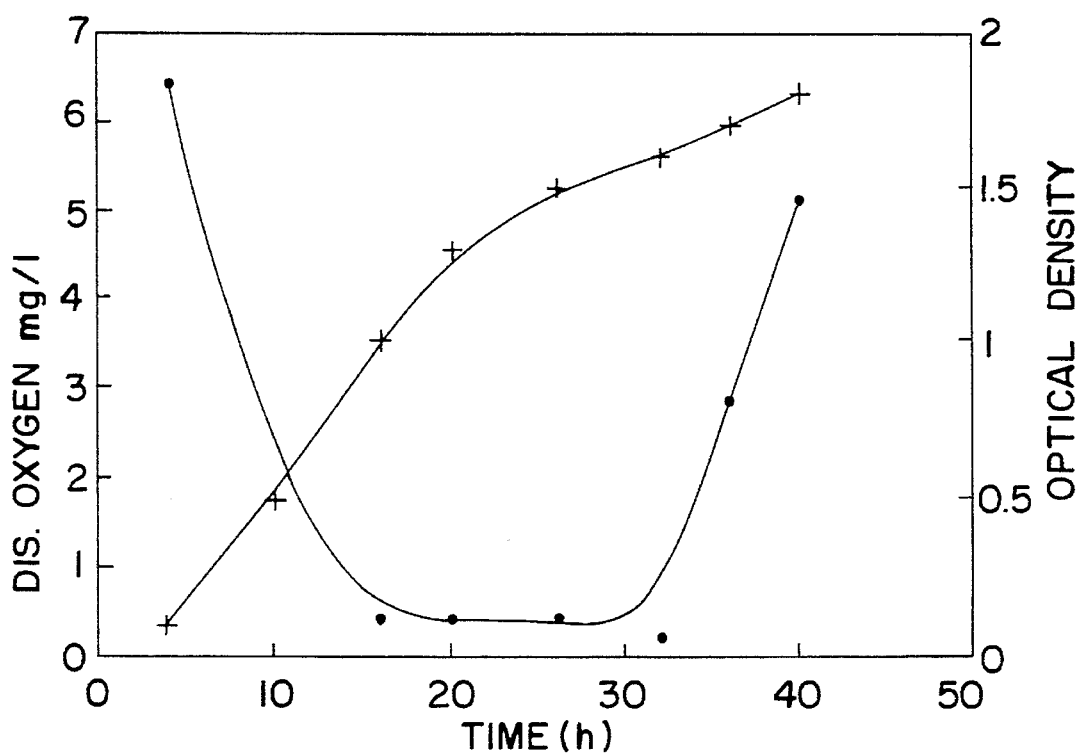
Figure 13:
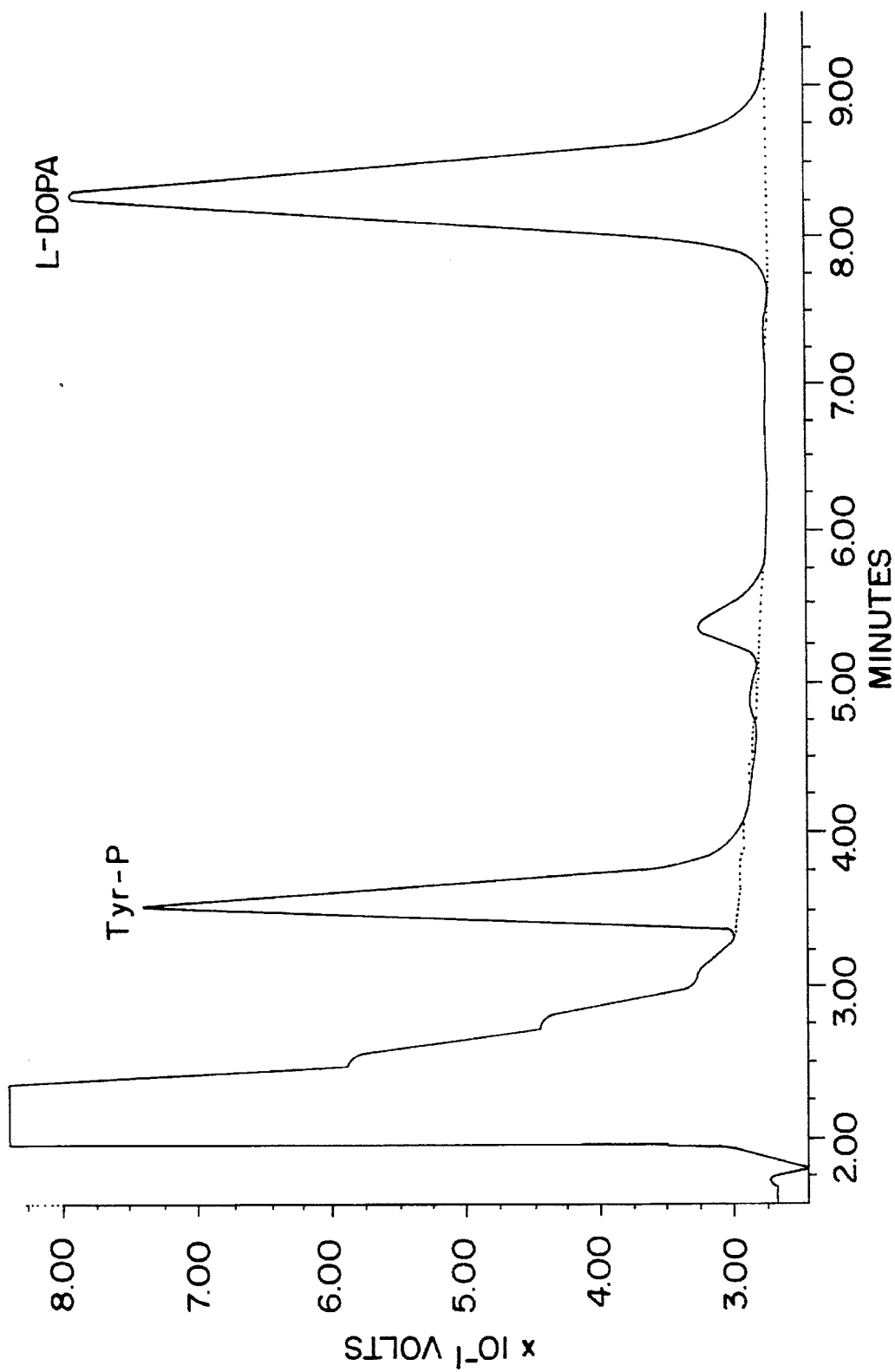
FIG. 13 is an HPLC elution profile of S. colwelliana D assay products. Assays were conducted with whole cell extracts as described in Materials and Methods.

Previous work had shown that actively growing cultures of S. colwelliana D were depleted of dissolved oxygen. Surprisingly, this was observed even for S. colwelliana D cultures grown at the highest obtainable aeration in culture flasks (i.e. with a wrist action shaker at its maximum setting). A time course experiment where dissolved oxygen was measured in cultures of S. colwelliana D over the growth cycle showed that oxygen levels were close to saturation at the time of inoculation, as low as detectable during logarithmic growth, and returned to high levels during stationary phase (FIG. 12B). By 15 h postinoculation, the levels of dissolved oxygen were lower than the oxygen electrode sensitivity (0–5 mg/L), and remained so until 32 h had elapsed. Increases of dissolved oxygen coincided with the slowing of culture growth, and also the first signs of visible pigmentation.

This protein exhibited β-galactosidase activity and reacted with anti-β-galactosidase antibodies. To overexpress Mel'::'Lac, the vector containing the gene fusion was introduced into E. coli, a transformant selected and cultured under normal conditions to express the fusion protein. After confluent growth, the cells were harvested, lysed, and the fusion protein was affinity purified using anti-β-galactosidase antibodies.

To prepare polyclonal antibodies against MelA, the affinity purified fusion protein was injected into mice using standard procedures [Harlow et al. (1988), Antibodies: A Laboratory Manual, Cold Spring Harbor Laboratory, Cold Spring Harbor, N.Y., pp. 726.] The antiserum was tested by immunoblotting whole cell extracts of E. coli strains producing the melA gene product and whole cell extracts of S. colwelliana. An E. coli strain lacking the melA gene served as a control. The immunoblots revealed that the antiserum reacted specifically with an $M_{T\ 42,000}$ protein present in S. colwelliana and in E. coli expressing the melA gene, but not in E. coli lacking the melA gene.

Monoclonal antibodies are prepared by removing the spleens from mice injected for polyclonal antibodies (after determining that the mice are producing anti-MelA antibodies). The splenocytes are then isolated and used in cell fusions with murine myeloma cells to generate antibody-producing hybridomas (Harlow et al.). The hybridoma supernatants are subsequently screened by immunoblotting as above to identify hybridomas which produce antibodies against MelA.

EXAMPLE 5

Overexpression of the melA Gene

A replicable expression vector to overproduce the S. colwelliana MelA under control of the lacZ promoter was constructed. Briefly, a DNA restriction fragment from pUC19 containing the lacZ promoter was ligated to the 1.9-kb HincII fragment containing the melA coding sequence to generate plasmid pMC3B as depicted in FIG. 4. pMC3A and pMC3B have the HincII fragment in opposite orientations, such that in pMC3B transcriptional readthrough occurs from the lac promoter into the melA gene. E. coli containing pMC3B produces MelA at elevated levels relative to pDC1 as evidenced by darker pigmentation of the colonies and 10-fold or higher RNA levels.

EXAMPLE 6

RNA isolation, blotting and hybridization

RNA was extracted by the technique of Summers (W. C. Summers (1970) Anal. Biochem. 33:459–463) from 50 ml cultures of S. colwelliana D or E. coli JM101 carrying the plasmids of interest. All buffers and solutions used for this protocol were made RNAse-free by treatment with diethylpyrocarbonate (DEPC). Cells were collected by centrifugation (12,000×g, 10 min, 4° C.) and the pellet was resuspended in 10 ml of Protoplasting buffer. Lysozyme chloride was added (80 µl of a 50 mg/ml stock), and incubated for 15 min on ice. Protoplasts were collected by centrifugation (5900×g, 5 min, 4° C.). The pellet was resuspended in 1 ml of lysis buffer, 30 µl of DEPC was added, and the mixture was incubated at 37° C. for 5 min followed by addition of 500 µl of a saturated NaCl solution on ice, and incubation for 10 min. The precipitated protein was removed by centrifugation (6,400×g, 10 min in a microfuge), and the nucleic acid in the supernatant ethanol precipitated. The nucleic acid was collected by centrifugation (6,400×g, 15 min in a microfuge), followed by a 70% ethanol rinse, recentrifugation, and air drying of the pellet. The pellet was resuspended on ice [400 µl of IX DNAse I buffer, 80 U RNAsin (Promega Biotech, Madison, Wis.)], and DNA was removed by digestion with 75 U of RNAse-free DNAse I (Boehringer-Mannheim Biochemicals, Indianapolis, Ind.) for 2 h at 25° C. Following digestion, the RNA was extracted with phenol/chloroform, and ethanol precipitated. The RNA pellet was resuspended on ice (100 11X DNAse I buffer, 20 U of RNAsin) and digested with 15 U of DNAse I for 30 min at 25° C. The RNA was phenol/chloroform extracted, ethanol precipitated, and collected by centrifugation (6,400×g, 15 min). The pellet was resuspended in 30 μl of $H_2O$ and stored at −70° C.

RNA was separated electrophoretically on 1.3% formaldehyde-agarose gels as described elsewhere (J. Sambrook, E. Fritsch, and T. Maniatis (eds). (1989) Molecular Cloning: A Laboratory Manual. Second Edition. Cold Spring Harbor Laboratory Press, New York). Typically, 30–50 μg RNA was incubated in sample treatment buffer (15 min, 65° C.). Gel-loading buffer was added to the treated sample prior to loading onto a 1.3% formaldehyde-agarose gel (1.3% agarose, 6.6% formaldehyde, 1X MOPS running buffer). This was electrophoresed (4 volts/$cm^2$) in 1X MOPS running buffer approximately ¾ the length of the gel as judged by migration of bromophenol blue tracking dye. Size estimation of the separated RNA was achieved by electrophoresing ethidium bromide-stained RNA size standards (Bethesda Research Laboratories, Gaithersburg, Md.) alongside the RNA samples.

Separated RNA was transferred to Zeta-Probe nylon membranes by an alkaline, capillary blotting procedure (D. A. Mann and K. C. Reed (1987) *Biorad Molecular Biology Reports* 1:1–4) using 50 mM NaOH as the transfer solution. The gel was rinsed four times in DEPC-treated $H_2O$ to remove excess formaldehyde before transferring overnight as described by Sambrook et al (J. Sambrook, E. Fritsch, and T. Maniatis (eds) (1989) *Cold Spring Harbor Laboratory Press,* New York). Following transfer, the membrane was marked for orientation, rinsed in 2X SSPE, and allowed to air dry.

For hybridization, the dried membrane was rehydrated by soaking in 6X SSPE. The membrane was placed in a heat-sealable plastic bag with RNA prehybridization solution (0.2 ml/$cm^2$ of membrane), and incubated at least 1 hr at 65° C. Following this, the RNA prehybridization solution was poured off and replaced with DNA/RNA hybridization solution (0.05 ml/$cm^2$ of membrane). The radio-labeled oligonucleotide was added, the bag resealed, and the hybridization was allowed to proceed with shaking for at least 16 hr at 65° C. After this incubation, the hybridization solution was poured off, the membrane removed, and washed twice for 5 min at 25° C. (5X SSPE, 0.01% SDS) and twice for 5 min in the same wash solution at 37° C. If high background remained (as judged by Geiger counting), additional washes were performed for 5 min at 37° C. (4X SSPE, 0.01% SDS). The membrane was enclosed in a single layer of plastic wrap and autoradiographed on X-ray film.

Northern blotting. Total RNA from several *E. coli* JM101 strains carrying pUC19 or melA plasmids, and RNA from *S. colwelliana* D was separated electrophoretically on formaldehyde-agarose gels. The RNA in these gels was transferred to nylon membranes and probed with a melA-specific radio-labeled oligonucleotide probe, complementary to the 5′ (nts 304–333) coding sequence of the melA gene. RNA derived from *E. coli* carrying pUC19 did not bind the probe. Surprisingly, RNA from a melanin-synthesizing *E. coli* carrying pMC3A (Table I), also did not bind detectable levels of probe. In addition, *S. colwelliana* D RNA also failed to show detectable hybridization to the probe (data not shown). In contrast, RNA from *E. coli* JM101 carrying pMC3B, hybridized strongly with the probe, as two distinct transcripts of 1.6 and 1.3 kb. This construct contains the identical DNA insert as pMC3A, but in the opposite orientation in pUC19 (Table I). The upstream regions of pMC3A and pMC3b were resequenced and again shown to be identical. In pMC3B, the melA coding region begins 316 bp downstream of the pUC19 lacZ promoter. It is most likely that this orientation resulted in a fortuitous operon fusion between the pUC19 lacZ promoter and the melA gene, and that transcription of melA initiates from the lacZ promoter in addition to the melA promoter. The sizes of the two transcripts (1.6 and 12.3 kb) match well with the transcript sizes predicted from such a configuration. Interestingly, this suggests that expression from the lacZ promoter has also increased transcription initiation from the melA promoter.

TABLE I

| Bacterial strains, plasmids, and phage | |
|---|---|
| Strain, plasmid or phage | Relevant characteristics |
| *S. colvelliana* | |
| strain D | diffusable pigment |
| strain V | viscous exopolysaccharide |
| *E. coli* | |
| HB101 | host strain, recA13 |
| JM101 | host strain, α-complementation strain |
| SE5000 | Maxicell strain, recA56 |
| Plasmids | |
| pHC79 | cosmid cloning vector, $Ap^R$, $TC^R$ |
| pUC19 | cloning vector for α-complementation systems, ApR, Lac+ |
| pCT1 | original Mel + clone, 10.1 kb *S. colwelliana* insert, $Ap^R$ |
| pDC1 | 4.2 kb PstI fragment of pCT1 in pUC19, $Ap^R$, Mel+ |
| pDC2 | same as ppcl, opposite orientation in pUC19, $Ap^R$, Mel+ |
| pDC3 | 4.0 kb PstI-NcoI fragment of pDC1 in pUC19, $Ap^R$, Mel+ |
| pDC4 | 3.3 kb PstI-HincII fragment of pDC1 in pUC19, $Ap^R$, Mel+ |
| pMC1 | 3.7 kb BglII-NcoI fragment of pDC3 in pUC19, $Ap^{R, Mel+}$ |
| pMC2 | 3.3 kb BglII-SphI fragment of pMC1 in PUC19, $Ap^R$, Mei+ |
| pMC3A | 1.9 kb HincII-HincII fragment of pMC2 in pUC19, $Ap^{R, Mel+}$ |
| pMC3B | same as pMC3A, opposite orientation in pUC19, $Ap^R$, mel+ |
| pMC4B | 1.6 kb PleI-PleI fragment of pMC3A, opposite orientation in pUC19, $Ap^R$, Mel+ |
| pMC5A | 1.3 kb HincII-DxaIII fragment of pMC3A in pUC19, $Ap^R$, Mel+ |
| pMC6A | 1.3 kb NspI-NspI fragment of pMC3A in PUC19, $Ap^R$, Mel− |
| pNC1 | 3.2 kb EcoRI-PstI fragment of pDC1 in pUC19, $Ap^R$, Mel− |
| pNC2 | 300 bp. BglII-BglII deletion of pMC3A, $Ap^R$, Mel− |
| pNC3 | 784 bp HincII-HincII fragment of pMC3A in pUC19, $Ap^R$, Mel− |
| pNC4 | 1.1 kb HincII-HincII fragment of pMC3A in pUC19, $Ap^R$, Mel− |
| pNC5 | 1.5 kb Ps I-BGIII fragment of pDC1 in PUC19, $Ap^R$, Mel− |
| Phage | |
| M13mp19 | single-stranded DNA phage for DNA sequencing, $Ap^R$, Lac+ |
| M13mpMCA | 729 bp BglII-DraIII fragment of pMC3A in |

TABLE I-continued

Bacterial strains, plasmids, and phage

| Strain, plasmid or phage | Relevant characteristics |
|---|---|
| | M13mp19 |

EXAMPLE 7

Isolation of mlgh Gene

The 5' end of a second ORF, directly downstream and in the same orientation as melA was identified, and designated mlgA (mel-linked gene). The entire sequence of mlgA was obtained and is depicted in FIG. 14. This ORF contained an internal HincII recognition site and corresponded to the 17 kD protein revealed during the in vitro expression analysis. The ORF had two potential translational initiation sites, an ATG codon at position 95, and an ATG codon at position 177, the translation products of which were predicted to be 19.3 kD (176 amino acids) and 16.6 kD (153 amino acids), respectively. The most likely start site was at position 177 since the size of this translation product was closest to that observed in the in vitro expression experiments. Furthermore, there is a consensus ribosome binding site (RBS) upstream of the ATG (7 nts) at position 177, while there is no RBS consensus sequence upstream of the ATG at position 95. The role of this protein in melanogenesis is unclear because deletion subcloning in E. coli demonstrated that only melA was required for the observed pigment synthesis.

EXAMPLE 8

Sequence analysis and homology studies

Figure 15:
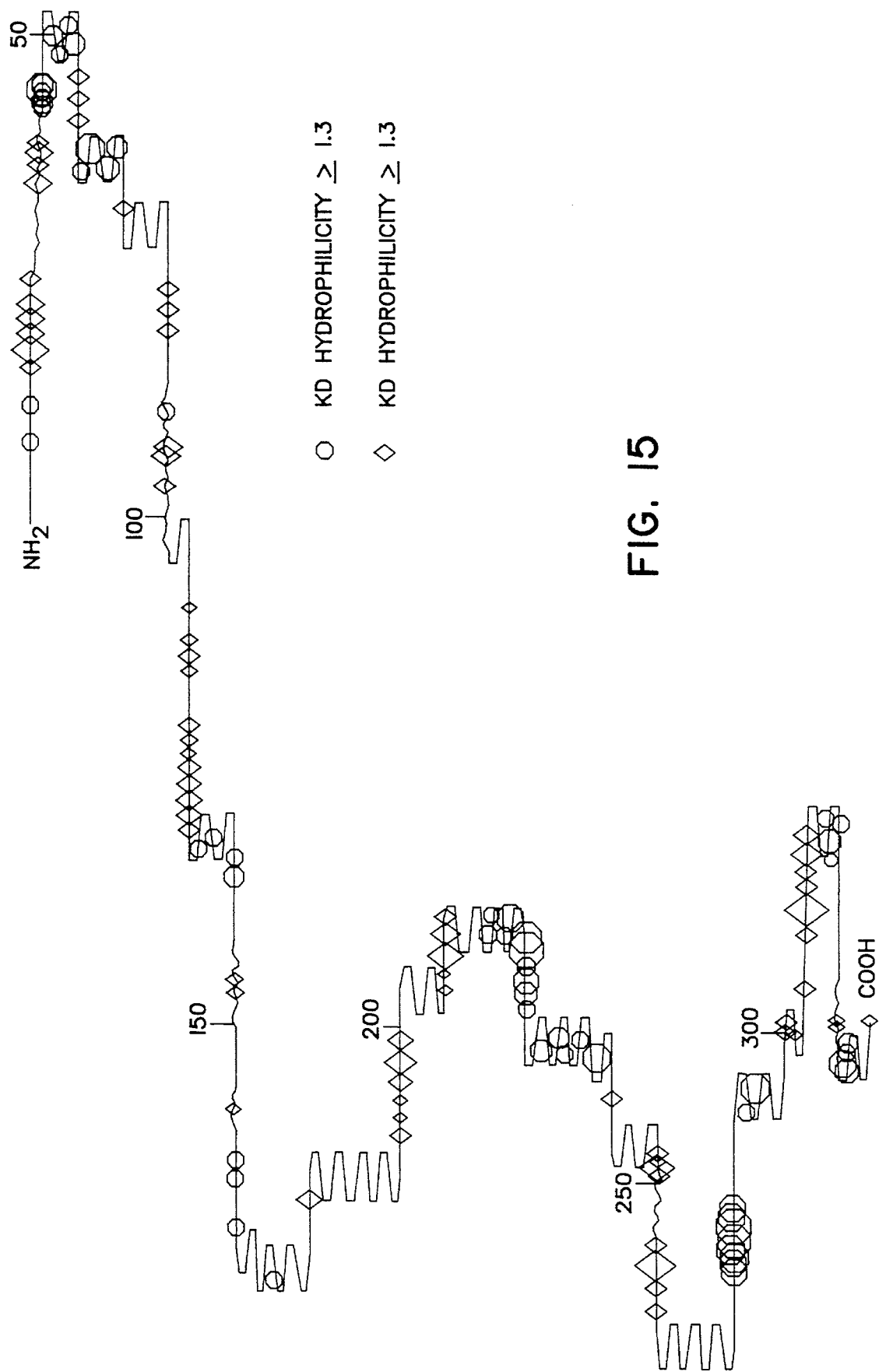
FIG. 15 is the predicted secondary structure of melA gene product. This secondary structure plot was generated using the Kyte-Doolittle hydropathy index (J. Mol. Biol. 157:105–132) and running the algorithm of Garnier-Osguthorpe-Robson (J. Mol. Biol. 120:97–120) to predict the structure. The Wisconsin Package from the Genetics Computer Group was used to run the algorithms and generate the figure. Large sine-wave represents α-helices; the more shallow sine-wave represents βpleated sheets; 90° turns represent β-bends, and straight lines represent random coil. The overstruck diamonds and octagons represent hydrophobic and hydrophilic regions of the polypeptide, respectively.

The predicted amino acid sequence for the melA gene product was deduced and analyzed for any recognizable structural motifs. Net charge and hydropathy plots of MelA revealed an acidic protein with no strong tendencies towards hydrophobicity or hydrophilicity. No potential membrane-spanning helices or hydrophobic signal sequences were identified, as determined by the methods of Eisenberg et al (D. Eisenberg, E. Schwartz, M. Komarony and R. Wall (1984) *J. Mol. Biol.* 179:125–142) and yon Heijne (G. von Heijne (1986a) EMBO J. 5:3021–3027), respectively. The sequence of this protein predicts a polypeptide possessing a relatively even distribution of α-helical and β-pleated sheet regions (J. Garnier, D. J. Osguthorpe, and B. Robson (1978) *J. Mol. Biol.* 120:97–120), with no significant bias towards either structural motif. A predictive secondary structure plot summarizing this information is shown in FIG. 15.

Sequence alignments between MelA and the tyrosinases from human, mouse, *Neurospora crassa*, and *Streptomyces* spp. (PIR, Swiss-Prot and NBRF protein sequence databases) revealed no stretches of significant homology. Furthermore, there were no recognizable copper-binding sites in the MelA sequence (K. Lerch, M. Huber, H. Schneider, R. Drexel, and B. Linzen (1986) *J. Inorg. Biochem.* 26:213–217). Global searches of these databases also failed to identify any protein sequences with significant similarity to MelA.

The predicted amino acid sequence for the mlgA gene product (starting at position 177, FIG. 14) was also analyzed for structural tendencies or motifs. The hydropathic plot of mlgA revealed a protein that is highly hydrophobic, suggesting the possibility of membrane-association. Furthermore, using the same algorithms as above (D. Eisenberg, E. Schwartz, M. Komarony and R. Wall (1984) *J. Mol. Biol.* 179:125–142; G. yon Heijne (1986a) *Nucl. Acids Res* 14:4683–4690), 4 potential membrane-spanning regions and 2 potential signal sequences for membrane insertion were predicted.

In addition to a functional promoter, sequence analysis of melA revealed a stem and loop structure, beginning at position 1380, immediately downstream of the 3' end of the melA coding sequence. This structure has the attributes of a factor-independent transcriptional terminator, namely a GC dyad stem immediately preceding a stretch of AT rich sequence (T. Platt (1986) *Ann. Rev. Biochem.* 55:339–372). The presence of an upstream promoter and a transcriptional terminator directly downstream suggests that melA is monocistronic, and expressed as a unique transcript. Northern blotting of total RNA did not reveal significant levels of the melA transcript when initiation only occurred from the melA promoter. Nevertheless, the proposal that the melA transcript is monocistronic is consistent with the Northern blots of RNA derived from *E. coli* carrying pMC3B, a construct encoding a fortuitous lacZ'::mela operon fusion (Table 1). The sizes of the two transcripts, 1.6 kb and 1.3 kb, were consistent with those predicted from transcriptional initiation at the lacZ and melA promoters and termination at the putative factor-independent terminator downstream of melA.

There are 114 bp of leader sequence between the putative melA promoter and the start codon, and in this region there are two mutually exclusive stem and loop structures. The free energies for the upstream (−6.8 dG) and the downstream (−8.2 dG) stem and loops suggest a significant, yet plastic, structure (I. Tinoco, P. N. Borer, B. Dengler, M. D. Levine, O. C. Uhlenbeck, D. M. Crothers, and J. Gralla (1973) *Nature New Biology* 264:40–41). The occurrence of sequencing artifacts (termination with all four dideoxynucleotides) indicative of secondary structure, at several nucleotides directly involved in these putative stem-loop structures, provides in vitro evidence to support these predictions (data not shown).

The sequences are also rich in glycine (8.4% and 14.7%), alanine (9.2% and 15.4%), and arginine (9.2% and 5.6%, respectively). In comparison, the MelA sequence predicts an acidic, protein which is neither highly hydrophobic or hydrophilic. The enzyme is probably cytoplasmic and there is no evidence that it is secreted. The amino acid composition reveals a similar bias against sulfur-containing amino acids, with 1 (0.3%) cysteine and 5 (1.4%) methionine residues. The MelA amino acid sequence is rich in the acidic amino acids glutamate (7.2%) and aspartate (9.2%) as well as isoleucine (9.2%), glycine (8.1%) and phenylalanine (8.1%). Although MelA shares some general structural and compositional tendencies with the Streptomyces enzymes, it shows no significant sequence homology with these proteins. In particular it does not have a distinguishable Type III copper-binding site (J. A. Fee (1978) p.–60, in J. d. Dunitz, P. Hemmerich, R. H. Holm, J. A. Ibers, C. K. Jorgensen, J. B. Neilands, D. Reinen, and R. J. P. Williams (eds) Vol. 23 Structure and bonding. Springer-Verlag, New York) conserved in tyrosinases and hemocyanins (K. Lerch, M. Huber, H. Schneider, R. Drexel, and B. Linzen (1986) J. Inorg. Biochem. 26:213–217). In addition, MelA is distinctly different from, and shows no sequence homology to laccase (U. A. Germann, G. Muller, P. E. Hunziker, and K. Lerch (1988) *J. Biol. Chem.* 263:885–896), as well as all of the Type I "blue" copper proteins (J. A. Fee (1978) p.1–60, in J.d. Dunitz, P. Hemmerich, R. H. Holm, J. A. Ibers, C. K. Jorgensen, J. B. Neilands, D. Reinen, and R. J. P. Williams (eds) vol. 23 Structure and bonding. Springer-Verlag, New York).

There is preliminary evidence that melanogenesis in *S. colwelliana* is inhibited by the copper-specific chelator diethyldithiocarbamate (DDC) (Dagasan et al, unpublished results). MelA contains 8 histidine residues, the ligand in Type III copper-binding sites of tyrosinases and hemocyanins, and these may be involved in metal ligation via a previously undefined coordination chemistry. Alternatively, in the blue copper proteins such as laccase, the copper is bound via four ligands, a cysteine, a methionine, and two histidines (P. M. Colman, H.c. Freeman, J. M. Guss, M. Murata, V. A. Norris, J. A. M. Ramshaw, and M. D. Venkatappa (1978) *Nature* 272:319–324). A similar multiligand binding site may be functioning in MelA. The inhibition studies described above were conducted with crude or partially purified *S. colwelliana* D extracts.

Sequence analysis of mlgA. In addition to melA, a second gene, designated mlgA, was cloned and sequenced. Deletion analysis of the region flanking melA indicated that mlgA is not required for melanin synthesis in *E. coli*, but did not eliminate the possibility that mlgA is involved in melanogenesis in *S. colwelliana*. Computer analysis of the predicted MlgA amino acid sequence revealed that the protein is predominantly hydrophobic, and is likely to be integrally membrane-associated. Results from in vitro expression and maxicell analyses with constructs encoding MlgA support this prediction. The in vitro expression, in agreement with the sequence, suggested that the protein was 17 kD. However in maxicell analysis, the 17 kD protein was not observed, even for constructs that were verified to encode MlgA by DNA-directed expression and sequence analysis. Rather, a large aggregate that barely entered the gel, was consistently observed in SDS-PAGE analysis of maxicell extracts that encoded intact MlgA, and was absent from those that did not. Maxicells possess membranes, and most cellular processes are still functional, specifically those involved in insertion of proteins into membranes. In contrast, the DNA-directed expression system is truly in vitro, lacking any intact membranes. Considering this, it is likely that MlgA expressed in maxicells, was inserted into membranes, aggregated with itself, and/or with other membrane components, and did not enter the SDS-PAGE gel.

Figure 16:
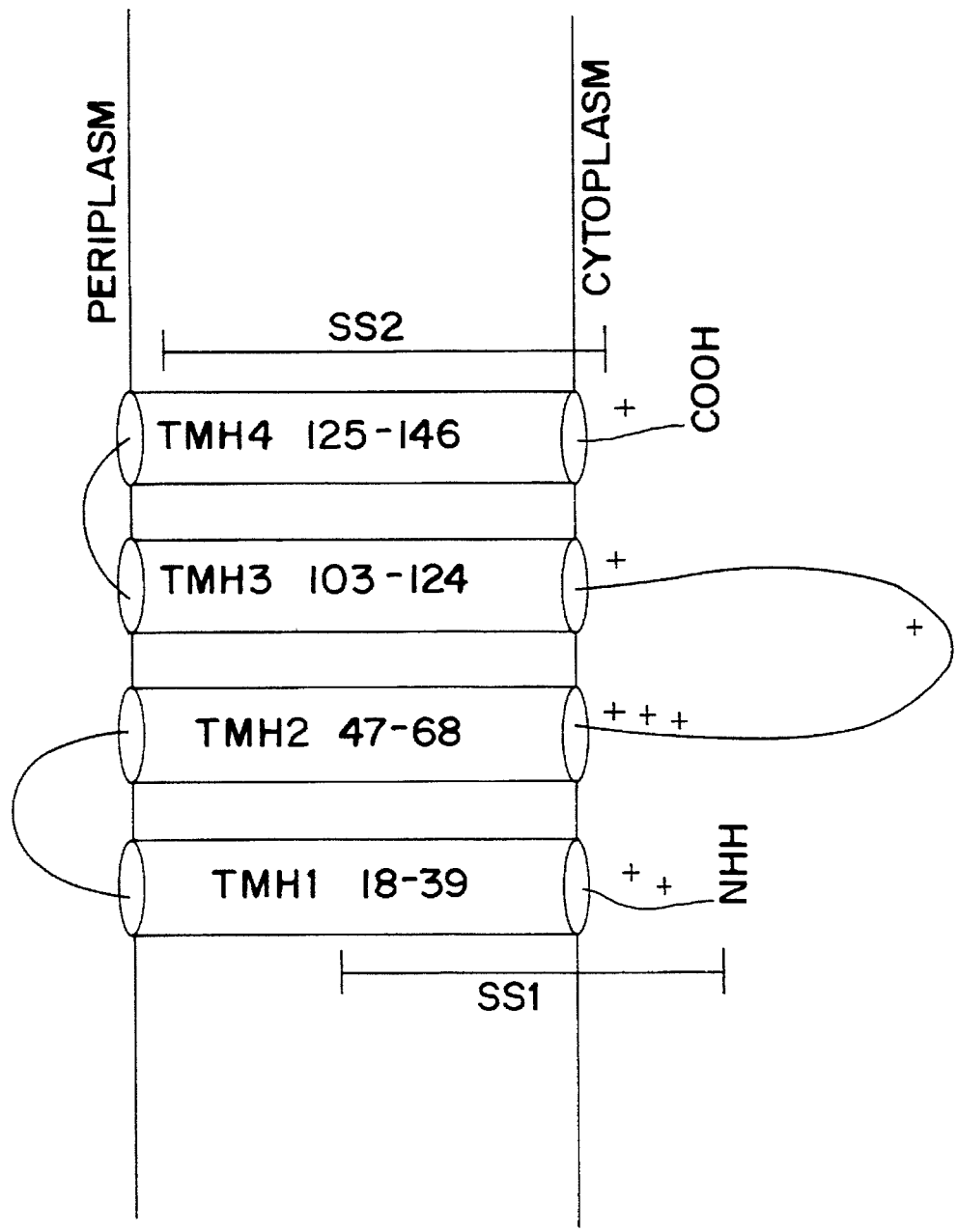
FIG. 16 is the potential membrane orientation of MlgA. Transmembrane helices and potential signal sequences were predicted using the programs of Eisenberg et al (J. Mol. Biol. 179:125–142) and von Heijne (Nucl. Acids Res. 14:4683–4690), and are shown here as rods and bracketed lines, respectively. Both of these programs were accessed using the Intelligenetics PC Gene program. Positively charged amino acid residues are denoted with + signs.
Figure 17:
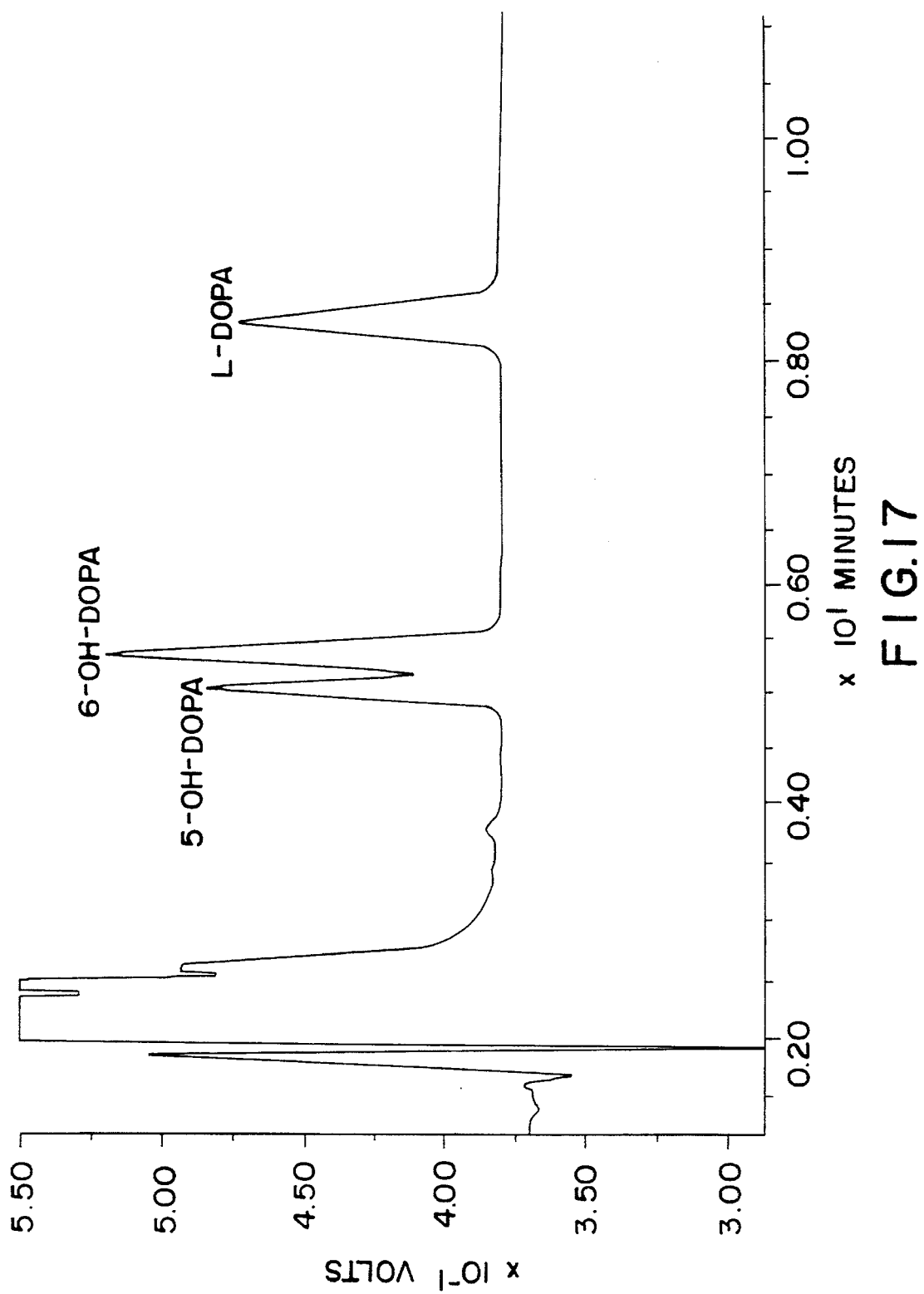
FIG. 17 as an HPLC elution profile of a catecholamine standard set, containing 200 pmole each of 5-OH-DOPA, 6-OH-DOPA, and DOPA. The Waters 460 Electrochemical Detector was set at a potential of 0.7 V and a 20 nA range of sensitivity. The x-axis is elution time and the y-axis is the electrochemical response.

The predicted mlgA gene product is composed of 4 potential membrane-spanning helices and 2 potential signal sequences. Compilation of sequence data from integral membrane proteins reveals a trend in the membrane orientation of these proteins. Interhelical loops of membrane proteins tend to be oriented as a function of the net charge of the region; with positively charged interhelical loops on the cytoplasmic side of the membrane, and neutral or negatively charged regions exposed to the medium (or periplasmic space) (G. von Heijne (1986b) *EMBO J.* 5:3021:3027; G. von Heijne and Y. Gavel (1988) *Eur. J. Biochem.* 174:671–678). In light of the placement of membrane-spanning helices and signal sequences one can predict the orientation of a protein relative to the membrane by its charge distribution. The illustration in FIG. 16 is such a prediction, and summarizes the information on the secondary structure of MlgA, offering one potential orientation for the protein in the membrane. In this interpretation, the protein crosses the membrane 4 times with a pair of short segments exposed to the medium or periplasm, and one relatively large interhelical segment on the cytoplasmic side of the membrane. Although this membrane orientation model of MlgA conforms with the above generalizations, it remains hypothetical.

EXAMPLE 9

Determination of the transcriptional start point

Primer extension analysis. For primer extension experiments, a synthetic 30mer (5'GTTTTGTTCGCTTGCCATG-TAAT-TATCCTC-3') (SEQ. ID NO. 2) complementary to the 5' end of melA (nucleotides 304–333) was end-labeled with T4 polynucleotide kinase. The labeled primer (2 pmole) was coprecipitated with total RNA (150 µg or 6 µg). The mixture was resuspended in aqueous hybridization buffer and allowed to anneal overnight at 32° C. This mixture was ethanol precipitated and redissolved in 2X reverse transcriptase buffer prior to addition of 50 U of reverse transcriptase and incubation for 2 h at 37° C. The reaction was terminated by addition of 1 µl 0.5 M EDTA, and RNA was removed by RNase A digestion (1 µl of 6 µg/ml stock) at 37° C. for 30 min. Following incubation the reaction mixture was diluted to 200 µl with 1X TE buffer, phenol/chloroform extracted, and ethanol precipitated. The pellet was resuspended in 4 µl of 1X TE prior to addition of 3.5 µl of gel loading buffer and heating (5 min at 85° C.). The extension products were electrophoresed on a 6% denaturing polyacrylamide gel (2 µl/lane) alongside a dideoxy sequence ladder generated with the same primer. The site of transcriptional initiation indicated in FIG. 4 is supported by several lines of evidence. Primer extensions were performed using the melA-specific 30mer and total RNA isolated from *S. colwelliana* D, *E. coli* JM101 carrying pUC19, and *E. coli* JM101 carrying pMC3A or pMC3B. pMC3A and pMC3B contain the same 1.9 kb insert ligated in opposite orientations in pUC19 (Table 1). The pMC3B-derived RNA produced readily detectable melA extension products. The size of the major extension product predicted transcriptional initiation from a thymidine residue at position 201. The melA gene in pMC3B is likely to be transcribed from the pUC19 lacZ promoter and the melA promoter as evidenced by the Northern blot analyses. Thus, the larger extension products observed in this reaction probably correspond to premature termination of transcripts initiating from the lacZ promoter. At significantly higher RNA concentrations *E. coli* JM101 pMC3A and *S. colwelliana*-derived RNAs, produced visible extension products that although faint, also predicted initiation at position 201. No extension products were produced from *E. coli* pUC19derived RNA. Interestingly, the *S. colwelliana* D-derived RNA directed synthesis of several larger bands in addition to the primary extension product.

In support of this prediction, construct pMC6A, only initiating transcription from the melA promoter, and deleted for all sequence upstream of cytosine 166, was capable of directing melanin formation in *E. coli*. This establishes that all of the required sequences are within 200 nts of the translational start site. Furthermore, the promoter predicted from the primer extensions is the best overall sigma $^{70}$ consensus sequence within this region. These results supported the primer extension data and were consistent with the prediction of transcription initiation at position 201 in *E. coli* and *S. colwelliana* D.

EXAMPLE 10

Enzymatic assay for tyrosinase activity

Crude lysates and Bio-Gel P100 chromatographic fractions were prepared as described above, and made 1mM for EDTA. All reagents were dissolved in 10 mM $PO_4$ buffer (pH-6.8 in HPLC grade $H_2O$) and passed through a 0.2 μm filter. 80 μl of 4 mM tyrosine, 9.0 μl of 10 mM $PO_4$ buffer (pH 6.8), and 1 μm of 20 mM ascorbic acid were mixed in an Eppendorf microfuge tube. 10 μl of the enzyme fraction or lysate was added to this, mixed thoroughly, and incubated for 10 min at 25° C. Following incubation, 90 μl of the reaction mixture were withdrawn and mixed with 10 μl of 1N perchloric acid to terminate the reaction and precipitate total protein. This was centrifuged in an Eppendorf microfuge (6,400×g) for 3 min, 70 μl of the supernatant was withdrawn, passed through a 0.2 μm microfilter, and placed on ice.

The reaction products were separated on isocratic reverse phase HPLC by loading 20 μl of the acidified filtrate onto a Econosphere C18 reverse phase column (250 mm×4.6 mm) (Alltech Associates Inc., State College, Pa.). The mobile phase was run at a flow rate of 1.5 ml/min (app. 2,500 psi) with a Waters 501 HPLC Pump (Millipore Corp., Waters Division, Milford, Mass.). The column eluant was analyzed with a Waters 460 Electrochemical Detector set at a 0.7 V potential against the reference electrode and a sensitivity range of 20 nA. The electrochemical response data was stored and peaks integrated via direct interface of the detector with the Waters Baseline 810 Chromatography Workstation program installed on an NEC APC IV personal computer (Boxborough, Mass.). Standards of DOPA, 6-OH-DOPA, 5-OH-DOPA were run daily. All standards were obtained from Sigma, except for the 5-OH-DOPA, that was a gift from Dr. Peter Sorter of Hoffman-La Roche Pharmaceuticals. Enzyme activity was defined as the peak area (microvolt-sec response)/mg total protein/min.

Figure 18A:
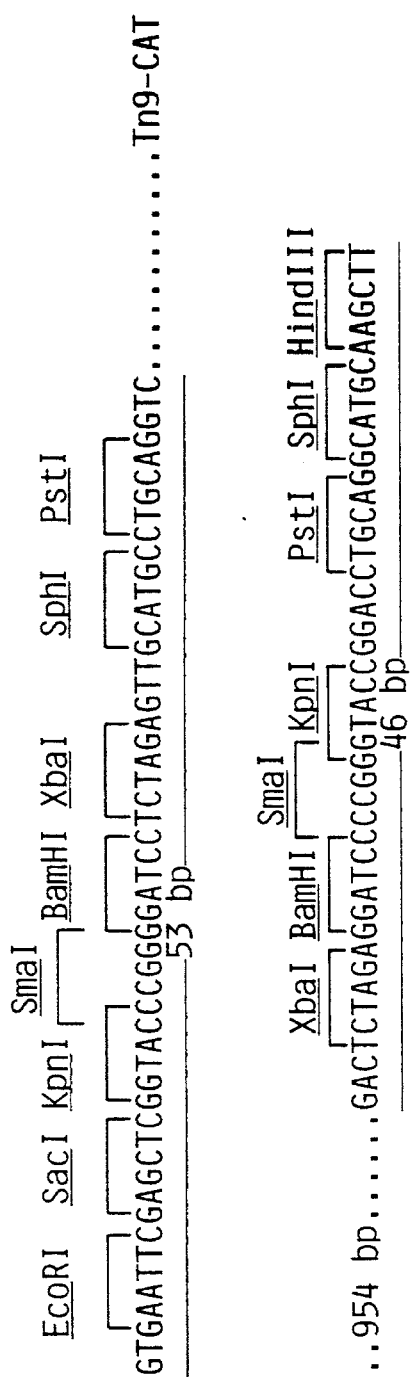
FIG. 18 (A) is the sequence of multiple cloning site polylinkers; (B) is a diagrammatic representation of CAC7 and DNA Restriction sites: B-BamHI, Bs-BstBI, E-EcoRI, H-HindIII, Hc-HincII, K-KpnI, P-PstI, S-SacI, Sm-SmaI, Sp-SphI, X-XbaI.
Figure 18B:
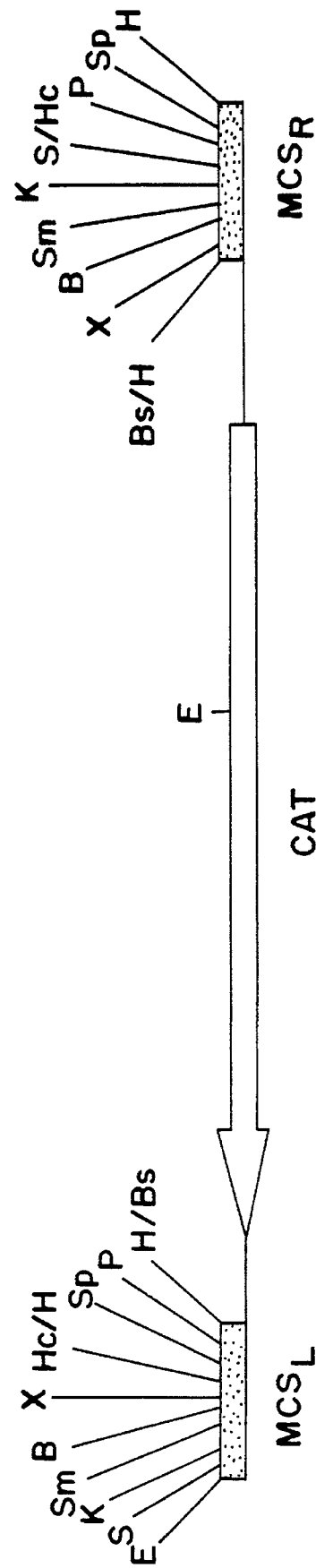

Due to small daily variations in elution times standards were run with all assays. A typical standard set containing 200 picomoles of DOPA, 6-OH-DOPA, and 5-OH-DOPA with elution times of 8.4, 5.4, and 4.5 min (respectively) is shown in FIG. 18 (The large out of range peak observed at 2–3 min is ascorbic acid).

Analysis of a *S. colwelliana* D lysate revealed the production of two distinct peaks from incubation with L-tyrosine. One peak eluted at 8.4 min and based on its retention time was presumed to be DOPA. The second peak, eluted at 3.6 min and clearly did not match the elution profiles of either 5-OH-DOPA or 6-OH-DOPA. This compound was designated Tyr-P. The peak that did elute at approximately the same time as 6-OH-DOPA (5.5 min), was much smaller and not always apparent. This may be trihydroxylated product reported to be produced in low levels during enzymatic conversion of tyrosine to DOPA (G. Agrup, H. Rorsman, and E. Rosengren (1982) *Acta Dermato* (Stockholm) 62:371–376); C. Hansson, H. Rorsman, and E. Rosengren (1980) Acta Dermato Vener. (Stockholm) 60:281–286; M. E. Morrison, and G. Cohen (1983) *Biochemistry* 22:5465–5467).

In negative controls of the assays, incubated without substrate, DOPA was not detected. However, a substantial amount of Tyr-P was present in the lysate prior to addition of substrate, possibly because Tyr-P has higher stability than DOPA. To verify that this product was being synthesized from tyrosine, and not an alternate substrate prior to lysis of the cells, a time course experiment was designed. In this experiment control assays without tyrosine were incubated in parallel with assays without tyrosine were incubated in parallel with assays containing tyrosine. Aliquots were removed every 10 min and the level (μvolt-sec) of DOPA and Tyr-P were measured. No DOPA peak was detected in negative controls, but it was observed to increase with incubation time in the tyrosine-containing assay. Although present in the negative controls, the amount of Tyr-P did not increase with assay time, but did increase steadily in the tyrosine-containing assay.

Lysates of *S. colwelliana* D converted tyrosine to at least 2 products, DOPA and Tyr-P, a faster eluting compound of unknown composition. *E. coli* JM101 carrying the *S. colwelliana* melA gene, synthesized melanin, and produced Tyr-P but no DOPA. This correlated Tyr-P with the melA gene product and melanin formation in *E. coli*, but failed to establish that Tyr-P was also a melanin precursor in *S. colwelliana* D. Conceivably, *S. colwelliana* D utilizes TyrP for alternate purposes, and its intracellular or excreted concentration does not accumulate to sufficient levels for melanin formation.

EXAMPLE 11

Isolation and characterization of *S. colwelliana* PIM1, a spontaneous pigmentation mutant A spontaneous pigmentation mutant of *S. colwelliana* D was isolated. Comparison of this mutant to *S. colwelliana* D showed it to be deficient in tyrosine-induced pigmentation. The mutant and wild type both produced light brown pigment on MB agar. However, while *S. colwelliana* D showed the normal enhancement to dense pigmentation when plated on MG agar supplemented with tyrosine and $CuSO_4$, the mutant showed no such increase. This mutant was designated PIM1 (pigmentation mutant 1).

HPLC assays of *S. colwelliana* PIM1 extracts produced DOPA levels roughly equivalent to strain D, but synthesized only trace levels of Tyr-P. This trace amount was a small peak observed eluting with the same retention time as Tyr-P. This peak did not increase with increasing assay time (data not shown). The results from HPLC assays of extracts prepared from *S. colwelliana* D, *E. coli* JM101 carrying pUC19 or pMC3B, and *S. colwelliana* PIM1 are summarized in Table 2. The *S. colwelliana* PIM1 extracts appeared to synthesize less DOPA than *S. colwelliana* D, but whether this variation reflects a true difference in DOPA-synthesizing activity between the strains is not known.

TABLE 2

| Correlation of MelA with Tyr-P production | | | |
|---|---|---|---|
| Strain[b] | MelA[c] | DOPA | Tyr-P |
| *S. col.* D | + | $7.8 \times 10^6$ | $1.7 \times 10^6$ |
| *S. col* PIM1 | − | $2.8 \times 10^6$ | trace[d] |
| *E. coli* JM101 [pUC19][e] | − | 0 | 0 |
| *E. coli* JM101 [pMC3B], 1PTG[f] | + | 0 | $7.3 \times 10^5$ |

[a]Obtained from calculating peak area minus peak area in negative controls
[b]French-pressed, 0.22 μm filtered crude lysates
[c]Presence of MelA as determined by immunostaining electrotransfers of SDS-PAGE gels with anti-MelA-Lacz
[d]A small peak that did not increase with assay time was detected for this lysate
[e][ ] denotes plasmid-carrier state
[f]Induced with IPTG (100 μg/ml)

Equal amounts of total protein from *S. colwelliana* D and *S. colwelliana* PIM1 were separated by SDS-PAGE, electrotransferred to nitrocellulose, and immunostained with the anti-MelA-LacZ serum. This revealed that *S. colwelliana* D synthesized the expected low amount of MelA, but PIM1 synthesized no detectable MelA.

The spontaneous pigmentation mutant *S. colwelliana* PIM1, does not produce the dense brown pigment characteristic of *S. colwelliana* D on tyrosine/CuSO$_4$ supplemented media. Extracts from this mutant convert tyrosine to DOPA, as in *S. colwelliana* D, but do not produce detectable levels of Tyr-P. Furthermore, there is no detectable MelA in PIM1 extracts. These results also correlated MelA activity in *S. colwelliana* with the synthesis of Tyr-P and with a distinct pigmentation phenotype, thus lending convincing evidence for the direct role of MelA in melanin synthesis.

The nature of the PIM1 mutation. The mutation leading to the PIM1 phenotype dramatically reduces tyrosine-stimulated melanin biosynthesis in *S. colwelliana*. It also disrupts MelA and Tyr-P synthesis. The simplest explanation is that the mutant has a lesion in the melA gene, thus no Tyr-P is synthesized. However, several observations suggest that the PIM1 phenotype may be one manifestation of a more complex deficiency. The mutant is somewhat less robust than *S. colwelliana* D, as judged by growth on plates as well as cell densities in liquid culture. In addition, the protein profile of PIM1 whole cell extracts (silver stained gel) had several notable differences in addition to the lack of MelA. For example, several low molecular weight PIM1 bands are not seen in *S. colwelliana* D, and vice versa. This may reflect a lesion in an *S. colwelliana* gene that is affecting the synthesis of several proteins including MelA. Alternatively, MelA itself may mediate this affect, either directly or indirectly by affecting cellular metabolism. The generation of two distinct reaction products, DOPA and TyrP, suggests that more than one melanin synthesis mechanism is functioning in *S. colwelliana* D.

EXAMPLE 12

Construction of the chloramphenicol mutagenesis cassette

CAC7

Efficient antibiotic resistance markers are required for marker replacement mutagenesis. Preferably, this marker should impart high level resistance to an antibiotic to which the target organism is particularly susceptible. Testing of various MICs on MB agar revealed that *S. colwelliana* D was relatively resistant to many of the more commonly used antibiotics. However, *S. colwelliana* D exhibited high sensitivity to chloramphenicol, which inhibited growth on MG agar at concentrations as low as 1 μg/ml. Resistance to chloramphenicol is derived from the activity of chloramphenicol acetyltransferase (CAT), an enzyme that inactivates the antibiotic via acetylation. In Gram-negative bacteria, several different elements carry and express the CAT gene (T. J. Foster (1983) *Microbiol. Rev.* 47:361–409). One of the most common of these CAT elements is the Tn9 transposon, carried on the cloning vector pBR325 (F. Bolivar (1978) *Gene* 4:121–136).

A Cm$^R$ cassette derived from the pBR325 Tn9 CAT gene was constructed for use in marker replacement mutagenesis among other purposes (Fuqua, in review). The 952 bp BstBI fragment of pBR325 was blunt-ended with Klenow fragment, and ligated into HincII-cleaved pUC19. This ligation transformed into *E. coli* JM101, and Ap$^R$Cm$^R$ transformants were selected. The inserts of these recombinant plasmids were restriction endonuclease mapped and a construct oriented with the CAT gene reading away from the EcoRI site of the pUC19 multiple cloning site was used for further manipulation. This construct was double-digested with SacI and HindIII to generate two cleavage products, of which the smaller fragment carried the intact CAT gene with half of the HincII-split multiple cloning site on each end. The extensions generated from this digestion were digested with Mung Bean Nuclease and this fragment was ligated into the HincII site of pUC19. The ligation mixture was transformed into *E. coli* JM101, and Ap$^R$Cm$^R$ transformants were selected. Two possible orientations were generated, one with a tandem half of the multiple cloning site on each end, and the other with reconstructed multiple cloning sites on each end. The plasmids carried in these transformants were screened by restriction endonuclease cleavage to isolate the latter, desired configuration. One such plasmid agreed with the predictions, and double-stranded sequencing of the polylinker at each end of the cassette confirmed the sequence for these regions of the construct. The plasmid was designated pCAC7, and the CAT cassette it contains, CAC7, is illustrated in FIG. 18. The CAC7 cassette is extremely versatile, and proved to a useful tool in later manipulations.

EXAMPLE 13

In vitro insertional mutagenesis of melA and generation of a mobilizable construct The CAC7 cassette was utilized to inactivate the melA gene in vitro. A 300 bp BglII fragment in the 5' coding region of melA was excised and replaced with the BamHI-cleaved CAC7 cassette. This ligation was transformed into *E. coli* JM101, and plated on LB agar supplemented with Ap, Cm, tyrosine, and CuSO$_4$. All of the resulting Ap$^R$Cm$^R$ transformants were Mel$^-$. The plasmids carried by these transformants were mapped using restriction endonucleases and one recombinant plasmid (pB3A7) with the CAT gene inserted in the opposite orientation to melA was chosen for further manipulation.

For insertion into pGP704, a 2.5 kb fragment carrying all of the melA coding sequence, interrupted by the CAC7 cassette, was liberated from pB3A7 by double digestion with BamHI and NheI. Cleavage of pGP704 with BglII and XbaI produced compatible extensions for ligation with BamHI and NheI extensions, respectively. These two fragments were ligated together and the reaction was transformed into *E. coli* SY327/lambda pir (Table 3), a host with a lysogenically encoded pir gene that transforms at higher efficiencies than *E. coli* SM10/lambda pir. All transformants were Ap$^R$Cm$^R$Mel$^-$ and successful insertion of the melA-::CAC7 fragment into pGP704 was verified with restriction endonuclease mapping. A 6.2 kb recombinant plasmid designated pGB3A7 was purified from *E. coli* SY327/lambda pir and retransformed into *E. coli* SM10/lambda pir.

TABLE 3

| Bacterial strains and plasmids | |
|---|---|
| Strain or plasmid | Relevant characteristics |
| *S. colwelliana* | |
| D | diffusable pigment |
| DR5 | spontaneous Rif$^R$ mutant of strain D |
| PIM1 | spontaneous pigmentation mutant, MelA– |
| PIM1R | spontaneous Rif$^R$ mutant of strain PIM1 |
| DR5::C71 | melA::CAC7, pB3A7 plasmid insertion, pigment–, MelA–, Cm$^R$ |

TABLE 3-continued

Bacterial strains and plasmids

| Strain or plasmid | Relevant characteristics |
|---|---|
| DR5::C72 | melA::CAC7, pB3A7 plasmid insertion, PIM1-like, MelA–, Cm$^R$ |
| *E. coli* | |
| JM101 | host strain, α-complementation strain |
| SY327/λpir | λpir, recA56, high efficiency transformation host for pGP704 cloning |
| SM10[l]glpir | λpir, recA:RP4-2-Rc::Mu Km, mating strain for pGP704 conjugal transfer |
| Plasmids | cloning vector for |
| pUC19 | α-complementation systems, Ap$^R$, LaC+ |
| pBR325 | cloning vector, Ap$^R$, Cm$^R$, Tc$^R$ |
| pRK290 | broad host range mobilizable vector, Tc$^R$ |
| pGP704 | oriR6K, mobRP4 mobilizable cloning vector, Ap$^R$ |
| pMC3A | 1.9 kb HincII-HincII fragment of pMC2 in pUC19, Ap$^R$, Mel+ |
| pMC6A | 1.3 kb NspI-NspI fragment of pMC3A in pUC19, Ap$^R$, Mel+ |
| pCAC7 | 954 bp BstBI-BstBI fragment of pBR325 in pUC19 plus multiple cloning sites, contains CAC7 cassette, Ap$^R$, Cm$^R$ |
| pB3A7 | melA::CAC7, BamHI-cleaved CAC7 cassette inserted in pMC3A deleted for 300 bp BglII-BglII, Ap$^R$, Cm$^R$, Mel– |
| pM6A7 | mlgA::CAC7, SmaI-cleaved CAC7 cassette inserted in the MscI site of pMC6A, Ap$^R$, Cm$^R$, Mel+ |
| pGB3A7 | 2.5 kb BamHI-NheI fragment of pB3A7 inserted in BglII-cleaved pGP704, mobilizable, Ap$^R$, Cm$^R$, Mel– (melA::CAC7) |
| pRKmel | 2.5 kb BamHI-NheI fragment of pM6A7 inserted in pRK290, broad host range, mobilizable Tc$^R$, Cm$^R$, Mel+ |

The same in vitro mutagenesis strategy was attempted for mlgA, the small gene downstream of melA, but the construct carrying the insertionally mutated gene would not transform into *E. coli* SM10/lambda pir, possibly due to a toxic effect of the truncated mlgA gene product.

Conjugation and insertion mutagenesis of the *S. colwelliana* D melA gene, The mobilizable, broad host range RP4 derivative pRK290 (G. Ditta, S. Stanfield, D. Corgin and R. R. Helenski (1980) *Proc. Natl. Acad. Sci., USA* 77:7347–7351) was altered by the insertion of the CAC7 cassette into the single BglII site to generate pRCAM2 (21 kb), a plasmid imparting Tc$^R$ and Cm$^R$ and capable of replication in a wide variety of Gram-negative bacteria (Fuqua, unpublished results, Quintero et al, manuscript in preparation). Rough estimations of conjugal efficiencies of the *E. coli* SM10/lambda pir mating system with *S. colwelliana* D were determined with pRCAM2. *E. coli* SM10/lambda pir carrying pRCAM2 was mated with *S. colwelliana* DR5 (Table 4), a Rif$^R$ derivative of *S. colwelliana* D generated for this study (Table 3). *S. colwelliana* DR5 Cm$^R$ transconjugants were observed after 3 days of incubation with a conjugal efficiency of approximately $1 \times 10^{-6}$. Low plating dilution of the mating mixture ($>10^{-1}$) resulted in the growth of a lawn of cells, but at the higher dilutions ($10^{-3}$–$10^{-4}$) isolated colonies grew at reasonable densities. Plasmid purifications from randomly selected colonies showed that the Rif$^R$ Cm$^R$ conjugants carried pRCAM2 and that the conjugation was proceeding at an efficiency sufficiently high for marker-driven mutagenesis of *S. colwelliana* D.

TABLE 4

Summary of matings

| Plasmid[a] | Recipient[b] | Selection[c] |
|---|---|---|
| pUC19 | DR5 | Rif, Cm |
| pRCAM2 | DR5 | Rif, Cm |
| pGB3A7 | DR5 | Rif, Cm |
| pRK290 | DR5 | Rif, Tc |
| pRK290 | PIM1R | Rif, Tc |
| pRK290 | C71 | Rif, Tc |
| pRK290 | C72 | Rif, Tc |
| pRKmel | DR5 | Rif, Cm |
| pRKmel | PIM1R | Rif, Cm |
| pRKmel | C71 | Rif, Tc |
| pRKmel | C72 | Rif, Tc |

[a]*E. coli* SM10/lamdba pir was used as the donor strain for all matings
[b]All recipient strains were Rif$^R$
[c]Antibiotic concentrations are given in Table 13

The *S. colwelliana* D melA gene was mutagenized by mating *E. coli* SM10/lambda pir carrying pGB3A7 with *S. colwelliana* DR5. Because pGP704-derived plasmids will not replicate outside of their specific *E. coli* hosts, when pGB3A7 was conjugated into *S. colwelliana* DR5d and the transconjugants were placed under Cm selection, only recipients that had gained a chromosomal version of the marker would grow. A region of melA homology flanks both sides of the CAC7 cassette on pGB3A7, thus targeting the recombinational event to the chromosomal melA gene. Conjugation of *E. coli* SM10/lambda pir carrying pUC19 with *S. colwelliana* DR5 served as a negative control (Table 5). Visible colonies grew 3 days after the pGB3A7 mating. Several small, slowly growing colonies were also observed after 1 week of incubation in pUC19 matings. Replica plating of the pGB3A7 and pUC19 transconjugants onto MB agar with Cm, 5 mg/ml tyrosine, and 5 µg/ml CuSO$_4$ revealed that the majority (90%) of pGB3A7-derived transconjugants showed variation in melanin synthesis. Of these, approximately 905 pigmented identically to *S. colwelliana* PIM1 (Mel–), while 10% appeared pigmentless (Pig–). None of the slower growing colonies from the pUC19 mating varied in pigmentation. Each class of pGB3A7 mutant, Pig– and Mel–, was notably different from *S. colwelliana* DR5. To verify that these colonies were not simply spontaneous rifampicin resistant *E. coli* donors, they were replica plated on LB agar and incubated at 37° C. and 25° C. *S. colwelliana* has a strict requirement for at least 1.5% NaCl and does not grow about 30° C. (R. M. Weiner, A. M. Segall and R. R. Colwell (1985) *Appl. Environ. Microbiol.* 49:83–90). Consequently, these transconjugants, being salt limited, did not grow at either temperature. In addition, transconjugants plated on MG agar grew readily at 25° C., but did not grow at 37° C. The mutants, Mel– and Pig–, were designated *S. colwelliana* C72 and *S. colwelliana* C71, respectively.

TABLE 5

Media and Buffers

| Name | Composition |
|---|---|
| MEDIA | |
| LB (Luria-Bertani) | 10 9/L Bacto-Tryptone |
| | 5 g/l yeast extract |
| | 5 g/L NaCl |
| M63 minimal media | 10 µg/L Thiamine |
| | 0.1 mM $MgSO_4$ |
| | 0.4% glucose |
| | 100 al/L 10X M63 salts |
| 10X M63 salts | |
| | 0.22 M $KH_2PO_4$ |
| | 0.4 M $K_2HPO_4$ |
| | 0.15 M $(NH_4)SO_4$ |
| | 18 µM $FeSO_4$ |
| MB (Marine Broth 2216 | 37.4 g/L dried Marine Broth |
| TB (Teriffic Broth) | 24 g/L yeast extract |
| | 12 g/L Bacto-Tryptone |
| | 4 ml/L glycerol |
| | 100 ml/L $K_7HPO_4$ buffer |
| $K_2HPO_4$ buffer | |
| | 0.17 M $KH_2PO_4$ |
| | 0.72 M $K_2HOP_4$ |
| BUFFERS | |
| Aqueous Hybridization Buffer | 40 mM piperazine-N-N1-bis[2-ethanesulfonic acid] (PIPES) |
| | 1 mM EDTA |
| | 400 mM NaCl |
| | 80% deionized formamide |
| DNA/RNA Hybridization Solution | 6X SSPE |
| | 100 µg/ml denatured salmon sperm DNA |
| DNA Prehybridization Solution | 6X SSPE |
| | 0.5% skim milk |
| | 100 µg/ml denatured salmon sperm DNA |
| DNAse I Buffer | 100 mM sodium acetate |
| | 5 mM $MgSO_4$ |
| | pH-5.0 |
| Denaturation Solution | 0.2 N NaOH |
| | 2 mM EDTA |
| Denaturing Gel Loading Buffer | 905 formamide |
| | 20 mM EDTA |
| | 0.05% bromophenol blue |
| | 0.05% xylene cyanol |
| Klenow Buffer | 40 mM $KPO_4$, pH-7.5 |
| | 6.6 mM $MgCl_2$ |
| | 1 mM 2-mereaptoethanol |
| Ligation Buffer | 3 mM Tris-HCl, pH-7.8 |
| | 10 mM $MgCl_2$ |
| | 10 mM dithiothreitol |
| | 0.5 mM ATP |
| Lysis Buffer | 2% sodium dodecylsulfate (SDS) |
| | 10 mM EDTA |
| 1X MOPS Buffer | 20 mM (morpholino)propane-sulfonic acid (MOPS) |
| | 8 mM sodium acetate |
| | 1 mM EDTA |
| | pH-7.0 |
| Mung Bean Nuclease Buffer | 50 mM sodium acetate |
| | 30 mM NaCl |
| | 1 mM $ZnSO_4$ |
| | pH-5.0 |
| Protoplasting Buffer | 15 mM Tris-Cl, pH-8.0 |
| | 0.45 M sucrose |
| | 8 mM EDTA |
| Protoplast Lysis Buffer | 10 mM Tris-Cl, pH-8.0 |
| | 10 mM NaCl |
| | 1.5% SDS |
| RNA Gel Loading Buffer | 50% glycerol |
| | 1 mM EDTA |

TABLE 5-continued

Media and Buffers

| Name | Composition |
|---|---|
| | 0.25% bromophenol blue |
| | 0.25% xylene cyanol |
| RNA Prehybridization Solution | 6X SSPE |
| | 5X Denhardt's solution |
| | 100 µg/ml denatured salmon sperm DNA |
| 50X Denhardt's solution | |
| | 2.5 g/L BSA (Pentax Frac.V) |
| | 2.5 g/L Ficoll type 400 |
| | 2.5 g/L polyvinylpyrolidine |
| RNA Sample Treatment Buffer | 6.6% formaldehyde |
| | 50% formamide |
| | 1X MOPS buffer |
| 2X Reverse Transcriptase Buffer | 100 mM Tris-Cl, pH-7.6 |
| | 120 mM KCl |
| | 20 mM $MgCl_2$ |
| | 10 mM each deoxyribonucleoside triphosphates (dNTPs) |
| | 2 mM dithiothreitol |
| | 2U/µl RNAsin |
| | 100 µg/ml actinomycin D |
| SSPE (saturated saline-phosphate-EDTA) | 150 mM NaCl |
| | 10 mM $NaH_2PO_4$ |
| | 10 mM EDTA |
| | pH-7.4 |
| T4 Polynucleotide Kinase | 70 mM Tris-Cl, pH-7.6 |
| | 10 mM $MgCl_2$ |
| | 5 mM dithiothreitol |
| TAE (Tris-Acetate-EDTA) Buffer | 40 mM Tris-acetate |
| | 1 mN EDTA |
| TE (Tris-EDTA) Buffer | 10 mM Tris-Cl, pH-7.4 |
| | 1 mM EDTA |
| TBE (Tris-Borate-EDTA) | 100 mM Tris-Cl |
| | 83 mM boric acid |
| | 1 mM EDTA |
| Tris-buffered sucrose | 10 mM Tris-Cl, pH-8.0 |
| | 25% sucrose |
| Trio-saturated enol/chloroform | 50% phenol (0.1 M Tris sat.) |
| | 50% chloroform |
| Wash Buffer I | 2X SSPE |
| | 0.01% SDS |
| Wash Buffer II | 0.2X SSPE |
| | 0.01% SDS |

EXAMPLE 14

Figure 19A:
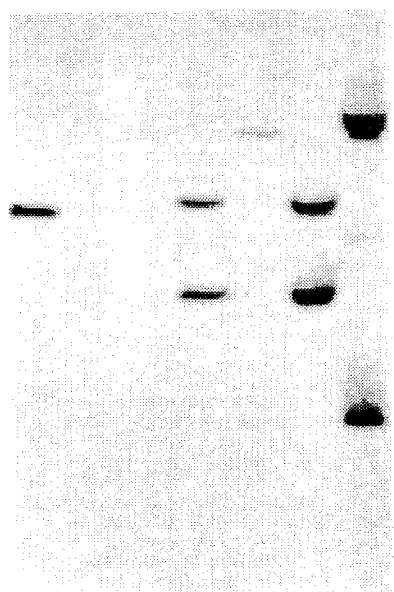
FIG. 19 shows hybridizations with melA-specific and CAC-7 specific probes. (A) Southern blot of HindIII-digested pMC3A (lane 1), PstI-digested genomic DNA from S. colwelliana D (lane 2), S. colwelliana C72 (lane 6). The blot was hybridized with the melA-specific probe (see Materials and Methods). (B) Southern blot of HindIII-digested pCAC7 and identical genomic DNA digests as in A. The blot was hybridized with the CAC7-specific probe (see Materials and Methods). For both blots, right arrows indicate mobilization of HindIII-digested phage lambda size markers.
Figure 19B:
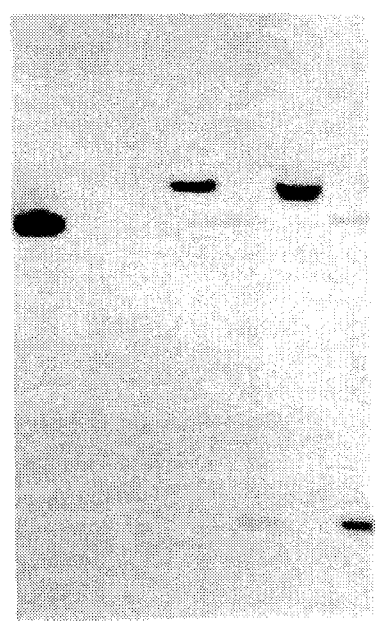
Figure 20A:
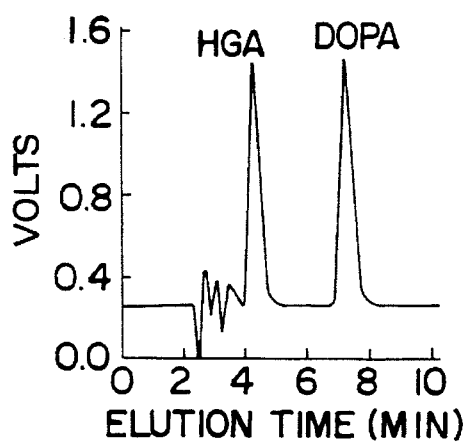
FIG. 20 shows the production of TyrP by HPLC chromatographs with electrochemical detection. (A) Standard solutions of HGA and 3,4-dihydroxyphenylalanine (DOPA). (B) Supernatant from a culture of S. colwelliana D just prior to pigmentation. (C) Lysate form S. colwelliana D, incubated with tyrosine. (D) Supernatant from PT1 cultured in 4 mM tyrosine in phosphate buffer. (E) Lysate from E. coli transformed with the melA gene from S. colwelliana D, incubated with tyrosine. (F) Lysate from S. colwelliana strain C75 with inactivated melA incubated with tyrosine.
Figure 20B:
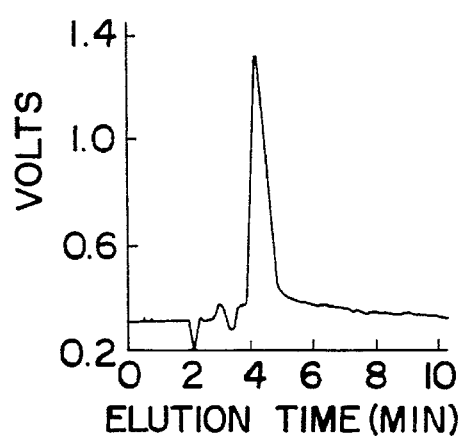
Figure 20C:
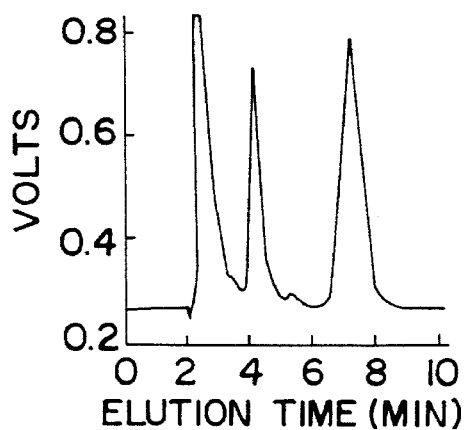
Figure 20D:
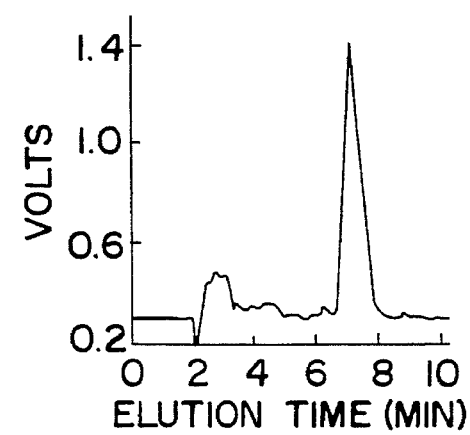
Figure 20E:
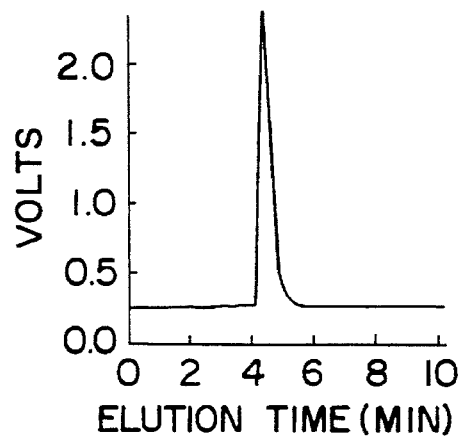

Hybridization of genomic blots from S. colwelliana C71 and C72 DNA to melA and CAC7 specific probes Chromosomal DNA was isolated from S. colwelliana C71 and S. colwelliana C72. These DNA preparations were digested in separate reactions with EcoRI and PstI restriction endonucleases. Following digestion, two identical agarose gels were loaded with half of each digest, separated electrophoretically, and capillary transferred to Zeta-Probe activated nylon membranes under alkaline conditions (K. C. Reed and D. A. Mann (1985) *Nucl. Acids Res.* 13:7207–7221). Two gene probes, one specific for the larger of the two EcoRI fragments of CAC7 (FIG. 18) and the other specific for the carboxy terminal coding region of melA, were generated using the Polymerase Chain Reaction and specific oligonucleotide primers. These were radiolabeled with $^{32}P$ and hybridized to the genomic blots at high stringency. Previous hybridizations of the cloned melA gene to PstI-digested S. colwelliana genomic DNA and a positive control of the same digest (FIG. 19, Lane 2; the 4.2 kb band in this blot is light due to degradation of the control DNA) identified the predicted 4.2 kb fragment. In contrast to this, for both the C71 and C72 digests, the melA-specific probe hybridized with two PstI fragments, 5.0 kb and 3.0 kb. The same probe also hybridized with two EcoRI fragments, 8. kb and 1.4 kb. The presence of two hybridizing PstI fragments and their combined size (8.0 kb, approximately 3.8 kb larger than the S. colwelliana D PstI fragment) indicated that the site-specific mutagenesis of the S. colwelliana D melA gene had successfully inactivated the gene by insertion of the entire pGB3A7 plasmid via a single crossover event (a double crossover event would result in a single hybridizing fragment of approximately 4.0 kb). It also demonstrated that the melA genes of each mutant, C71 (Pig⁻) and C72 (Mel⁻) were identical at the gross structural level.

Hybridization with the CAC7-specific probe identified one PstI fragment, identical in size (5.0 kb) to the larger of the two PstI fragments identified with the melA-specific probe. The EcoRI digests revealed the predicted short CAC7 fragment of approximately 600 bp, and a larger, faintly hybridizing fragment of 4.1 kb. As expected, genomic PstI digests of S. colwelliana D DNA did not hybridize with the CAC7-specific probe. Recombination initiation downstream of the inserted CAC7 cassette of pGB3A7 predicted that hybridizations of PstI-digested DNA with the CAC7 and melA probes would share the smallest of two MelA-reactive bands. Instead, these hybridizations shared the 5.0 kb fragment, the larger of the two, indicating recombination initiation had occurred upstream of the CAC7 cassette. Furthermore, the results also suggest that the integration occurred upstream of the chromosomal EcoRI site. The CAC7 cassette shares a short stretch of identity with the pGP704 multiple cloning site, thus in addition to hybridizing to the short 0.6 kb EcoRI fragment, it also weakly hybridizes with a larger EcoRI fragment. If the pGB3A7 plasmid had integrated at a site downstream, the EcoRI site would have been undisturbed and a fragment at least 3.5 kb larger than the largest MelA-reaction PstI fragment would have hybridized to the CAC7 probe. Instead, the CAC7 probe identified a fragment of 4.1 kb and indicated that the chromosomal EcoRI site was displaced to directly downstream of the integrated plasmid.

EXAMPLE 15

Immunostaining and HPLC activity of site-specific mutants

Cell extracts from S. colwelliana C71 (Pig⁻) and C72 (Mel⁻) and a S. colwelliana DR5 (Mel⁺) control were separated electrophoretically on SDS-PAGE, electrotransferred to a nitrocellulose membrane, and immunostained with the anti MelA-LacZ serum. No 41 kD protein was detected, demonstrating the absence of melA from both of these mutants, while S. colwelliana DR5 stained as expected. HPLC assays of these extracts revealed that C71 and C72 produced expected amounts of DOPA, but neither synthesized Tyr-P.

EXAMPLE 16

Complementation analysis of melA mutants

In order to conduct complementation analysis of the mutants, the melA gene was cloned into the broad host range plasmid pRK290. A SmaI-cleaved CAC7 cassette was ligated into the single MscI site of pMC6A. This inserted CAC7 1 codon downstream of the start site of mlgA and thus did not show the toxic effect of insertion into mlgA observed in earlier experiments, and also did not interfere with melA expression as evidenced by the Mel⁺ phenotype in E. coli carrying this construct (pM6A7). The plasmid pM6A7 was digested with SmaI and HindIII to liberate a 2.3 kb fragment prior to treatment with Klenow fragment to generate blunt ends. The pRK290 vector was cleaved at the BglII site, treated with Klenow fragment, and ligated with the pM6A7 fragment. This ligation was transformed into E. coli JM101 and Tc$^R$Cm$^R$ Mel⁺ colonies were isolated. Plasmid purified from these transformants verified that the pM6A7 SmaI-HindIII fragment had been successfully inserted into pRK290, and this new plasmid was designated pRKmel. This plasmid carries an RP4 origin of replication, functional mob sequences, and a tetracycline resistance marker as well as the CAT and melA genes.

For conjugal transfer of the wild type melA gene into the insertion mutants C71 and C72 as well as S. colwelliana D and S. colwelliana P1M1, pRKmel was transformed into E. coli SM10/lambda pir. E. coli SM10/lambda pir derivatives carrying pRKmel or pRK290 (negative control) were conjugated, in separate matings, with S. colwelliana DR5, S. colwelliana P1M1R, S. colwelliana C71 and S. colwelliana C72.

Transfer of pRKmel into S. colwelliana DR5 had no visible effect on the Mel⁺ phenotype, which was identical to S. colwelliana dr5 WITH Prk290. In contrast, transfer of pRKmel into S. colwelliana P1M1R resulted in restoration of the Mel⁺ phenotype, while transfer of pRK290 had no effect.

Transfer of pRKmel into S. colwelliana C72 restored the Mel⁺ phenotype, while pRK290 had no effect. Interestingly, melanin formation was increased even on MB agar without supplemented tyrosine or copper, implying that melA also contributes to total pigmentation under "normal" conditions.

Transconjugants of S. colwelliana C71 that received pRKmel remained non-pigmented, identical to those that received pRK290. The results of this complementation experiment are summarized in Table 6.

TABLE 6

| | Laccase comparison | | |
|---|---|---|---|
| Organism | Enzyme[a] Mass | Subunit[b] Mass | Copper[c] subunit |
| Neurospora crassa strain OR | 68.2 | 68.2 | 4 |
| Neurospora crassa strain TS | 68.1 | 68.1 | 4 |
| Aspergillus nidulans | — | 67.9 | 4 |
| Botytis | 56 | 56 | 4 |
| Lactarius | 67 | 67 | 4 |
| Podospora | 390 | 71[d] | 4 |
| Peach | 73.5 | — | 2 |

[a]Molecular mass of native protein in kilodaltons (kD)
[b]Molecular mass of subunit(s) in kiladaltons (kD)
[c]Copper ions bound per subunit
[d]Isozymic forms reported

EXAMPLE 17

Identification of the Tyr-P product

Bacterial cultures. Shewanella colwelliana strains were cultured in Marine Broth 2216 (MG; Difco Laboratories, Detroit, Mich.) at 25° C. with vigorous aeration. E. coli, transformed with the plasmid pMC3B, containing the cloned melA gene from *S. colwelliana*, was grown at 37° C. in Luria Broth (LB).

An unidentified bacterium was isolated as a contaminant in our laboratory. This fortuitous organism grew on 4 mM tyrosine in 10 mM phosphate buffer (pH=6.8) as the sole medium. This bacterium metabolized tyrosine and slowly accumulated high concentrations of Tyr-P. These cultures eventually turned pink and the deep maroon. This strain is designated SLC-PT1.

Assays for melA activity. Crude lysates (10 µl) from the French Press were incubated in a 100 µl reaction volume containing 3.2 mM tyrosine and 0.2 mM ascorbic acid in 10 mM phosphate buffer (pH=6.8). After 15 min, 11 µl of 1N perchloric acid was added, and following centrifugation, an aliquot was injected onto the HPLC.

Sample preparation. Culture supernatants were sampled at the indicated times and immediately acidified with 0.1 volumes of 1.0N perchloric acid (PCA). Following centrifugation at 15,000×g for 5 min, the samples were injected directly onto the HPLC system.

Bacterial lysates were prepared by processing harvested cells through a French Press. Cells were harvested by centrifugation of cultures at 16,000×g for 10 min at 4° C. After washing with sodium phosphate buffer, 10 ml of washed cells were disrupted using the French Press at 15,000 psi (40 ml cell). The lysate was cleaned (16,000 ×g, 10 min, 4° C., filtered through a 0.2 µm filter and stored at −20° C.

Electrochemical detection of Tyr-P. Samples were analyzed with a Waters HPLC system fitted with a 4.6×250 mm, $C_{18}$, reverse-phase column (Alltech, State College, Pa.). The mobile phase consisted of 5% acetonitrile (v/v) in 10 mM monochloroacetic acid, 1.3 mM EDTA and 1.3 mM sodium octyl sulfate (pH=2.6). Peaks eluting from the column were detected with a Waters 460 electrochemical detector set at an oxidizing potential of 700 mV. Data were analyzed using the Waters Baseline 810 software. This method was also useful for detecting Mason-Raper intermediates.

Purification of Homogentisic Acid (HGA; formerly Tyr-P)

To purify enough HGA for analysis by NMR and mass spectroscopy, the bacterium SLC-PT1 was cultured in 500 ml volumes. Cultures of *S. colwelliana* were unsatisfactory because HGA was not stable enough in the MB media.

Cultures of SLC-PT1 were monitored until sufficient HGA had accumulated (10–15 d). The cultures were then centrifuged at 16,000×g for 10 min, and the supernatant filtered through a 0.2 µm filter. The filtrate was lyophilized and stored at −20° C. until used.

A sample of the lyophilized material (about 400 mg) was triturated with 3×8 ml of cold (0°–5° C.) methanol and filtered. The filtrate was taken to dryness by rotary evaporation and the residue was taken up in 0.5 ml of 80% methanol. For all subsequent purification steps, HPLC analyses were carried out on an Altex model 332 and eluted peaks were monitored with a Gilson Holochrome UV detector set at 282 nm. The solubilized material was put through a disposable $C_{18}$ extraction column (0.5 g; Baker) and eluted with water. After removal of the solvent, the residue (25 mg) was partially purified on another $C_{18}$ column (10×250 nm; Chromanetics) and eluted with 5% methanol in water at a flow rate of 3 ml/min. Final purification was carried out on yet another $C_{18}$ column (4.6×250 mm; Rainin) and eluted with 2% acetonitrile in water at a flow rate of 1 ml/min. The eluant from the collected peak was removed by vacuum centrifugation.

Production of HGA. Lysates of *S. colwelliana* cells produced HGA when incubated with tyrosine (FIG. 20). In addition *S. colwelliana* was found to produce HGA in the culture medium (data not shown). HGA accumulated to a maximum just prior to pigmentation, after which it could no longer be detected. HGA was only a minor component of the complex MB medium. To facilitate production and characterization of HGA, the melA gene was cloned and overexpressed in *E. coli*. Cultures of transformed *E. coli* became pigmented and lysates also produced HGA (FIG. 20). Untransformed *E. coli* did not pigment or produce HGA (data not shown). Lysates of transformed *E. coli* assayed without tyrosine showed a low basal level of HGA (data not shown). The unknown contaminant SLC-PT1 also accumulated large amounts of HGA in the tyrosine/phosphate medium (FIG. 20). Maximum accumulation of HGA occurred after 10–15 days. In this media, HGA was stable for several weeks. The peaks designated as HGA from these three source were found to coelute the mobile phase composition was modified over a range of acetonitrile. These HPLC conditions resolved HGA from many anticipated interfering compounds such as known precursors and intermediates in melanin pathways. For large-scale production of HGA, SLC-PT1 was used because of the high concentrations of HGA (up to 2 mM) which accumulated in a simple defined medium.

NMR and mass spectrometry. Analysis of the purified material by NMR spectroscopy and mass spectrometry showed it to be identical to authentic homogentisic acid: NMR $^{13}C$ (100 MHz in DMSO-$d_6$) δ36.6, 115.6, 116.8, 118.6, 123.6, 149,6, 151.0, and 176.1; $^1H$ (400 MHz in DMSO-$d_6$) δ3.51 (2H, s), 6.53 (1 H, dd, J=3.1 and 8.6 Hz), 6.60 (1 H, d J=3.1 Hz), and 6.62 (1H, d, J=8.6 Hz); MS (EI-DCI, 70 eV) m/e 168 ($M^+$), 150, 122 (100%), 94.

Additional corroboration of HGA as homogentisic acid. Co-injections of the purified material with homogentisic acid showed a single peak on HPLC under two different combinations of columns and mobile phase composition. The first was a $C_{18}$ column (4.6×250 mm, Rainin) eluted with 2% acetic acid in water at 1 ml/min (retention time= 13.0 min). The second combination was a phenyl column eluted with 5% methanol in 2% acetic acid-water at 1 ml/min (retention time=7.7 min).

Figure 21:
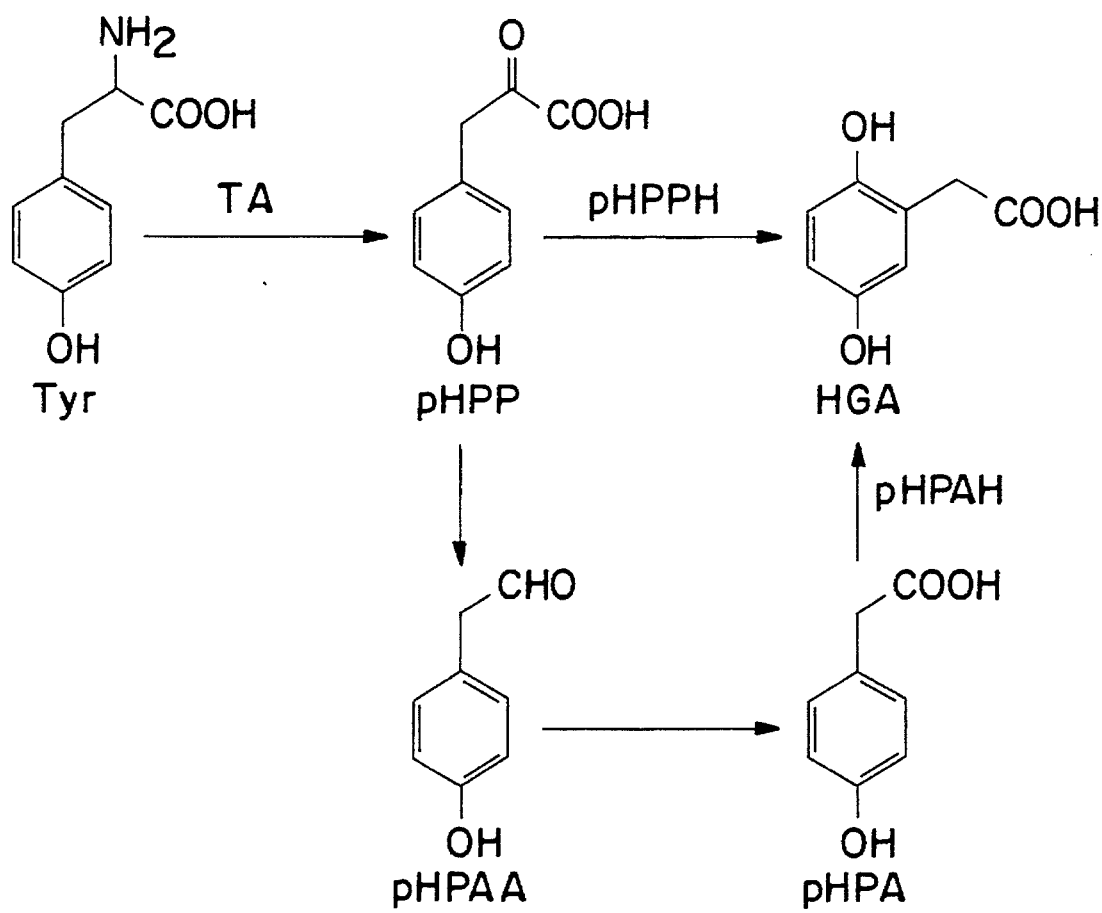
FIG. 21 shows two alternative pathways for the production of homogentisic acid from tyrosine. Substrates: Tyr, tyrosine; pHPP, p-hydroxyphenylpyruvate; pHPAA, p-hydroxyphenylacetaldehyde; pHPA, p-hydroxyphenylacetate; HGA, homogentisic acid. Enzymes: TA, transaminase; pHPPH, pHPP hydroxylase; pHPAH, pHPA hydroxylase.

As shown in FIG. 21, p-OH-phenylpyruvate (pHPP) is the immediate precursor for HGA in tyrosine metabolism. Lysates of *E. coli* transformed with melA produced HGA when pHPP was substituted for tyrosine in the melA assay.

While the invention has been described and illustrated herein by references to various specific material, procedures and examples, it is understood that the invention is not restricted to the particular material, combinations of material, and procedures selected for that purpose. Numerous variations of such details can be implied as will be appreciated by those skilled in the art.

We claim:

1. An isolated nucleic acid encoding a marine melA from the genus Shewanella.

2. The nucleic acid of claim 1 wherein said Shewanella is *S. colwelliana*.

3. The nucleic acid of claim 2 having a nucleotide sequence comprising:

```
   1 TGACTTTATG AGTCGCACAG GTATCGAAGC GGGCTACATG ACCTTACATC AAAAAGGCGT
  61 GCCGCATGGA CCACAACCTG GTCGTACTGA AGCCTCAGTG GGCAAAACTG AAACCTATGA
 121 GTATGCAGTA ATGGTGGACA CCTTTGCACC ACTGCAACTG ACCCAGCATG TCAATCGTGC
 181 ATGAGCAAAG ATTACAACCG TTCCTGGCTA GAAGAGTAAA AGCGTTCAGC CAGTGCTGAA
 241 CATCTAATAA ATATAACACC AGAGGTGACA CCGAAGAGTG CCCTTGGTTG CAATAAGTTG
 301 AAAGAGGATA ATTACATGGC AAGCGAACAA AACCCACTGG GTCTACTTGG TATCGAATTC
 361 ACTGAATTTG CTACACCAGA TCTAGATTTT ATGCATAAAG TTTTTATCGA CTTTGGTTTC
 421 TCAAAACTTA AAAAACACAA GCAGAAAGAT ATTGTTTACT ATAAACAAAA TGATATTAAC
 481 TTTTTACTCA ACAATGAAAA ACAGGGCTTT TCAGCCCAGT TTGCCAAAAC CCATGGCCCA
 541 GCCATTAGTT CTATGGGCTG GCGTGTAGAA GATGCCAACT TTGCCTTTGA AGGTGCTGTA
 601 GCCCGTGGGG CTAAACCCGC AGCAGATGAG GTGAAAGATC TTCCCTATCC CGCTATCTAT
 661 GGCATTGGTG ACAGCCTTAT CTACTTTATC GATACGTTTG GCGATGACAA CAATATCTAC
 721 ACTTCTGATT TTGAAGCGTT AGATGAGCCT ATCATCACCC AAGAGAAAGG CTTCATTGAG
 781 GTCGACCATC TCACCAATAA TGTCCATAAG GGCACCATGG AATATTGGTC AAACTTCTAC
 841 AKAGACATTT TTGGCTTTAC AGAAGTGCGT TACTTCGACA TTAAGGGCTC ACAAACAGCT
 901 CTTATCTCTT ACGCCCTGCG CTCGCCAGAT GGTAGTTTCT GCATTCCAAT TAACGAAGGC
 961 AAAGGCGATG ATCGTAACCA AATTGATGAG TACTTAAAAG AGTACCATGG CCCAGGTGTC
1021 CAACACTTAG CGTTCCGTAG CCGCGACATA GTTGCCTCAC TGGATGCCAT GGAAGGAAGC
1081 TCCATTCAAA CCTTGGACAT AATTCCAGAG TATTACGACA CTATCTTTGA AAAGCTGCCT
1141 CAAGTCACTG AAGACAGAGA TCGCATCAAG CATCATCAAA TCCTGGTAGA TGGCGATGAA
1201 GATGGCTACT TACTGCAAAT TTTCACCAAA AATCTATTTG GTCCAATTTT TATCGAAATC
1261 ATCCAGCGTA AAAACAATCT CGGTTTTGGC GAAGGTAATT TTAAAGCCCT ATTTGAATCG
1321 ATTGAGCGTG ATCAGGTGCG TCGCGGCGTA CTCTAACAAT CACCCAGTGA TCCAACCTCA
1381 AAAAACCAGC ATCGCGCTGG TTTTTTTATT GCAGCACAAC AATAAACCTC TACA
```

4. The nucleic acid of claim 1 having a nucleotide sequence encoding an amino acid sequence comprising:

```
  1 Met Ala Ser Glu Gln Asn Pro Leu Gly Leu Leu Gly Ile
    Glu Phe
 16 Thr Glu Phe Ala Thr Pro Asp Leu Asp Phe Met His Lys
    Val Phe
 31 Ile Asp Phe Gly Phe Ser Lys Leu Lys Lys His Lys Gln
    Lye Asp
 46 Ile Val Tyr Tyr Lys Gln Asn Asp Ile Asn Phe Leu Leu
    Asn Asn
 61 Glu Lye Gln Gly Phe Ser Ala Gln Phe Ala Lye Thr His
    Gly Pro
 76 Ala Ile Ser Ser Met Gly Trp Arg Val Glu Asp Ala Asn
    Phe Ala
 91 Phe Glu Gly Ala Val Ala Arg Gly Ala Lye Pro Ala Ala
    Asp Glu
106 Val Lys Asp Leu Pro Tyr Pro Ala Ile Tyr Gly Ile Gly
    Asp Ser
121 Leu Ile Tyr Phe Ile Asp Thr Phe Gly Asp Asp Asn Asn
    Ile Tyr
136 Thr Ser Asp Phe Glu Ala Leu Asp Glu Pro Ile Ile Thr
    Gln Glu
151 Lye Gly Phe Ile Glu Val Asp His Leu Thr Asn Agn Val
    His Lys
166 Gly Thr Met Glu Tyr Trp Ser Asn Phe Tyr Lys Asp Ile
    Phe Gly
181 Phe Thr Glu Val Arg Tyr Phe Asp Ile Lys Gly Ser Gln
    Thr Ala
196 Leu Ile Ser Tyr Ala Leu Arg Ser Pro Asp Gly Ser Phe
    Cys Ile
211 Pro Ile Asn Glu Gly Lys Gly Asp Asp Arg Asn Gln Ile
    Asp Glu
226 Tyr Leu Lye Glu Tyr Asp Gly Pro Gly Val Gln His Leu
    Ala Phe
241 Arg Ser Arg Asp Ile Val Ala Ser Leu Asp Ala Met Glu
    Gly Ser
256 Ser Ile Gln Thr Lau Asp Ile Ile Pro Glu Tyr Tyr Asp
    Thr Ile
271 Phe Glu Lye Leu Pro Gln Val Thr Glu Asp Arg Asp Arg
    Ile Lys
286 His His Gln Ile Leu Val Asp Gly Asp Glu Asp Gly Tyr
    Leu Leu
301 Gln Ile Phe Thr Lye Asn Leu Phe Gly Pro Ile Phe Ile
    Glu Ile
316 Ile Gln Arg Lys Asn Asn Leu Gly Phe Gly Glu Gly Asn
    Phe Lys
331 Ala Leu Phe Glu Ser Ile Glu Arg Asp Gln Val Arg Arg
    Gly Val
346 Leu
```

5. The nucleic acid of claim 1 wherein said nucleic acid is a DNA, an RNA, or a recombinant DNA.

6. A replicable expression vector comprising the nucleic acid of claim 1 operably linked to a nucleotide sequence element capable of effecting expression of said nucleic acid.

7. The vector of claim 6 wherein said element is at least one of a promoter, a transcription enhancer element, a termination signal, or a translation signal.

8. A microorganism or cell transformed by the nucleic acid of claim 1.

9. A microorganism or cell transformed by the vector of claim 6.

10. In a method of genetic engineering employing a vector having a selectable marker, the improvement which comprises providing a marine melA gene from the genus Shewanella as said selectable marker.

* * * * *